United States Patent
Sharma et al.

(10) Patent No.: US 10,612,058 B2
(45) Date of Patent: Apr. 7, 2020

(54) METHODS FOR SACCHARIFYING A STARCH SUBSTRATE

(71) Applicant: Danisco US Inc., Palo Alto, CA (US)

(72) Inventors: Vivek Sharma, Fremont, CA (US); Paula Johanna Maria Teunissen, Saratoga, CA (US)

(73) Assignee: DANISCO US INC, Palo Alto, CA (US)

( * ) Notice: Subject to any disclaimer, the term of this patent is extended or adjusted under 35 U.S.C. 154(b) by 0 days.

(21) Appl. No.: 15/537,763

(22) PCT Filed: Dec. 18, 2015

(86) PCT No.: PCT/US2015/066784
§ 371 (c)(1),
(2) Date: Jun. 19, 2017

(87) PCT Pub. No.: WO2016/100871
PCT Pub. Date: Jun. 23, 2016

(65) Prior Publication Data
US 2018/0273995 A1    Sep. 27, 2018

Related U.S. Application Data

(60) Provisional application No. 62/094,771, filed on Dec. 19, 2014.

(51) Int. Cl.
| | | |
|---|---|---|
| *C12P 19/02* | (2006.01) | |
| *C12P 19/14* | (2006.01) | |
| *C12P 7/08* | (2006.01) | |
| *C12C 11/00* | (2006.01) | |

(52) U.S. Cl.
CPC ............ *C12P 19/02* (2013.01); *C12C 11/003* (2013.01); *C12P 7/08* (2013.01); *C12P 19/14* (2013.01); *C12Y 302/01003* (2013.01)

(58) Field of Classification Search
None
See application file for complete search history.

(56) References Cited

U.S. PATENT DOCUMENTS

| | | | |
|---|---|---|---|
| 9,540,669 B2* | 1/2017 | Chow | C12P 19/14 |
| 2009/0047382 A1* | 2/2009 | Cates | C12N 15/8242 |
| | | | 426/14 |

FOREIGN PATENT DOCUMENTS

| | | | |
|---|---|---|---|
| AU | 609030 B2 | | 9/1987 |
| EP | 0619947 B1 | | 10/1994 |
| JP | 2011-254748 A1 | | 12/2011 |
| WO | 2008080093 A2 | | 7/2008 |
| WO | WO2008080093 | * | 7/2008 |
| WO | 2013148663 A1 | | 10/2013 |
| WO | WO2013148663 | * | 10/2013 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession ASP18018. Oct. 16, 2008 (Year: 2008).*
Accession AZF60724. Apr. 14, 2011 (Year: 2011).*
U.S. Pat. No. 9,540,669 Alignment of SEQ ID No. 5 to SEQ ID No. 9 (Year: 2017).*
Shigechi, et al., "Direct Production of Ethanol from Raw Corn Starch via Fermentation by Use of a Novel Surface-Engineered Yeast Strain Codisplaying Glucoamylase and #-Amylase", Appl. Environ. Microbiol., vol. 70, No. 8, pp. 5037-5040 (2004).
Blanchard, P. (1992). "Technology of corn wet milling and associated processes." United Kingdom: Elsevier, p. 274, §E, 2nd.

* cited by examiner

*Primary Examiner* — Christian L Fronda

(57) ABSTRACT

Methods are provided for saccharifying a starch substrate, comprising contacting the starch substrate with a glucoamylase consisting or comprising of the amino acid sequence of *Fusarium verticillioides* glucoamylase (Fv-GA) and further contacting the starch substrate with at least one additional glucoamylase. Additional methods are provided for saccharifying and fermenting a starch substrate to produce an end product, a biochemical end product and a fermentable beverage using a combination of Fv-GA and at least one additional glucoamylase.

8 Claims, 6 Drawing Sheets

Specification includes a Sequence Listing.

METHODS FOR SACCHARIFYING A STARCH SUBSTRATE

CROSS-REFERENCE TO RELATED APPLICATIONS

This application is a national phase application under 35 U.S.C. § 371 of International Patent Application No. PCT/US2015/066784, filed Dec. 18, 2015, which claims priority to U.S. Provisional Patent Application No. 62/094,771, filed Dec. 19, 2014, the disclosure of each of which is incorporated by reference herein in its entirety.

SEQUENCE LISTING

Also attached is a sequence listing comprising SEQ ID NOs: 1-12, which are herein incorporated by reference in their entirety.

FIELD OF THE INVENTION

The present disclosure generally relates to glucoamylase (GA) enzymes and methods of using the GAs, particularly in blends, in processes relevant to producing sugars, syrups and biochemicals, including ethanol, are also described.

BACKGROUND OF THE INVENTION

Industrial fermentations predominately use glucose as a feedstock for the production of a multitude of proteins, enzymes, alcohols, and other chemical end products. Typically, glucose is the product of starch processing, which is conventionally a two-step, enzymatic process that catalyzes the breakdown of starch, involving liquefaction and saccharification.

During liquefaction, insoluble granular starch is slurried in water, gelatinized with heat, and hydrolyzed by a thermostable alpha-amylase. During saccharification, the soluble dextrins produced in liquefaction are further hydrolyzed by glucoamylases, producing a high glucose syrup containing greater than 95% glucose.

Glucoamylases are exo-acting carbohydrases, capable of hydrolyzing both the linear and branched glucosidic linkages of starch (e.g., amylose and amylopectin) to produce fermentable sugars from starch (e.g., an enzyme-liquefied starch substrate). The fermentable sugars, e.g., low molecular weight sugars, such as glucose, may then be converted to fructose by other enzymes (e.g., glucose isomerases); crystallized; or used in fermentations to produce numerous end products (e.g., alcohols, monosodium glutamate, succinic acid, vitamins, amino acids, 1,3-propanediol, and lactic acid).

In view of the central role glucoamylases play in generating glucose from starch, it would be an advantage in the art to provide new blends of glucoamylase (GA) enzymes with improved properties for this conversion. Examples of improved properties of GA blends include, but are not limited to: producing sugars, syrups and biochemical, including but not limited to ethanol.

SUMMARY OF THE INVENTION

Methods are provided for saccharifying a starch substrate, comprising contacting the starch substrate with a glucoamylase consisting or comprising of the amino acid sequence of *Fusarium verticillioides* glucoamylase (Fv-GA) and further contacting the starch substrate with at least one additional glucoamylase. Additional methods are provided for saccharifying and fermenting a starch substrate to produce an end product, a biochemical end product and a fermentable beverage using a combination of Fv-GA and at least one additional glucoamylase.

Embodiments of the invention include:

1. A method for saccharifying a starch substrate, comprising contacting the starch substrate with a glucoamylase consisting of the sequence of Fv-GA (SEQ ID NO: 1), having at least 85% identity to the sequence of Fv-GA (SEQ ID NO: 1), having at least 85% identity to a catalytic domain of Fv-GA (SEQ ID NO: 1), having at least 85% identity to a linker and a catalytic domain of Fv-GA (SEQ ID NO: 1) or having at least 85% identity to an active fragment of Fv-GA (SEQ ID NO: 1) having glucoamylase activity, and contacting the starch substrate with at least one additional glucoamylase.

In some embodiments of method 1, the first recited glucoamylase has 90%, 95%, 98% or 99% identity to the sequence of Fv-GA (SEQ ID NO: 1).

2. The method of 1, wherein the additional glucoamylase comprises Afu-GA (SEQ ID NO: 3) or An-GA (SEQ ID NO: 7).

3. The method of 1 or 2, wherein the additional glucoamylase is Afu-GA (SEQ ID NO: 3) or a glucoamylase having at least 85% identity to SEQ ID NO: 3.

4. The method of 1 or 2, wherein the additional glucoamylase is An-GA (SEQ ID NO: 7) or a glucoamylase having at least 85% identity to SEQ ID NO: 7.

5. The method of any one of 1-4, wherein saccharifying the starch substrate results in a high glucose syrup.

6. The method of any one of 1-5, wherein the high glucose syrup comprises an amount of glucose selected from the list consisting of at least 95.5% glucose, at least 95.6% glucose, at least 95.7% glucose, at least 95.8% glucose, at least 95.9% glucose, at least 96% glucose, at least 96.1% glucose, at least 96.2% glucose, at least 96.3% glucose, at least 96.4% glucose, at least 96.5% glucose and at least 97% glucose.

7. The method of any one of 1-6, further comprising fermenting the high glucose syrup to an end product.

8. The method of 7, wherein saccharifying and fermenting are carried out as a simultaneous saccharification and fermentation (SSF) process.

9. The method of 7 or 8, wherein the end product is alcohol.

10. The method of 9, wherein the end product is ethanol.

11. The method of any one of 1-10, wherein the starch substrate is about, 5% to 99%, 15% to 50% or 40-99% dry solid (DS).

12. The method of any one of 1-11, wherein each glucoamylase is dosed at a range of about 0.01 to about 10 glucoamylase unit (GAU) per gram of dry solid starch (dss).

13. The method of any one of 1-12, wherein the starch substrate is selected from wheat, barley, corn, rye, rice, sorghum, bran, cassava, milo, millet, potato, sweet potato, tapioca, and any combination thereof.

14. The method of any one of 1-13, wherein the starch substrate comprises liquefied starch, gelatinized starch, or granular starch.

15. The method of any one of 1-14, further comprising adding a hexokinase, a xylanase, a glucose isomerase, a xylose isomerase, a phosphatase, a phytase, a pullulanase, a β amylase, an α-amylase, a protease, a cellulase, a hemicellulase, a lipase, a cutinase, a trehalase, an isoamylase, a redox enzyme, an esterase, a transferase, a pectinase, a hydrolase, an alpha-glucosidase, an beta-glucosidase, or a combination thereof to the starch substrate.

16. The method of 15, wherein a pullulanase is further added.

17. A method for saccharifying and fermenting a starch substrate to produce an end product, comprising contacting the starch substrate with a glucoamylase having at least 85% identity to Fv-GA (SEQ ID NO: 1), and a glucoamylase having at least 85% identity to Tr-GA variant CS4 (SEQ ID NO: 9).

In some embodiments of method 17, the first recited glucoamylase has 90%, 95%, 98% or 99% identity to the sequence of Fv-GA (SEQ ID NO: 1). In some embodiments of method 17, the second recited glucoamylase has 90%, 95%, 98% or 99% identity to the sequence of Tr-GA variant CS4 (SEQ ID NO: 9).

18. The method of 17, wherein saccharifying and fermenting are carried out as a simultaneous saccharification and fermentation (SSF) process.

19. The method of 17 or 18, wherein the end product is alcohol.

20. The method of any one of 17-19, wherein the end product is ethanol.

21. The method of 20, wherein the saccharified and fermented starch substrate results in a reduced level of DP4+ and an increased ethanol final concentration.

22. The method of 21, wherein the reduced level of DP4+ is lower than would be achieved under the same saccharification and fermentation conditions, using the same total glucoamylase dose of Fv-GA or Tr-GA variant CS4 individually.

23. The method of 21, wherein the increased ethanol final concentration is higher than would be achieved under the same saccharification and fermentation conditions, using the same total glucoamylase dose of Fv-GA or Tr-GA variant CS4 individually.

24. A method for saccharifying and fermenting a starch substrate to produce a biochemical end product, comprising contacting the starch substrate with a glucoamylase having at least 85% identity to Fv-GA (SEQ ID NO: 1), and with a glucoamylase having at least 85% identity to Hg-GA (SEQ ID NO: 5), under conditions suitable for biochemical fermentation In some embodiments of method 24, the first recited glucoamylase has 90%, 95%, 98% or 99% identity to the sequence of Fv-GA (SEQ ID NO: 1). In some embodiments of method 24, the second recited glucoamylase has 90%, 95%, 98% or 99% identity to the sequence of Hg-GA (SEQ ID NO: 5).

25. The method of 24, wherein the end product is a biochemical selected from the group consisting of an amino acid, an organic acid, citric acid, lactic acid, succinic acid, monosodium glutamate, gluconic acid, sodium gluconate, calcium gluconate, potassium gluconate, glucono delta-lactone, sodium erythorbate, omega 3 fatty acid, butanol, lysine, itaconic acid, 1,3-propanediol, biodiesel, and isoprene.

26. A method of producing a fermented beverage, wherein the method comprises the step of contacting a mash and/or a wort with a glucoamylase having at least 85% identity to Fv-GA (SEQ ID NO: 1), and contacting the starch substrate with at least one additional glucoamylase.

In some embodiments of method 26, the first recited glucoamylase has 90%, 95%, 98% or 99% identity to the sequence of Fv-GA (SEQ ID NO: 1).

DETAILED DESCRIPTION

Figure 1:
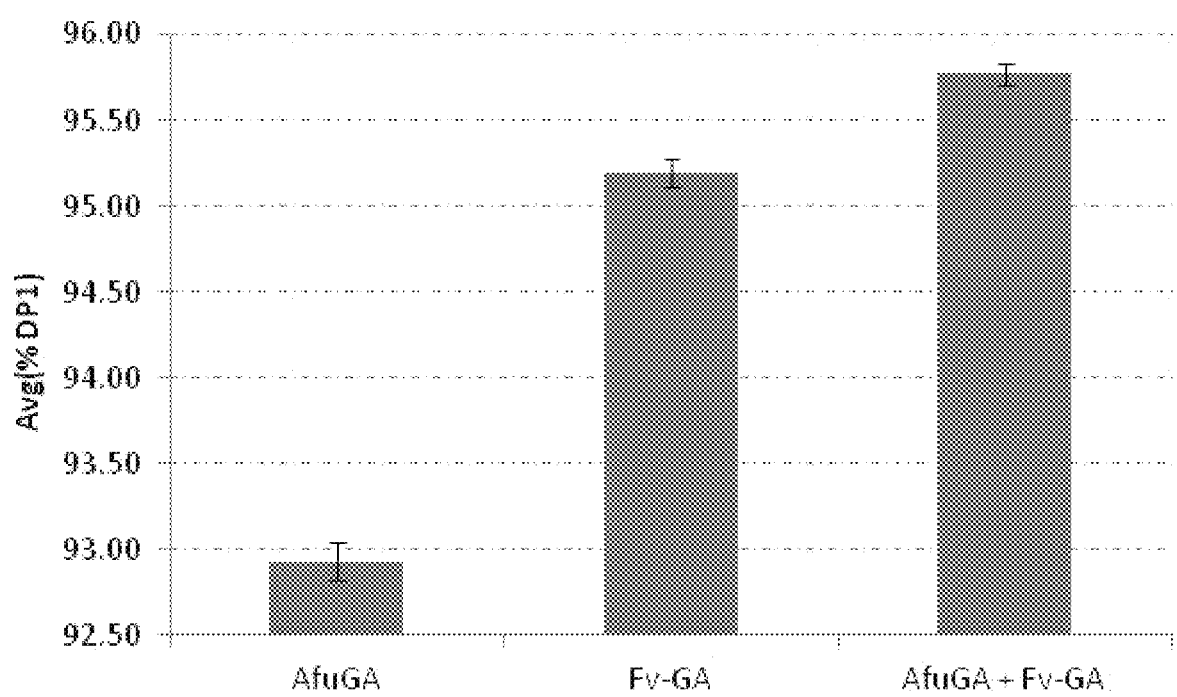
FIG. 1 shows the % glucose at the end of 48 hr for Afu-GA (80 μg/g ds), Fv-GA (80 μg/g ds) and the Afu-GA+Fv-GA (40 μg/g ds+40 μg/g ds) blend.

The invention will now be described in detail by way of reference only using the following definitions and examples. All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 3RD ED., John Wiley and Sons, Ltd., New York (2007), and Hale & Marham, THE HARPER COLLINS DICTIONARY OF BIOLOGY, Harper Perennial, NY (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation. Practitioners are particularly directed to Green and Sambrook *Molecular Cloning: A Laboratory Manual* (Fourth Edition), *Cold Spring Harbor Laboratory Press* 2012, and Ausubel F M et al., 1993, for definitions and terms of the art. It is to be understood that this invention is not limited to the particular methodology, protocols, and reagents described, as these may vary.

The headings provided herein are not limitations of the various aspects or embodiments of the invention which can be had by reference to the specification as a whole. Accordingly, the terms defined immediately below are more fully defined by reference to the specification as a whole.

All publications cited herein are expressly incorporated herein by reference for the purpose of describing and disclosing compositions and methodologies which might be used in connection with the invention.

I. Definitions

The term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may have chemical modifications. The terms "nucleic acid" and "polynucleotide" are used interchangeably. Because the genetic code is degenerate, more than one codon may be used to encode a particular amino acid, and the present compositions and methods encompass nucleotide sequences that encode a particular amino acid sequence. As such, the present invention contemplates every possible variant nucleotide sequence encoding GA or an amino acid variant thereof, all of which are possible given the degeneracy of the genetic code. Unless otherwise indicated, nucleic acid sequences are presented in 5'-to-3' orientation.

Nucleic acid and amino acid sequences that are referred to herein as "non-naturally occurring" are those that are not found in nature, i.e., are the product of human manipulation and/or synthesis.

"Glucoamylase" or "GA" or "GA enzyme" or "GA polypeptide," as used herein is defined as the amyloglucosidase class of enzymes (EC 3.2.1.3, glucoamylase, α-1,4-D-glucan glucohydrolase). These are exo-acting enzymes that catalyze the release of D-glucose from the non-reducing ends of starch and related oligo- and polysaccharides. The enzymes are also capable of hydrolyzing α-1,6 and α-1,3 linkages, although generally at much slower rates than the hydrolysis of α-1,4 linkages.

A "variant" of an enzyme, protein, polypeptide, nucleic acid, or polynucleotide as used herein means that the variant is derived from a parent polypeptide or parent nucleic acid (e.g., native, wild-type or other defined parent polypeptide or nucleic acid) that includes at least one modification or alteration as compared to that parent. Thus, a variant may have a few mutations as compared to a parent, where by "a few" is meant from 1 to 10 mutations. For example, a variant having from 1 to 10 amino acid substitutions as compared to SEQ ID NO:1 can be referred to as a Fv-GA variant having a few substitutions. Alterations/modifications can include a substitution of an amino acid/nucleic acid residue in the parent for a different amino acid/nucleic acid residue at one or more sites, deletion of an amino acid/nucleic acid residue (or a series of amino acid/nucleic acid residues) in the parent at one or more sites, insertion of an amino acid/nucleic acid residue (or a series of amino acid/nucleic acid residues) in the parent at one or more sites, truncation of amino- and/or carboxy-terminal amino acid sequences or 5' and or 3' nucleic acid sequences, and any combination thereof. A variant Fv-GA enzyme according to aspects of the invention retains starch hydrolysis activity but may have an altered property in some specific aspect, e.g., an improved property. For example, a variant Fv-GA enzyme may have an altered pH optimum, improved thermostability, improved hydrolysis of one or more substrates (e.g., DP1 (e.g., glucose), DP3 (e.g., maltotriose, panose), DP4 (e.g., maltotetraose), and/or pullulan) or a combination thereof. In certain embodiments, the variant Fv-GA enzyme contains an amino acid sequence that is at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO:1, or an enzymatically active fragment thereof. Likewise, variant An-GA, variant Afu-GA, variant Hg-GA, variants of Tr-GA variant CS4 and variants of Tr-GA are envisioned having at least 60%, 70%, 80%, 81%, 82%, 83%, 84%, 85%, 86%, 87%, 88%, 89%, 90%, 91%, 92%, 93%, 94%, 95%, 96%, 97%, 98%, or 99% identical to the respective SEQ ID NOs, or an enzymatically active fragment thereof.

"Combinatorial variants" are variants comprising two or more mutations, e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30 or more, substitutions, deletions, and/or insertions.

A "parent" or "parental" polynucleotide, polypeptide, or enzyme sequence (e.g., a "parent Fv-GA enzyme"), or equivalents thereto, as used herein refers to a polynucleotide, polypeptide, or enzyme sequence that was used as a starting point or template for designing a variant polynucleotide, polypeptide, or enzyme. It is further noted that the words "parent" and "parental" are used interchangeably in this context. A "parent Fv-GA enzyme" as used herein means a polypeptide that in its mature form comprises an amino acid sequence which has at least 60% identity with SEQ ID NO:4, including amino acid sequences having at least 60%, 70%, 80%, 81%, 82%, 83%, 84%, 85%, 86%, 87%, 88%, 89%, 90%, 91%, 92%, 93%, 94%, 95%, 96%, 97%, 98%, 99%, or 100% identity with SEQ ID NO:1 (which provides the amino acid sequence of the mature form of wild type GA from *Fusarium verticillioides*) or an allelic variant or a fragment thereof that has starch hydrolysis activity.

The term "wild-type" refers to a naturally-occurring polypeptide or nucleic acid sequence, i.e., one that does not include a human-made variation.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes, arranged to make a new functional nucleic acid, e.g., a promoter from one source and a coding region from another source. Similarly, a heterologous polypeptide will often refer to two or more subsequences that are not found in the same relationship to each other in nature (e.g., a fusion polypeptide).

The term "recombinant" when used with reference, e.g., to a cell, or nucleic acid, polypeptide, or vector, indicates that the cell, nucleic acid, polypeptide or vector, has been modified by the introduction of a heterologous nucleic acid or polypeptide or the alteration of a native nucleic acid or polypeptide, or that the cell is derived from a cell so modified. Thus, for example, recombinant cells express genes that are not found within the native (non-recombinant) form of the cell or express native genes that are otherwise abnormally expressed, under-expressed or not expressed at all. A "recombinant" composition requires manipulation by a human and therefore excludes products of nature.

The terms "isolated" or "purified" as used herein refer to a nucleic acid or polynucleotide that is removed from the environment in which it is naturally produced. In general, in an isolated or purified nucleic acid or polypeptide sample, the nucleic acid(s) or polypeptide(s) of interest are present at an increased absolute or relative concentration as compared to the environment in which they are naturally produced. In some instances, an isolated or purified nucleic acid or polynucleotide is synthetically generated.

The term "enriched" when describing a component or material in a composition (e.g., a polypeptide or polynucleotide) means that the component or material is present at a relatively increased concentration in that composition as compared to the starting composition from which the enriched composition was generated. For example, an enriched GA composition (or sample) is one in which the relative or absolute concentration of GA is increased as compared to the initial fermentation product from the host organism.

As used herein, the terms "promoter" refers to a nucleic acid sequence that functions to direct transcription of a downstream gene. The promoter will generally be appropriate to the host cell in which the target gene is being expressed. The promoter, together with other transcriptional and translational regulatory nucleic acid sequences (also termed "control sequences"), is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences. A "constitutive" promoter is a promoter that is active under most environmental and developmental conditions. An "inducible" promoter is a promoter that is active under environmental or developmental regulation. An example of an inducible promoter useful in the present invention is the *T. reesei* (*H. jecorina*) cbh1 promoter which is deposited in GenBank under Accession Number D86235. In another aspect the promoter is a cbh II or xylanase promoter from *H. jecorina*. Examples of suitable promoters include the promoter from the *A. awamori* or *A. niger* glucoamylase genes (Nunberg, J. H. et al. (1984) Mol. Cell. Biol. 4, 2306-2315; Boel, E. et al. (1984) EMBO J. 3, 1581-1585), the *Mucor miehei* carboxyl protease gene, the *Hypocrea jecorina* glucoamylase I gene (Shoemaker, S. P. et al. (1984) European Patent Application No. EP00137280A1), the *A. nidulans* trpC gene (Yelton, M. et al. (1984) Proc. Natl. Acad. Sci. USA 81, 1470-1474; Mullaney, E. J. et al. (1985) Mol. Gen. Genet. 199, 37-45) the *A. nidulans* alcA gene (Lockington, R. A. et al. (1986) Gene 33, 137-149), the *A. nidulans* tpiA gene (McKnight, G. L. et al. (1986) Cell 46, 143-147), the *A. nidulans* amdS gene (Hynes, M. J. et al. (1983) Mol. Cell Biol. 3, 1430-1439), the *H. jecorina* xln1 gene, the *H. jecorina* cbh2 gene, the *H. jecorina* eg1 gene, the *H. jecorina* eg2 gene, the *H. jecorina* eg3 gene, and higher eukaryotic promoters such as the SV40 early promoter (Barclay, S. L. and E. Meller (1983) Molecular and Cellular Biology 3, 2117-2130).

A nucleic acid is "operably linked" when it is placed into a functional relationship with another nucleic acid sequence. For example, DNA encoding a secretory leader, i.e., a signal peptide, is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. Thus, the term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "signal sequence", "signal peptide", "secretory sequence", "secretory peptide", "secretory signal sequence", "secretory signal peptide" and the like denotes a peptide sequence that, as a component of a larger polypeptide, directs the larger polypeptide through a secretory pathway of a cell in which it is synthesized, as well as nucleic acids encoding such peptides. In general, the larger polypeptide (or protein) is commonly cleaved to remove the secretory/signal peptide during transit through the secretory pathway, where the cleaved form of the polypeptide (i.e., the form without the signal/secretory peptide) is often referred to herein as the "mature form" of the polypeptide. For example, SEQ ID NO:2 provides the amino acid sequence of GA from *F. verticilloides* (Fv-GA) with the signal peptide (i.e., full length Fv-GA).

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

Accordingly, an "expression cassette" or "expression vector" is a nucleic acid construct generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter.

As used herein, the term "plasmid" refers to a circular double-stranded (ds) DNA construct that forms an extrachromosomal self-replicating genetic element when present in many bacteria and some eukaryotes. Plasmids may be employed for any of a number of different purposes, e.g., as cloning vectors, propagation vectors, expression vectors, etc.

As used herein, the term "selectable marker" refers to a nucleotide sequence or polypeptide encoded thereby which is capable of expression in cells and where expression of the selectable marker in cells confers the ability to be differentiated from cells that do not express the selectable marker. In certain embodiments, a selectable marker allows a cell expressing it to grow in the presence of a corresponding selective agent, or under corresponding selective growth conditions. In other embodiments, a selectable marker allows a cell expressing it to be identified and/or isolated from cells that do not express it by virtue of a physical characteristic, e.g., by differences in fluorescence, immunoreactivity, etc.

In general, nucleic acid molecules which encode the Fv-GA or a variant Fv-GA will hybridize, under moderate to high stringency conditions to the wild type sequence provided herein as SEQ ID NO:2 (native Fv-GA gene). However, in some cases an Fv-GA-encoding nucleotide sequence is employed that possesses a substantially different codon usage, while the enzyme encoded by the Fv-GA-encoding nucleotide sequence has the same or substantially the same amino acid sequence as the native enzyme. For example, the coding sequence may be modified to facilitate faster expression of Fv-GA in a particular prokaryotic or eukaryotic expression system, in accordance with the frequency with which a particular codon is utilized by the host (commonly referred to as "codon optimization"). Te'o, et al. (2000), for example, describes the optimization of genes for expression in filamentous fungi. Such nucleic acid sequences are sometimes referred to as "degenerate" or "degenerated sequences".

A nucleic acid sequence is considered to be "selectively hybridizable" to a reference nucleic acid sequence if the two sequences specifically hybridize to one another under moderate to high stringency hybridization and wash conditions. Hybridization conditions are based on the melting temperature (Tm) of the nucleic acid binding complex or probe. For example, "maximum stringency" typically occurs at about Tm-5° C. (5° below the Tm of the probe); "high stringency" at about 5-10° below the Tm; "moderate" or "intermediate stringency" at about 10-20° below the Tm of the probe; and "low stringency" at about 20-25° below the Tm. Functionally, maximum stringency conditions may be used to identify sequences having strict identity or near-strict identity with the hybridization probe; while high stringency conditions are used to identify sequences having about 80% or more sequence identity with the probe.

Moderate and high stringency hybridization conditions are well known in the art (see, for example, Sambrook, et al, 1989, Chapters 9 and 11, and in Ausubel, F. M., et al., 1993, expressly incorporated by reference herein). An example of high stringency conditions includes hybridization at about 42° C. in 50% formamide, 5×SSC, 5×Denhardt's solution, 0.5% SDS and 100 μg/ml denatured carrier DNA followed by washing two times in 2×SSC and 0.5% SDS at room temperature and two additional times in 0.1×SSC and 0.5% SDS at 42° C.

As used herein, the terms "transformed", "stably transformed" or "transgenic" with reference to a cell means the cell has a non-native (heterologous) nucleic acid sequence integrated into its genome or as an episomal plasmid that is maintained through multiple generations.

As used herein, the term "expression" refers to the process by which a polypeptide is produced based on the nucleic acid sequence of a gene. The process generally includes both transcription and translation.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

By the term "host cell" is meant a cell that contains a vector and supports the replication, and/or transcription and/or transcription and translation (expression) of the expression construct. Host cells for use in the present invention can be prokaryotic cells, such as E. coli, or eukaryotic cells such as yeast, plant, insect, amphibian, or mammalian cells. In certain embodiments, host cells are filamentous fungi.

When an amino acid position (or residue) in a first polypeptide is noted as being "equivalent" to an amino acid position in a second, related polypeptide, it means that the amino acid position of the first polypeptide corresponds to the position noted in the second, related polypeptide by one or more of (i) primary sequence alignment (see description of sequence alignment and sequence identity below); (ii) structural sequence homology; or (iii) analogous functional property. Thus, an amino acid position in a first GA enzyme (or a variant thereof) can be identified as "equivalent" (or "homologous") to an amino acid position in a second GA enzyme (or even multiple different GA enzymes).

Primary Sequence Alignment:

Equivalent amino acid positions can be determined using primary amino acid sequence alignment methodologies, many of which are known in the art. For example, by aligning the primary amino acid sequences of two or more different GA enzymes, it is possible to designate an amino acid position number from one GA enzyme as equivalent to the position number of another one of the aligned GA enzymes. In this manner, the numbering system originating from the amino acid sequence of one GA enzyme (e.g., the Fv-GA enzyme denoted in SEQ ID NO: 1) can be used to identify equivalent (or homologous) amino acid residues in other GA enzymes.

Structural Sequence Homology:

In addition to determining "equivalent" amino acid positions using primary sequence alignment methodologies, "equivalent" amino acid positions may also be defined by determining homology at the level of secondary and/or tertiary structure. For example, for a glucoamylase whose tertiary structure has been determined by x-ray crystallography, equivalent residues can be defined as those for which the atomic coordinates of two or more of the main chain atoms of a particular amino acid residue of the glucoamylase are within 0.13 nm and preferably 0.1 nm after alignment with Fv-GA (N on N, CA on CA, C on C, and O on O). Alignment is achieved after the best model has been oriented and positioned to give the maximum overlap of atomic coordinates of non-hydrogen protein atoms of the glucoamylase in question to Fv-GA. The best model is the crystallographic model that gives the highest resolution available. Where two or more different models have equal resolution, the model with the lowest R factor for experimental diffraction data, using the equation below, is used.

$$R \text{ factor} = \frac{\sum_h |Fo(h)| - |Fc(h)|}{\sum_h |Fo(h)|}$$

Analogous Functional Property:

Equivalent amino acid residues in a first polypeptide which are functionally analogous to a specific residue of a second related polypeptide (e.g., a first glucoamylase and Fv-GA) are defined as those amino acids in the first polypeptide that adopt a conformation such that they alter, modify, or contribute to polypeptide structure, substrate binding, or catalysis in a manner defined and attributed to a specific residue of the second related polypeptide. When a tertiary structure has been obtained by x-ray crystallography for the first polypeptide, amino acid residues of the first polypeptide that are functionally analogous to the second polypeptide occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of the second polypeptide.

The term "improved property" or "improved performance" and the like with respect to a variant enzyme (e.g., a GA variant) is defined herein as a characteristic or activity associated with a variant enzyme which is improved as compared to its respective parent enzyme. Improved properties include, but are not limited to, improved thermostability or altered temperature-dependent activity profile, improved activity or stability at a desired pH or pH range, improved substrate specificity, improved product specificity, and improved stability in the presence of a chemical or other component in a starch conversion process step, etc. Improved performance may be determined using a particular assay(s) including, but not limited to: (a) expression, (b) hydrolytic activity on DP2 substrate, (c) hydrolytic activity on DP7 substrate, (d) hydrolytic activity on panose substrate, (e) hydrolytic activity on pullulan substrate, (f) hydrolytic activity on granular corn starch (CS), (g) thermostability, (h) glucose inhibition, (i) reversion activity, and (j) hydrolytic activity on an amylopectin substrate.

The term "improved thermostability" with respect to a variant protein (e.g., a GA variant) is defined herein as a variant enzyme displaying retention of a greater fraction of enzymatic activity after a period of incubation at an elevated temperature relative to the parent enzyme. Such a variant may or may not display an altered thermal activity profile relative to the parent. For example, a variant may have an improved ability to refold following incubation at elevated temperature relative to the parent.

By "improved product specificity" is meant a variant enzyme displaying an altered product profile as compared to the parent enzyme, where the altered product profile of the variant is improved in a given application as compared to the parent. A "product profile" is defined herein as the chemical composition of the reaction products produced by the enzyme of interest.

By "improved substrate specificity" is meant a variant enzyme that targets a specific substrate (or class of substrate) for hydrolysis in a manner different than the parent enzyme, such that the variant has improved performance in a given application as compared to the parent.

By "improved chemical stability" is meant that a variant enzyme displays retention of enzymatic activity after a period of incubation in the presence of a chemical or chemicals that reduce the enzymatic activity of the parent enzyme under the same conditions. Variants with improved chemical stability are better able to catalyze a reaction in the presence of such chemicals as compared to the parent enzyme.

A "pH range," with reference to an enzyme, refers to the range of pH values under which the enzyme exhibits catalytic activity.

The terms "pH stable" and "pH stability," with reference to an enzyme, relate to the ability of the enzyme to retain activity over a wide range of pH values for a predetermined period of time (e.g., 15 min., 30 min., 1 hour).

As used herein, "starch" refers to any material comprised of the complex polysaccharide carbohydrates of plants, comprised of amylose and amylopectin with the formula $(C_6H_{10}O_5)_x$, wherein "X" can be any number. In particular, the term refers to any plant-based material including but not limited to grains, grasses, tubers and roots and more specifically wheat, barley, corn, rye, rice, sorghum, brans, cassava, millet, potato, sweet potato, and tapioca. "Granular starch" refers to uncooked (raw) starch, which has not been subject to gelatinization, where "starch gelatinization" means solubilization of a starch molecule to form a viscous suspension.

"Degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. DP7 denotes polymers with seven anhydroglucopyranose units.

As used herein, "hydrolysis of starch" and the like refers to the cleavage of glucosidic bonds with the addition of water molecules. Thus, enzymes having "starch hydrolysis activity" catalyze the cleavage of glucosidic bonds with the addition of water molecules As used herein, "fermentable sugars" refer to saccharides that are capable of being metabolized under fermentation conditions. These sugars typically refer to glucose, maltose, and maltotriose (DP1, DP2, and DP3).

As used herein, "total sugar content" refers to the total sugar content present in a starch composition.

"Percent sequence identity" or grammatical equivalents means that a particular sequence has at least a certain percentage of amino acid residues identical to those in a specified reference sequence using an alignment algorithm. An example of an algorithm that is suitable for determining sequence similarity is the BLAST algorithm, which is described in Altschul, et al., *J. Mol. Biol.* 215:403-410 (1990). Software for performing BLAST analyses is publicly available through the National Center for Biotechnology Information (<www(dot)ncbi(dot)nlm(dot)nih(dot)gov>). This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, *Proc. Natl. Acad. Sci. USA* 89:10915 (1989)) alignments (B) of 50, expectation (E) of 10, M'5, N'-4, and a comparison of both strands.

The BLAST algorithm then performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a protease if the smallest sum probability in a comparison of the test amino acid sequence to a protease amino acid sequence is less than about 0.1, more preferably less than about 0.01, and most preferably less than about 0.001.

Alignment algorithms can also be employed to identify an amino acid residue (or residues) in a first amino acid sequence (e.g., Fv-GA) that correspond to an amino acid residue (or residues) in a second amino acid sequence (e.g., homologous GA enzymes from other species, e.g., *T. reesei* GA).

When questions of percent sequence identity or corresponding amino acid residues between two sequences arise, alignment using the CLUSTAL W algorithm with default parameters will govern. See Thompson et al. (1994) *Nucleic Acids Res.* 22:4673-4680. Default parameters for the CLUSTAL W algorithm are:

| | |
|---|---|
| Gap opening penalty: | 10.0 |
| Gap extension penalty: | 0.05 |
| Protein weight matrix: | BLOSUM series |
| DNA weight matrix: | IUB |
| Delay divergent sequences %: | 40 |

-continued

| | |
|---|---|
| Gap separation distance: | 8 |
| DNA transitions weight: | 0.50 |
| List hydrophilic residues: | GPSNDQEKR |
| Use negative matrix: | OFF |
| Toggle Residue specific penalties: | ON |
| Toggle hydrophilic penalties: | ON |
| Toggle end gap separation penalty | OFF. |

II. Molecular Biology

Embodiments of the subject invention provide for the expression of a desired glucoamylase enzyme (or combination of glucoamylase enzymes) from glucoamylase-encoding nucleic acids under control of a promoter functional in a host cell of interest, e.g., a filamentous fungus. Therefore, this invention relies on a number of routine techniques in the field of recombinant genetics. Basic texts disclosing examples of suitable recombinant genetics methods are noted above.

Any method known in the art that can introduce mutations into a parent nucleic acid/polypeptide is contemplated by the present invention.

The present invention relates to the expression, purification and/or isolation and use of variant GA enzymes. These enzymes may be prepared by recombinant methods utilizing any of a number of glucoamylase genes known in the art (e.g., the *F. verticillioides* glucoamylase gene comprising SEQ ID NO:2). Any convenient method for introducing mutations may be employed, including site directed mutagenesis. As indicated above, mutations (or variations) include substitutions, additions, deletions or truncations that will correspond to one or more amino acid changes in the expressed GA variant. Again, site directed mutagenesis and other methods of incorporating amino acid changes in expressed proteins at the DNA level can be found in numerous references, e.g., Green and Sambrook, et al. 2012 and Ausubel, et al.

DNA encoding an amino acid sequence variant of a parent GA is prepared by a variety of methods known in the art. These methods include, but are not limited to, preparation by site-directed (or oligonucleotide-mediated) mutagenesis, PCR mutagenesis, and cassette mutagenesis of an earlier prepared DNA encoding the parent GA enzyme.

Site-directed mutagenesis is one method that can be employed in preparing substitution variants. This technique is well known in the art (see, e.g., Carter et al. Nucleic Acids Res. 13:4431-4443 (1985) and Kunkel et al., Proc. Natl. Acad. Sci. USA 82:488 (1987)). Briefly, in carrying out site-directed mutagenesis of DNA, the starting DNA is altered by first hybridizing an oligonucleotide encoding the desired mutation to a single strand of such starting DNA. After hybridization, a DNA polymerase is used to synthesize an entire second strand, using the hybridized oligonucleotide as a primer, and using the single strand of the starting DNA as a template. Thus, the oligonucleotide encoding the desired mutation is incorporated in the resulting double-stranded DNA.

PCR mutagenesis is also suitable for making amino acid sequence variants of the parent GA. See Higuchi, in PCR Protocols, pp. 177-183 (Academic Press, 1990); and Vallette et al., Nuc. Acids Res. 17:723-733 (1989). Briefly, when small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template.

Another method for preparing variants, cassette mutagenesis, is based on the technique described by Wells et al., Gene 34:315-323 (1985). The starting material is the plasmid (or other vector) comprising the starting polypeptide DNA to be mutated. The codon(s) in the starting DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the starting polypeptide DNA. The plasmid DNA is cut at these sites to linearize it. A double-stranded oligonucleotide encoding the sequence of the DNA between the restriction sites but containing the desired mutation(s) is synthesized using standard procedures, wherein the two strands of the oligonucleotide are synthesized separately and then hybridized together using standard techniques. This double-stranded oligonucleotide is referred to as the cassette. This cassette is designed to have 5' and 3' ends that are compatible with the ends of the linearized plasmid, such that it can be directly ligated to the plasmid. This plasmid now contains the mutated DNA sequence.

Alternatively, or additionally, the desired amino acid sequence encoding a desired glucoamylase can be determined, and a nucleic acid sequence encoding such amino acid sequence variant can be generated synthetically.

The desired glucoamylase(s) so prepared may be subjected to further modifications, oftentimes depending on the intended use of the glucoamylase. Such modifications may involve further alteration of the amino acid sequence, fusion to heterologous polypeptide(s) and/or covalent modifications.

III. GA and Variant GA Polypeptides and Nucleic Acids Encoding Same

Glucoamylases (GAs) are produced by numerous strains of bacteria, fungi, yeast and plants. Many fungal glucoamylases are secreted from the cell, for example from strains of *Aspergillus* (Svensson et al., Carlsberg Res. Commun. 48: 529-544 (1983); Boel et al., EMBO J. 3: 1097-1102 (1984); Hayashida et al., Agric. Biol. Chem. 53: 923-929 (1989); U.S. Pat. Nos. 5,024,941; 4,794,175 and WO 88/09795); *Talaromyces* (U.S. Pat. Nos. 4,247,637; 6,255,084; and 6,620,924); *Rhizopus* (Ashikari et al., Agric. Biol. Chem. 50: 957-964 (1986); Ashikari et al., App. Microbio. Biotech. 32: 129-133 (1989) and U.S. Pat. No. 4,863,864); *Humicola* (WO 05/052148 and U.S. Pat. No. 4,618,579); and *Mucor* (Houghton-Larsen et al., Appl. Microbiol. Biotechnol. 62: 210-217 (2003)). Many of the genes that code for these enzymes have been cloned and expressed in yeast, fungal and/or bacterial cells.

Commercially, glucoamylases are very important enzymes and have been used in a wide variety of applications that require the hydrolysis of starch (e.g., for producing glucose and other monosaccharides from starch). Glucoamylases are used to produce high fructose corn sweeteners, which comprise over 50% of the sweetener market in the United States. In general, glucoamylases may be, and commonly are, used with alpha-amylases in starch hydrolyzing processes to hydrolyze starch to dextrins and then glucose. The glucose may be used directly; be converted to fructose by other enzymes (e.g., glucose isomerases); crystallized; or used in fermentations to produce numerous end products (e.g., ethanol, citric acid, succinic acid, ascorbic acid intermediates, glutamic acid, glycerol, 1,3-propanediol and lactic acid).

Glucoamylases may consist of as many as three distinct structural domains, a catalytic domain of approximately 450 residues that is structurally conserved in all glucoamylases, generally followed by a linker region consisting of between 30 and 80 residues that are connected to a starch binding domain (SBD) of approximately 100 residues (also referred to as a carbohydrate binding domain, or CBD). The structure of the *Trichoderma reesei* glucoamylase (TrGA) with all three regions intact was determined to 1.8 Angstrom resolution. See WO 2009/048488 and WO 2009/048487, incorporated herein by reference. Using the determined coordinates, the structure was aligned with the coordinates of the catalytic domain of the glucoamylase from *Aspergillus awamori* strain X100 that was determined previously (Aleshin, A. E., Hoffman, C., Firsov, L. M., and Honzatko, R. B. Refined crystal structures of glucoamylase from *Aspergillus awamori* var. X100. J. Mol. Biol. 238: 575-591 (1994)). The structure of the catalytic domains of these two glucoamylases overlap very closely, and it is possible to identify equivalent residues based on this structural superposition. It is further believed that all glucoamylases share the basic structure.

Given the well-known structure and function relationship of glucoamylases, glucoamylase variants having altered properties have been successfully created and characterized. Certain variants display improved properties as compared to the parent glucoamylases. Examples of improved properties include increased thermostability and increased specific activity. Methods for making and characterizing *T. reesei* GA variants with altered properties have been described in WO 2009/067218 (incorporated herein by reference).

GA enzyme protein (amino acid) and nucleotide sequences are described herein including:

*Fusarium verticillioides* GA (Fv-GA) Protein Sequence (SEQ ID NO: 1)

*Fusarium verticillioides* GA (Fv-GA) DNA Nucleotide Sequence (SEQ ID NO: 2)

*Aspergillus fumigatus* GA (Afu-GA) Protein Sequence (SEQ ID NO: 3)

*Aspergillus fumigatus* GA (Afu-GA) Nucleotide Sequence (SEQ ID NO: 4)

*Humicola grisea* GA (Hg-GA) Protein Sequence (SEQ ID NO: 5)

*Humicola grisea* GA (Hg-GA) Nucleotide Sequence (SEQ ID NO: 6)

*Aspergillus niger* GA (An-GA) Protein Sequence (SEQ ID NO: 7)

*Aspergillus niger* GA (An-GA) Nucleotide Sequence (SEQ ID NO: 8)

*Trichoderma reesei* GA (Tr-GA) variant CS4 Mature Protein Sequence (SEQ ID NO: 9)

*Trichoderma reesei* GA (Tr-GA) Mature Protein Sequence (SEQ ID NO: 10)

*Trichoderma reesei* GA (Tr-GA) Parent Protein Sequence (SEQ ID NO: 11)

*Trichoderma reesei* GA (Tr-GA) Nucleotide Sequence (SEQ ID NO: 12)

Variant GA enzymes are also described herein. The variant GA enzymes have one or more mutations, as set forth herein, with respect to a parent GA enzyme, where the parent GA enzyme has at least 60% (i.e., 60% or greater) amino acid sequence identity to SEQ ID NO:4, including at least 61%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, up to and including 100% amino acid sequence identity to SEQ ID NO:4. Variant GA enzymes (i.e., having one or more mutations) may have at least 60% (i.e., 60% or greater) amino acid sequence identity to SEQ ID NO:4, including at least 61%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% sequence identity to SEQ ID NO:4. In certain embodiments, the parent GA is selected from: a *Trichoderma* strain (e.g., *T. reesei*, *T. longibrachiatum*, *T. strictipilis*, *T. asperellum*, *T. konilangbra*, *T. citrinoviride*, *T. pseudokoningii* and *T. hazianum*), an *Aspergillus* strain (e.g. *A. aculeatus*, *A. niger*, *A. nidulans*, *A. kawachi*, *A. awamori*, *A. clavatus*, *A. terreus*, *A. fumigates*, and *A. orzyae*), a *Talaromyces* strain (e.g. *T. emersonii*, *T. thermophilus*, and *T. duponti*), a *Trametes* strain (e.g., *Trametes cingulata*), a *Hypocrea* strain (e.g. *H. gelatinosa*, *H. orientalis*, *H. vinosa*, *H. jecorina*, *H. schweinitzii*, and *H. citrina*), a *Fusarium* strain (e.g., *F. oxysporum*, and *F. roseum*), a *Humicola* strain (e.g., *H. grisea*, *H. insolens* and *H. lanuginose*), a *Saccharomycopsis* strain (e.g., *S. fibuligera*), *Scytalidium thermophilum*, *Podospora anderina*, or their respective anamorph, teleomorph or holomorph counterpart forms.

In some cases the parent GA is *Fusarium verticillioides* GA (Fv-GA). Further, the variant GA enzyme has starch hydrolysis activity (or is a variant GA fragment having starch hydrolysis activity) where, in certain embodiments, the variant GA has an improved property as compared to the parent GA (as detailed herein).

Aspects of the present invention provide variants of a parent GA enzyme, where the variant has starch hydrolysis activity, has at least 60% (e.g., at least 80%) sequence identity to SEQ ID NO:1, and has at least one improved property over the parent GA enzyme selected from: (a) expression, (b) hydrolytic activity on DP2 substrate, (c) hydrolytic activity on DP7 substrate, (d) hydrolytic activity on panose substrate, (e) hydrolytic activity on pullulan substrate, (f) hydrolytic activity on granular corn starch (CS), (g) thermostability, (h) glucose inhibition, (i) reversion activity, and (j) hydrolytic activity on a amylopectin substrate.

In certain embodiments, a GA variant has at least two, at least three, at least four, at least five, at least six, at least seven, at least 8, at least 9, or more improved properties (selected from the list above) over the parent GA enzyme. In certain embodiments, a variant GA enzyme comprises an amino acid mutation at one or more amino acid positions in Fv-GA (as denoted in SEQ ID NO:1). Because certain parent GA enzymes according to aspects of the invention may not have the same amino acid as wild type Fv-GA, amino acid positions corresponding to the residues noted above may also be designated either by the position number alone.

Alignment of amino acid sequences to determine homology can be determined by using a "sequence comparison algorithm." Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), by visual inspection or MOE by Chemical Computing Group, Montreal Canada. See also the description of "percent sequence identity" provided in the Definitions section above.

IV. Expression of Recombinant GA

Aspects of the subject invention include methods and compositions related to the generation nucleic acids encoding GA enzymes and GA enzyme variants, host cells containing such nucleic acids, the production of GA's or GA variants by such host cells, and the isolation, purification and/or use of the GA variants.

As such, embodiments of the invention provide host cells that have been transduced, transformed or transfected with an expression vector comprising a desired GA or GA variant-encoding nucleic acid sequence. For example, a filamentous fungal cell or yeast cell is transfected with an expression vector having a promoter or biologically active promoter fragment or one or more (e.g., a series) of enhancers which functions in the host cell line, operably linked to a DNA segment encoding a desired GA or GA variant, such that desired GA or GA variant is expressed in the cell line.

A. Nucleic Acid Constructs/Expression Vectors.

Natural or synthetic polynucleotide fragments encoding a desired GA or GA variant may be incorporated into heterologous nucleic acid constructs or vectors, capable of introduction into, and replication in, a host cell of interest (e.g., a filamentous fungal or yeast cell). The vectors and methods disclosed herein are suitable for use in host cells for the expression of a desired GA or GA variant. Any vector may be used as long as it meets the desired replication/expression characteristics in the host cell(s) into which it is introduced (such characteristics generally being defined by the user). Large numbers of suitable vectors and promoters are known to those of skill in the art, some of which are commercially available. Cloning and expression vectors are also described in Sambrook et al., 1989, Ausubel F M et al., 1989, and Strathern et al., 1981, each of which is expressly incorporated by reference herein. Appropriate expression vectors for fungi are described in van den Hondel, C. A. M. J. J. et al. (1991) In: Bennett, J. W. and Lasure, L. L. (eds.) More Gene Manipulations in Fungi. Academic Press, pp. 396-428. The appropriate DNA sequence may be inserted into a plasmid or vector (collectively referred to herein as "vectors") by a variety of procedures. In general, the DNA sequence is inserted into an appropriate restriction endonuclease site(s) by standard procedures. Such procedures and related subcloning procedures are deemed to be within the scope of knowledge of those skilled in the art.

Recombinant host cells comprising the coding sequence for a desired GA or GA variant may be produced by introducing a heterologous nucleic acid construct comprising the desired GA or GA variant coding sequence into the desired host cells (e.g., as described in further detail below). For example, a desired GA or GA variant coding sequence may be inserted into a suitable vector according to well-known recombinant techniques and used to transform a filamentous fungus capable of GA expression. As has been noted above, due to the inherent degeneracy of the genetic code, other nucleic acid sequences which encode substantially the same or a functionally equivalent amino acid sequence may be used to clone and express a desired GA or GA variant. Therefore it is appreciated that such substitutions in the coding region fall within the sequence variants covered by the present invention.

The present invention also includes recombinant nucleic acid constructs comprising one or more of the desired GA's or GA variant-encoding nucleic acid sequences as described above. The constructs comprise a vector, such as a plasmid or viral vector, into which a sequence of the invention has been inserted, in a forward or reverse orientation.

Heterologous nucleic acid constructs may include the coding sequence for a desired GA or GA variant: (i) in isolation; (ii) in combination with additional coding sequences; such as fusion polypeptide or signal peptide coding sequences, where the desired GA or GA variant coding sequence is the dominant coding sequence; (iii) in combination with non-coding sequences, such as introns and control elements, such as promoter and terminator elements or 5' and/or 3' untranslated regions, effective for expression of the coding sequence in a suitable host; and/or (iv) in a vector or host environment in which the desired GA or GA variant coding sequence is a heterologous gene.

In one aspect of the present invention, a heterologous nucleic acid construct is employed to transfer a desired GA or GA variant-encoding nucleic acid sequence into a host cell in vitro, e.g., into established filamentous fungal and yeast lines. Long-term production of a desired GA or GA variant can be achieved by generating a host cell that has stable expression of the GA or GA variant. Thus, it follows that any method effective to generate stable transformants may be used in practicing the invention.

Appropriate vectors are typically equipped with a selectable marker-encoding nucleic acid sequence, insertion sites, and suitable control elements, such as promoter and termination sequences. The vector may comprise regulatory sequences, including, for example, non-coding sequences, such as introns and control elements, i.e., promoter and terminator elements or 5' and/or 3' untranslated regions, effective for expression of the coding sequence in host cells (and/or in a vector or host cell environment in which a modified soluble protein antigen coding sequence is not normally expressed), operably linked to the coding sequence. Large numbers of suitable vectors and promoters are known to those of skill in the art, many of which are commercially available and/or are described in Sambrook, et al., (supra).

Examples of suitable promoters include both constitutive promoters and inducible promoters, examples of which include a CMV promoter, an SV40 early promoter, an RSV promoter, an EF-1α promoter, a promoter containing the tet responsive element (TRE) in the tet-on or tet-off system as described (ClonTech and BASF), the beta actin promoter and the metallothionine promoter that can upregulated by addition of certain metal salts. A promoter sequence is a DNA sequence which is recognized by the particular host cell for expression purposes. It is operably linked to DNA sequence encoding a GA or variant GA polypeptide. Such linkage comprises positioning of the promoter with respect to the initiation codon of the DNA sequence encoding the GA or variant GA polypeptide in the expression vector such that the promoter can drive transcription/translation of the GA or GA variant-encoding sequence. The promoter sequence contains transcription and translation control sequences which mediate the expression of the GA or variant GA polypeptide. Examples include the promoters from the *Aspergillus niger*, *A awamori* or *A. oryzae* glucoamylase, alpha-amylase, or alpha-glucosidase encoding genes; the *A. nidulans* gpdA or trpC Genes; the *Neurospora crassa* cbh1 or trp1 genes; the *A. niger* or *Rhizomucor miehei* aspartic proteinase encoding genes; the *H. jecorina* cbh1, cbh2, egl1, egl2, or other cellulase encoding genes.

The choice of the proper selectable marker will depend on the host cell, and appropriate markers for different hosts are well known in the art. Typical selectable marker genes include argB from *A. nidulans* or *H. jecorina*, amdS from *A. nidulans*, pyr4 from *Neurospora crassa* or *H. jecorina*, pyrG from *Aspergillus niger* or *A. nidulans*. Additional examples of suitable selectable markers include, but are not limited to trpc, trp1, oliC31, niaD or leu2, which are included in heterologous nucleic acid constructs used to transform a mutant strain such as trp-, pyr-, leu- and the like.

Such selectable markers confer to transformants the ability to utilize a metabolite that is usually not metabolized by the filamentous fungi. For example, the amdS gene from *H. jecorina*, which encodes the enzyme acetamidase, allows transformant cells to grow on acetamide as a nitrogen source. The selectable marker (e.g. pyrG) may restore the ability of an auxotrophic mutant strain to grow on a selective minimal medium or the selectable marker (e.g. olic31) may confer to transformants the ability to grow in the presence of an inhibitory drug or antibiotic.

The selectable marker coding sequence is cloned into any suitable plasmid using methods generally employed in the art. Examples of suitable plasmids include pUC18, pBR322, pRAX and pUC100. The pRAX plasmid contains AMA1 sequences from *A. nidulans*, which make it possible to replicate in *A. niger*.

The practice of the present invention will employ, unless otherwise indicated, conventional techniques of molecular biology, microbiology, recombinant DNA, and immunology, which are within the skill of the art. Such techniques are explained fully in the literature. See, for example, Sambrook et al., 1989; Freshney, 1987; Ausubel, et al., 1993; and Coligan et al., 1991.

B. Host Cells and Culture Conditions for GA Enzyme Production

After DNA sequences that encode the GA or GA variants have been cloned into DNA constructs, the DNA is used to transform microorganisms. The microorganism to be transformed for the purpose of expressing a GA or variant GA according to the present invention can be chosen from a wide variety of host cells. The sections below are provided as examples of host cells/microorganisms and are not meant to limit the scope of host cells that can be employed in practicing aspects of the present invention.

(i) Filamentous Fungi

Aspects of the present invention include filamentous fungi which have been modified, selected and cultured in a manner effective to result in desired GA or GA variant production or expression relative to the corresponding non-transformed parental filamentous fungi.

Examples of species of parental filamentous fungi that may be treated and/or modified for desired glucoamylase expression include, but are not limited to *Trichoderma*, *Penicillium* sp., *Humicola* sp., including *Humicola insolens*; *Aspergillus* sp., including *Aspergillus niger*, *Chrysosporium* sp., *Myceliophthora* sp., *Fusarium* sp., *Hypocrea* sp., and *Emericella* sp.

Cells expressing a desired GA or GA variant are cultured under conditions typically employed to culture the parental fungal line. Generally, cells are cultured in a standard medium containing physiological salts and nutrients, such as described in Pourquie, J. et al., Biochemistry and Genetics of Cellulose Degradation, eds. Aubert, J. P. et al., Academic Press, pp. 71-86, 1988 and Ilmen, M. et al., Appl. Environ. Microbiol. 63:1298-1306, 1997. Standard culture conditions are known in the art, e.g., cultures are incubated at 28° C. in shaker cultures or fermenters until desired levels of desired GA variant expression are achieved.

Culture conditions for a given filamentous fungus can be found, for example, in the scientific literature and/or from the source of the fungi such as the American Type Culture Collection (ATCC). After fungal growth has been established, the cells are exposed to conditions effective to cause or permit the expression of a desired GA or GA variant.

In cases where a desired GA or GA variant coding sequence is under the control of an inducible promoter, the inducing agent, e.g., a sugar, metal salt or antibiotic, is added to the medium at a concentration effective to induce expression of the desired GA or GA variant.

In one embodiment, the strain is an *Aspergillus niger* strain, which is a useful strain for obtaining overexpressed protein. For example *A. niger* var *awamori* dgr246 is known to secrete elevated amounts of secreted cellulases (Goedegebuur et al, Curr. Genet (2002) 41: 89-98). Other strains of *Aspergillus niger* var *awamori* such as GCDAP3, GCDAP4 and GAP3-4 are known (Ward et al, 1993, Appl. Microbiol. Biotechnol. 39:738-743).

In another embodiment, the strain is a *Trichoderma reesei* strain, which is a useful strain for obtaining overexpressed protein. For example, RL-P37, described by Sheir-Neiss, et al., Appl. Microbiol. Biotechnol. 20:46-53 (1984) is known to secrete elevated amounts of cellulase enzymes. Functional equivalents of RL-P37 include *Trichoderma reesei* strain RUT-C30 (ATCC No. 56765) and strain QM9414 (ATCC No. 26921). It is contemplated that these strains would also be useful in over-expressing GA or variant GA.

Where it is desired to obtain a GA or GA variant in the absence of potentially detrimental native glucoamylase activity, it is useful to obtain a host cell strain which has had one or more glucoamylase genes deleted prior to introduction of a DNA construct or plasmid containing the DNA fragment encoding the desired GA or GA variant. Such strains may be prepared in any convenient manner, for example by the method disclosed in U.S. Pat. No. 5,246,853 and WO 92/06209, which disclosures are hereby incorporated by reference. By expressing a desired GA or GA variant in a host microorganism that is missing one or more glucoamylase genes (e.g., the endogenous glucoamylase gene of a host cell), identification and subsequent purification procedures, where desired, are simplified.

Gene deletion may be accomplished by inserting a form of the desired gene to be deleted or disrupted into a plasmid by methods known in the art. The deletion plasmid is then cut at an appropriate restriction enzyme site(s), internal to the desired gene coding region, and the gene coding sequence or part thereof replaced with a selectable marker. Flanking DNA sequences from the locus of the gene to be deleted or disrupted, for example from about 0.5 to about 2.0 kb, may remain on either side of the selectable marker gene. An appropriate deletion plasmid will generally have unique restriction enzyme sites present therein to enable the fragment containing the deleted gene, including flanking DNA sequences, and the selectable marker gene to be removed as a single linear piece.

In certain embodiments, more than one copy of DNA encoding a desired GA or GA variant may be present in a host strain to facilitate overexpression of the GA or GA variant. For example, a host cell may have multiple copies of a desired GA or GA variant integrated into the genome or, alternatively, include a plasmid vector that is capable of replicating autonomously in the host organism.

(ii) Yeast

The present invention also contemplates the use of yeast as a host cell for desired one or more GA production. Several other genes encoding hydrolytic enzymes have been expressed in various strains of the yeast *S. cerevisiae*. These include sequences encoding for two endoglucanases (Penttila et al., 1987), two cellobiohydrolases (Penttila et al., 1988) and one beta-glucosidase from *Trichoderma reesei*

(Cummings and Fowler, 1996), a xylanase from *Aureobasidium pullulans* (Li and Ljungdahl, 1996), an alpha-amylase from wheat (Rothstein et al., 1987), etc.

(iii) Other

It is further contemplated that in some embodiments, expression systems in host cells other than filamentous fungal cells or yeast cells may be employed, including insect cell or bacterial cell expression systems. Certain of the bacterial host cells can, for example, be one that is also an ethanologen, such as an engineered *Zymomonas mobilis*, which is not only capable of expressing the enzyme(s)/variant(s) of interest but also capable of metabolizing certain monomeric and other fermentable sugars, turning them into ethanol. The selection of a host cell may be determined by the desires of the user of the GA or GA variants described herein, and thus no limitation in that regard is intended.

C. Introduction of a Desired GA-Encoding Nucleic Acid Sequence into Host Cells.

The invention further provides cells and cell compositions which have been genetically modified to comprise an exogenously provided desired GA or GA variant-encoding nucleic acid sequence. A parental cell or cell line may be genetically modified (e.g., transduced, transformed or transfected) with a cloning vector or an expression vector. The vector may be, for example, in the form of a plasmid, a viral particle, a phage, etc., as further described above.

The methods of transformation of the present invention may result in the stable integration of all or part of the transformation vector into the genome of the host cell. However, transformation resulting in the maintenance of a self-replicating extra-chromosomal transformation vector is also contemplated.

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well-known methods for introducing cloned genomic DNA, cDNA, synthetic DNA or other foreign genetic material into a host cell (see, e.g., Sambrook et al., supra). In essence, the particular genetic engineering procedure used should be capable of successfully introducing a polynucleotide (e.g., an expression vector) into the host cell that is capable of expressing the desired GA or GA variant.

Many standard transfection methods can be used to produce *Trichoderma reesei* cell lines that express large quantities of the heterologous polypeptide. Some of the published methods for the introduction of DNA constructs into strains of *Trichoderma* include: Lorito, Hayes, DiPietro and Harman, 1993, Curr. Genet. 24: 349-356; Goldman, VanMontagu and Herrera-Estrella, 1990, Curr. Genet. 17:169-174; Penttila, Nevalainen, Ratto, Salminen and Knowles, 1987, Gene 6: 155-164; for *Aspergillus*: Yelton, Hamer and Timberlake, 1984, Proc. Natl. Acad. Sci. USA 81: 1470-1474; for *Fusarium*: Bajar, Podila and Kolattukudy, 1991, Proc. Natl. Acad. Sci. USA 88: 8202-8212; for *Streptomyces*: Hopwood et al., 1985, The John Innes Foundation, Norwich, UK and for *Bacillus*: Brigidi, DeRossi, Bertarini, Riccardi and Matteuzzi, 1990, FEMS Microbiol. Lett. 55: 135-138. An example of a suitable transformation process for *Aspergillus* sp. can be found in Campbell et al. Improved transformation efficiency of *A. niger* using homologous niaD gene for nitrate reductase. Curr. Genet. 16:53-56; 1989.

In addition, heterologous nucleic acid constructs comprising a desired glucoamylase-encoding nucleic acid sequence can be transcribed in vitro, and the resulting RNA introduced into the host cell by well-known methods, e.g., by injection.

D. Analysis for GA Nucleic Acid Coding Sequences and/or Protein Expression.

In order to evaluate the expression of a desired GA variant by a cell line that has been transformed with a desired GA variant-encoding nucleic acid construct, assays can be carried out at the protein level, the RNA level or by use of functional bioassays particular to glucoamylase activity and/or production.

In general, assays employed to analyze the expression of a desired GA variant include, but are not limited to, Northern blotting, dot blotting (DNA or RNA analysis), RT-PCR (reverse transcriptase polymerase chain reaction), or in situ hybridization, using an appropriately labeled probe (based on the nucleic acid coding sequence) and conventional Southern blotting and autoradiography.

In addition, the production and/or expression of a desired GA variant may be measured in a sample directly, for example, by assays for glucoamylase activity, expression and/or production. Such assays are described, for example, in Becker et al., Biochem J. (2001) 356:19-30 and Mitsuishi et al., FEBS (1990) 275:135-138, each of which is expressly incorporated by reference herein. The ability of a GA to hydrolyze isolated soluble and insoluble substrates can be measured using assays described in Srisodsuk et al., J. Biotech. (1997) 57:49-57 and Nidetzky and Claeyssens, Biotech. Bioeng. (1994) 44:961-966. Substrates useful for assaying glucoamylase include soluble starch, amylopectin, DP7, paranitrophenyl glucoside. In addition, protein expression may be evaluated by immunological methods, such as ELISA, competitive immunoassays, radioimmunoassays, Western blot, indirect immunofluorescent assays, and the like. Certain of these assays can be performed using commercially available reagents and/or kits designed for detecting GA enzymes. Such immunoassays can be used to qualitatively and/or quantitatively evaluate expression of a desired GA or GA variant. The details of such methods are known to those of skill in the art and many reagents for practicing such methods are commercially available. In certain embodiments, an immunological reagent that is specific for a desired GA or variant GA enzyme but not its parent GA may be employed, e.g., an antibody that is specific for a GA substitution or a fusion partner of the GA or GA variant (e.g., an N or C terminal tag sequence, e.g., a hexa-Histidine tag or a FLAG tag). Thus, aspects of the present invention include using a purified form of a desired GA or GA variant to produce either monoclonal or polyclonal antibodies specific to the expressed polypeptide for use in various immunoassays. (See, e.g., Hu et al., 1991).

V. Methods for Enrichment, Isolation and/or Purification of GA or GA Variant Polypeptide In general, a desired GA or GA variant polypeptide produced in a host cell culture is secreted into the medium (producing a culture supernatant containing the GA or GA variant) and may be enriched, purified or isolated, e.g., by removing unwanted components from the cell culture medium. However, in some cases, a desired GA or GA variant polypeptide may be produced in a cellular form (e.g., cytoplasmic, periplasmic, or otherwise associated with the cell) necessitating recovery from a cell lysate/homogenate. The desired GA or GA variant polypeptide is harvested from the cells or cell supernatants in which it was produced using techniques routinely employed by those of skill in the art. Examples include, but are not limited to, filtration (e.g., ultra- or micro-filtration), centrifugation, density gradient fractionation (e.g., density gradient ultracentrifugation), affinity chromatography (Tilbeurgh et al., 1984), ion-exchange chromatographic methods (Goyal et al., 1991; Fliess et al., 1983; Bhikhabhai et al., 1984; Ellouz et al., 1987), including ion-exchange using materials with high resolution power (Medve et al., 1998), hydrophobic interaction chromatography (Tomaz and Queiroz, 1999), and two-phase partitioning (Brumbauer, et al., 1999).

While enriched, isolated or purified GA or GA variant polypeptide is sometimes desired, in some embodiments, a host cell expressing a GA or GA variant polypeptide is employed directly in an process that requires glucoamylase activity. Thus, enrichment, isolation or purification of the desired GA or GA variant polypeptide is not always required to obtain a GA or GA variant polypeptide composition that finds use in a desired assay or process that requires, or would benefit from, glucoamylase activity. In one such example, GA or GA variant-expressing yeast cells may be added directly into a fermentation process such that the yeast cell expresses the GA or variant GA directly into the fermentation broth where its glucoamylase activity converts a non-fermentable substrate into fermentable sugars for the yeast cell to convert directly to a desired product, e.g., into ethanol (see, e.g., Ilmén et al., *High level secretion of cellobiohydrolases by Saccharomyces cerevisiae* Biotechnology for Biofuels 2011, 4:30).

VI. Compositions

Compositions that include one or more GA or variant GA as disclosed herein are contemplated. The GAs and variant GAs described herein may be used in enzyme compositions including but not limited to starch hydrolyzing and saccharifying compositions, cleaning and detergent compositions (e.g., laundry detergents, dish washing detergents, and hard surface cleaning compositions), alcohol and/or biochemical fermentation compositions, and in animal feed compositions. Further, the variant glucoamylases may be used in baking applications, such as bread and cake production, brewing, healthcare, textile, food, environmental waste conversion processes, bio pulp processing, and biomass conversion applications.

In some embodiments, an enzyme composition including one or more GAs or variant GAs encompassed by the disclosure (e.g., obtained in culture media or recovered and purified from the culture medium) will be used in combination with any one or a combination of the following enzymes: alpha amylases, proteases, pullulanases, isoamylases, cellulases, hemicellulases, xylanases, cyclodextrin glycotransferases, lipases, transferases, phytases, laccases, oxidases, redox enzymes, esterases, cutinases, granular starch hydrolyzing enzyme and other glucoamylases.

In some representative compositions, one or more GA or variant GAs as described herein will be combined with an alpha amylase, such as fungal alpha amylases (e.g., derived from a *Trichoderma* sp.) or bacterial alpha amylases (e.g., derived from a *Bacillus* sp.), including variants, chimeras, and hybrids thereof. In certain embodiments the alpha amylase is an acid stable alpha amylase. In certain embodiments, the alpha amylase is a granular starch hydrolyzing enzyme (GSHE). Commercially available alpha amylases contemplated for use in the GA or variant GA compositions as described herein are available (e.g., from Danisco US Inc. or Novozymes).

In other embodiments, one or more GAs or variant GAs as described herein can be combined with other GAs, either variant or native. In some embodiments, the GAs of the disclosure will be combined with one or more GAs derived from strains of *Aspergillus* or variants thereof, such as *A. oryzae*, *A. niger*, *A. kawachi*, and *A. awamori*; glucoamylases derived from strains of *Humicola* or variants thereof; glucoamylases derived from strains of *Talaromyces* or variants thereof, particularly *T. emersonii*, *T. stipitatus*; glucoamylases derived from strains of *Athelia* or variants thereof, particularly *A. rolfsii*; glucoamylases derived from strains of *Penicillium* or variants thereof, particularly *P. chrysogenum*; *P. oxalicum*; *Trametes*, *Thermomyces*, *Neurospora*, *Phanerochaete*, *Ganoderma*, *Neosartoryia*, *Schizophyllum*, *Acremonium*, *Artomyces*, *Athelia*, *Aureobasidium*, *Byssocorticium*, *Chrysosporium*, *Coniochaeta*, *Disporotrichum*, *Fusarium*, *Gibberella*, *Gloeophillum*, *Leucopaxillus*, *Meripilus*, *Mucor*, *Myceliophthora*, *Sporotrichum*, *Neurospora*, *Nigrofomes*, *Pachykytospora*, *Penicillium*, *Piromyces*, *Rhizomucor*, *Rhizopus*, *Schizophyllum*, *Steccherinum*, *Subulispora*, *Syncephalastrum*, *Talaromyces*, *Thermoascus*, *Thermomyces*, *Thielavia*, *Trametes*, *Valsaria*; and glucoamylases derived from strains of *Trichoderma* or variants thereof, particularly *T. reesei*.

VII. Utility of GA and GA Variants

As detailed above, GAs are very important commercial enzymes used in a wide variety of applications that require the hydrolysis of starch substrates to fermentable sugars (e.g., glucose, maltose, maltotriose, etc.). GAs are used in processes to produce high fructose corn sweeteners, which comprise over 50% of the sweetener market in the United States, as well as in processes for the direct production of glucose. In general, glucoamylases may be, and commonly are, used with alpha-amylases in starch hydrolyzing processes to hydrolyze starch to dextrins and then to glucose. The glucose may be used directly; be converted to fructose by other enzymes (e.g., glucose isomerases); crystallized; or used in fermentations to produce numerous end products (e.g., ethanol, citric acid, succinic acid, ascorbic acid intermediates, glutamic acid, glycerol, 1,3-propanediol and lactic acid).

The one or more GA or GA variant or combinations thereof, may also be effective in direct hydrolysis of starch for syrup and/or biochemicals (e.g., alcohols, organic acids, amino acids, other biochemicals and biomaterials) where the reaction temperature is below the gelatinization temperature of substrate.

In addition, the one or more GA or GA variant or combinations thereof can be useful in a one-step enzymatic conversion process, simultaneous liquefaction and saccharification (SLS), to produce high glucose syrup from gelatinized starch using a liquefying alpha-amylase and a saccharifying glucoamylase above the starch gelatinization temperature. Starch concurrently undergoes gelatinization, liquefaction, and saccharification during simultaneous liquefaction and saccharification in the disclosed methods. In contrast, granular starch still maintains crystalline structure during incubation in a "no-cook" or a direct-starch-to-glucose (DSTG) process. Therefore, due to immediate gelatinization of starch at its operating temperature, SLS significantly reduces the required time for starch solubilization compared to DSTG.

Given the commercial importance of GAs, it can be appreciated that the desired GA or GA variant-encoding nucleic acids, the desired GA or GA variant polypeptides and compositions comprising the same find utility in a wide variety applications. The improved property or properties of the GAs or GA variants described herein can be exploited in many ways. For example, GAs or GA variants with improved performance under conditions of thermal stress can be used to increase starch hydrolysis activity in processes carried out at high temperatures (e.g., temperatures at which the parent GA would perform poorly), allowing a user to reduce the total amount of GA employed (as compared to using the parent GA). Other improved properties of GA or GA variant polypeptides can be exploited, including GAs or GA variants having altered pH optima, increased stability or activity at a specific pH, increased specific activity for a substrate, and/or high level expression in a host cell of interest.

A starch hydrolysis composition containing a desired GA or GA variant as described herein finds use in ethanol production. Ethanol from this process can be further used as an octane enhancer or directly as a fuel in lieu of gasoline, which is advantageous, because ethanol as a fuel source is more environmentally friendly than petroleum derived products. It is known that the use of ethanol will improve air quality and possibly reduce local ozone levels and smog. Moreover, utilization of ethanol in lieu of gasoline can be of strategic importance in buffering the impact of sudden shifts in non-renewable energy and petro-chemical supplies.

Separate saccharification and fermentation is a process whereby starch present in a feedstock, e.g., corn, is converted to glucose and subsequently an ethanologen (e.g., a yeast strain) convert the glucose into ethanol. Simultaneous saccharification and fermentation (SSF) is a process whereby starch present in a feedstock is converted to glucose and, at the same time and in the same reactor, an ethanologen converts the glucose into ethanol. Thus, the GA or GA variants of the invention find use in the both of these processes for the degradation of starch-containing feedstock to generate ethanol.

In some embodiments, a GA or GA variant as described herein is expressed in an ethanologen whereby the enzymatic activity of the variant GA expressed by the ethanologen generates glucose that can be converted to ethanol by the ethanologen.

GA or GA variants as described herein find use in generating host cells for producing biochemical products of interest. As such, aspects of the present disclosure include methods of producing a biochemical by obtaining a host cell expressing a GA or GA variant as described herein and culturing the host cell under conditions to produce the biochemical of interest. It is envisioned that such conditions can include, for example pH conditions of pH 3-8 and for example, temperature conditions of 25-95° C. The host cell may include additional modifications to promote production of the desired biochemical, e.g., to express homologous or heterologous genes, additional variant genes, and/or to delete or otherwise inactivate the expression of one or more endogenous genes. Biochemicals of interest include, but are not limited to alcohols (ethanol, methanol, butanol, etc.) and other organic compounds, including volatile organic molecules (e.g., isoprene).

It is noted that GAs or GA variants with decreased thermostability find use, for example, in areas where the enzyme activity is required to be neutralized at lower temperatures, so that other enzymes that may be present are left unaffected.

One aspect of the invention relates to the use of the GA or GA variant polypeptide according to the invention in the production of a fermented beverage, such as a beer. As such, aspects of the present disclosure include a method of providing/producing a fermented beverage comprising the step of contacting a mash and/or a wort with a GA or GA variant polypeptide as described herein. A further aspect relates to a method of providing a fermented beverage comprising the steps of: (a) preparing a mash, (b) filtering the mash to obtain a wort, and (c) fermenting the wort to obtain a fermented beverage, such as a beer, wherein a GA or GA variant polypeptide is added to: (i) the mash of step (a) and/or (ii) the wort of step (b) and/or (iii) the wort of step (c).

According to yet another aspect, a fermented beverage, such as a beer, is produced or provided by a method comprising the step(s) of (1) contacting a mash and/or a wort with a GA or GA variant polypeptide as described herein; and/or (2) (a) preparing a mash, (b) filtering the mash to obtain a wort, and (c) fermenting the wort to obtain a fermented beverage, such as a beer, wherein a GA or GA variant polypeptide is added to: (i) the mash of step (a) and/or (ii) the wort of step (b) and/or (iii) the wort of step (c).

Aspects of the invention also include a fermented beverage, such as a beer, produced using a GA or GA variant as described above.

The term "beer" is meant to include any fermented wort produced by fermentation/brewing of a starch-containing plant material. Often, beer is produced from malt or adjunct, or any combination of malt and adjunct as the starch-containing plant material.

As used herein the term "malt" is understood as any malted cereal grain, such as malted barley or wheat.

As used herein the term "adjunct" refers to any starch and/or sugar containing plant material which is not malt, such as barley or wheat malt. As examples of adjuncts, mention can be made of materials such as common corn grits, refined corn grits, brewer's milled yeast, rice, sorghum, refined corn starch, barley, barley starch, dehusked barley, wheat, wheat starch, torrified cereal, cereal flakes, rye, oats, corn (maize), potato, tapioca, cassava and syrups, such as corn syrup, sugar cane syrup, inverted sugar syrup, barley and/or wheat syrups, and the like may be used as a source of starch.

As used herein, the term "mash" refers to an aqueous slurry of any starch and/or sugar containing plant material such as grist, e. g. comprising crushed barley malt, crushed barley, and/or other adjunct or a combination hereof, mixed with water later to be separated into wort and spent grains.

As used herein, the term "wort" refers to the unfermented liquor run-off following extracting the grist during mashing.

In another aspect the invention relates to a method of preparing/producing a fermented beverage such as beer comprising mixing the polypeptide of the invention with malt or adjunct.

Examples of beers produced according to the uses and methods above (i.e., in which a GA variant as described herein is used) include, but are not limited to, the following: full malted beer, beer brewed under the "Reinheitsgebot", ale, India Pale Ale (IPA), lager, bitter, Happoshu (second beer), third beer, dry beer, near beer, light beer, low alcohol beer, low calorie beer, porter, bock beer, stout, malt liquor, non-alcoholic beer, non-alcoholic malt liquor and the like, but also alternative cereal and malt beverages such as fruit flavored malt beverages, e. g. citrus flavored, such as lemon-, orange-, lime-, or berry-flavored malt beverages, liquor flavored malt beverages, e. g., vodka-, rum-, or tequila-flavored malt liquor, or coffee flavored malt beverages, such as coffee-flavored malt liquor, and the like.

As seen from above, GA or GA variant polypeptides (and the nucleic acids encoding them) with improved properties as compared to their parent GA enzymes find use in improving any of a number of assays and processes that employ cellobiohydrolases.

EXAMPLES

The present invention is described in further detail in the following examples which are not in any way intended to limit the scope of the invention as claimed. The attached Figures are meant to be considered as integral parts of the specification and description of the invention. All references cited are herein specifically incorporated by reference for all that is described therein.

Example 1

I. Effect of Enzyme Concentration on the Comparison of *A. niger*-GA (An-GA) and *Fusarium verticillioides* GA (Fv-GA) During Saccharification A series of experiments were performed to determine if the novel blend of glucoamylase (An-GA+Fv-GA) produces higher glucose yield compared to the final glucose yield with individual glucoamylases (An-GA, Fv-GA) under a typical saccharification condition. The experiments were carried out using 33.5% ds corn starch liquefact and the pH of the liquefact was adjusted to pH 4.4 using dilute acid. The starch liquefact was placed in a water bath maintained at 60° C. and enzyme(s) were added. All the treatments with just Fv-GA had 0.32 SSUs of AkAA acid stable alpha amylase to match the acid stable alpha amylase present in the An-GA commercial product. The starch liquefact was maintained at 60° C. for 48 hrs and samples were drawn throughout the incubation to analyze the saccharide profile. The glucoamylase dosages are given in GAUs/g DS corn starch and/or µg/g ds and the saccharide profiles at various intervals are given in Tables 1, 2 and 3.

Table 1 shows the saccharide profile for OPTIMAX™ L-400 (commercial product name for glucoamylase An-GA from DuPont Industrial Bioscience) at various dosages. It can be observed that at various dosages An-GA is unable to reach >95.5% glucose at the end of 48 hr.

Table 2 shows the saccharide profile for Fv-GA at various dosages. It can be observed that at various dosages Fv-GA is also unable to reach >95.5% glucose at the end of 48 hr.

Table 3 shows the saccharide profile for the blends of An-GA (OPTIMAX™ L-400)+Fv-GA at various blend ratios, an unexpected increase in final glucose yield greater than 95.5% was observed.

TABLE 1

Saccharide distribution for various An-GA (OPTIMAX™ L-400) dosages

| Sample Name | Dosage | Unit | Time, hr | Avg (% DP4+) | Avg (% DP3) | Avg (% DP2) | Avg (% DP1) |
|---|---|---|---|---|---|---|---|
| OPTIMAX™ L-400 | 140 | µg/g ds | 18 | 6.05 | 0.5 | 2.03 | 91.42 |
| | | | 24 | 4.05 | 0.45 | 2.27 | 93.23 |
| | | | 41 | 1.83 | 0.37 | 2.96 | 94.84 |
| | | | 48 | 1.29 | 0.31 | 3.15 | 95.25 |
| OPTIMAX™ L-400 | 120 | µg/g ds | 18 | 8.06 | 0.55 | 2.03 | 89.36 |
| | | | 24 | 5.18 | 0.48 | 2.18 | 92.17 |
| | | | 41 | 2.31 | 0.39 | 2.78 | 94.52 |
| | | | 48 | 1.62 | 0.3 | 2.92 | 95.16 |
| OPTIMAX™ L-400 | 80 | µg/g ds | 18 | 11.83 | 0.64 | 2.1 | 85.42 |
| | | | 24 | 8.4 | 0.58 | 1.96 | 89.06 |
| | | | 41 | 3.97 | 0.37 | 2.17 | 93.48 |
| | | | 48 | 3.35 | 0.42 | 2.45 | 93.77 |
| OPTIMAX™ L-400 | 40 | µg/g ds | 18 | 21.34 | 0.51 | 6.24 | 71.92 |
| | | | 24 | 16.98 | 0.63 | 3.44 | 78.96 |
| | | | 41 | 9.89 | 0.64 | 2.02 | 87.45 |
| | | | 48 | 8.29 | 0.6 | 2.01 | 89.1 |

TABLE 2

Saccharide distribution for various Fv-GA (*Fusarium*-GA) dosages

| Sample Name | Dosage | Unit | Time, hr | Avg (% DP4+) | Avg (% DP3) | Avg (% DP2) | Avg (% DP1) |
|---|---|---|---|---|---|---|---|
| Fv-GA | 120 | µg/g ds | 16.5 | 7.87 | 0.61 | 4.74 | 86.77 |
| | | | 23 | 1.79 | 0.56 | 3.36 | 94.28 |
| | | | 41.5 | 0.79 | 0.5 | 3.71 | 95 |
| | | | 48 | 0.71 | 0.5 | 3.85 | 94.94 |
| Fv-GA | 80 | µg/g ds | 16.5 | 13.26 | 1.03 | 6.13 | 79.58 |
| | | | 23 | 4.22 | 0.63 | 3.8 | 91.35 |
| | | | 41.5 | 1.1 | 0.55 | 3.03 | 95.32 |
| | | | 48 | 0.93 | 0.54 | 3.07 | 95.46 |
| Fv-GA | 60 | µg/g ds | 16.5 | 12.92 | 1.16 | 6.15 | 79.78 |
| | | | 23 | 5.92 | 0.71 | 4.3 | 89.08 |
| | | | 41.5 | 1.55 | 0.62 | 2.94 | 94.9 |
| | | | 48 | 1.31 | 0.6 | 2.89 | 95.19 |

TABLE 3

Saccharide distribution for various An-GA (OPTIMAX™ L-400) and Fv-GA (*Fusarium verticilloides*-GA) dosages blend ratios

| Sample Name | Dosage | Unit | Time, hr | Avg (% DP4+) | Avg (% DP3) | Avg (% DP2) | Avg (% DP1) |
|---|---|---|---|---|---|---|---|
| OPTIMAX™ L400 + Fv-GA | 120 + 10 | µg/g ds + µg/g ds | 17 | 7.11 | 0.52 | 2.33 | 90.04 |
| | | | 24 | 4.17 | 0.56 | 2.3 | 92.98 |
| | | | 41 | 1.11 | 0.39 | 2.82 | 95.68 |
| | | | 45 | 0.97 | 0.39 | 2.93 | 95.72 |
| OPTIMAX™ L400 + Fv-GA | 80 + 40 | µg/g ds + µg/g ds | 18 | 4.06 | 0.62 | 2.28 | 93.04 |
| | | | 24 | 1.77 | 0.49 | 2.24 | 95.49 |
| | | | 41 | 0.73 | 0.44 | 2.82 | 96 |
| | | | 48 | 0.68 | 0.43 | 2.91 | 95.98 |
| OPTIMAX™ L400 + Fv-GA | 60 + 60 | µg/g ds + µg/g ds | 18 | 3.91 | 0.62 | 2.39 | 93.08 |
| | | | 24 | 1.69 | 0.52 | 2.3 | 95.49 |
| | | | 41 | 0.73 | 0.46 | 2.76 | 96.05 |
| | | | 48 | 0.57 | 0.42 | 2.8 | 96.21 |
| OPTIMAX™ L400 + Fv-GA | 40 + 80 | µg/g ds + µg/g ds | 18 | 4.31 | 0.57 | 2.38 | 92.75 |
| | | | 24 | 1.83 | 0.5 | 2.35 | 95.31 |
| | | | 41 | 0.87 | 0.42 | 2.67 | 96.04 |
| | | | 48 | 0.77 | 0.42 | 2.8 | 96.01 |
| OPTIMAX™ L400 + Fv-GA | 20 + 100 | µg/g ds + µg/g ds | 18 | 5.56 | 0.54 | 2.56 | 91.34 |
| | | | 24 | 2.59 | 0.54 | 2.39 | 94.47 |
| | | | 41 | 1.03 | 0.44 | 2.47 | 96.05 |
| | | | 48 | 0.97 | 0.47 | 2.6 | 95.96 |

The data shown in Tables 1-3 support a surprising discovery that the blend of An-GA+Fv-GA performed better and produced >95.5% glucose whereas the individually used An-GA and Fv-GA did not produce >95.5% glucose. The discovered enzyme blend is beneficial for the glucose syrup producers as blending of An-GA+Fv-GA resulted in higher glucose yield.

Example 2

I. Effect of Different Glucoamylases (Purified Glucoamylases from *Trichoderma reesei* (Tr-GA), *Humicola grisea* (H-GA), *Aspergillus fumigatus* (Afu-GA), and *Fusarium verticilloides* (Fv-GA)) with An-GA on the Glucose Production During Standard Saccharification Experiments were performed to determine the effect of different glucoamylases blend on the glucose production when blended with the An-GA. The experiments were carried out using 33.5% ds starch liquefact and the pH of the liquefact was adjusted to pH 4.4. The starch liquefact was placed in a water bath maintained at 60° C. and enzyme(s) were added. The starch liquefact was maintained at 60° C. for 48 hrs and samples were drawn throughout the incubation to analyze the saccharide profile (shown in Table 4).

Table 4 shows the saccharide profile for treatments with different glucoamylases added at 10 µg/g ds dosage (purified glucoamylase protein) with An-GA (OPTIMAX™ L-400). Among all the glucoamylases tested, only Fv-GA was effective when blended with An-GA resulting in higher glucose to greater than 95.5% at 48 hr.

TABLE 4

Saccharide distribution for An-GA (OPTIMAX™ L-400) blends with various glucoamylase

| Sample Name | Dosage | Unit | Time, hr | Avg (% DP4+) | Avg (% DP3) | Avg (% DP2) | Avg (% DP1) |
|---|---|---|---|---|---|---|---|
| OPTIMAX™ L-400 | 120 | µg/g ds | 24 | 6.05 | 0.56 | 2.16 | 91.22 |
| | | | 41 | 2.47 | 0.44 | 2.74 | 94.36 |
| | | | 48 | 2.17 | 0.43 | 2.85 | 94.54 |
| OPTIMAX™ L-400 + An-GA | 120 + 10 | µg/g ds + µg/g ds | 24 | 5.67 | 0.54 | 2.26 | 91.53 |
| | | | 41 | 2.16 | 0.43 | 2.88 | 94.52 |
| | | | 48 | 1.79 | 0.39 | 2.95 | 94.87 |
| OPTIMAX™ L-400 + Tr-GA | 120 + 10 | µg/g ds + µg/g ds | 24 | 4.23 | 0.43 | 2.37 | 92.97 |
| | | | 43 | 1.66 | 0.41 | 3.21 | 94.72 |
| | | | 46 | 1.24 | 0.39 | 3.41 | 94.97 |
| OPTIMAX™ L-400 + Afu-GA | 120 + 10 | µg/g ds + µg/g ds | 24 | 5.19 | 0.53 | 2.22 | 92.06 |
| | | | 41 | 2.05 | 0.42 | 2.88 | 94.65 |
| | | | 48 | 1.82 | 0.42 | 3.01 | 94.75 |
| OPTIMAX L-400 + H-GA | 120 + 10 | µg/g ds + µg/g ds | 24 | 4.65 | 0.46 | 2.34 | 92.55 |
| | | | 43 | 1.71 | 0.42 | 3.09 | 94.78 |
| | | | 46 | 1.23 | 0.36 | 3.23 | 95.18 |
| OPTIMAX™ L-400 + Fv-GA | 120 + 10 | µg/g ds + µg/g ds | 24 | 4.17 | 0.56 | 2.3 | 92.98 |
| | | | 41 | 1.11 | 0.39 | 2.82 | 95.68 |
| | | | 48 | 0.97 | 0.39 | 2.93 | 95.72 |

Example 3

I. Effect of Different Glucoamylases (Purified Glucoamylases from *Trichoderma reesei* (Tr-GA), *Humicola grisea* (H-GA), *Aspergillus niger* (An-GA), and *Fusarium verticilloides* (Fv-GA)) with *A. fumigatus*-GA (Afu-GA) on Glucose Production During Standard Saccharification A set of experiments were performed to determine if different glucoamylases show similar effect with Afu-GA as they have shown when blended with An-GA (discussed in Example 2). The experiments were carried out using 33.5% ds starch liquefact and the pH of the liquefact was adjusted to pH 4.4. The starch liquefact was placed in a water bath maintained at 60° C. and enzyme(s) were added. Only purified enzyme proteins were used for these experiments so all the enzyme treatments had 0.32 SSUs of AkAA acid stable alpha amylase to match the commercial An-GA product. The starch liquefact was maintained at 60° C. for 48 hrs and samples were drawn throughout the incubation to analyze the saccharide profile (shown in Table 5).

Table 5 shows the saccharide profile for the various glucoamylase added with Afu-GA at 10 µg/g ds dosage. Similar to the observation made in Example 2 with An-GA, among all the glucoamylases tested only Fv-GA was effective when blended with Afu-GA to increase the glucose to greater than 95.5% at 48 hr. This observation shows that Fv-GA enhances the glucose production when blended with An-GA or Afu-GA, whereas other tested glucoamylases have no significant effect when blended with An-GA and Afu-GA.

TABLE 5

Saccharide distribution for Afu-GA (*A. fumigatus*-GA) blends with various glucoamylase.

| Sample Name | Dosage (µg/g ds) | Unit | Time, hr | Avg (% DP4+) | Avg (% DP3) | Avg (% DP2) | Avg (% DP1) |
|---|---|---|---|---|---|---|---|
| Afu-GA | 100 | µg/g ds | 15.5 | 11.81 | 0.58 | 3.06 | 84.56 |
|  |  |  | 24 | 6.03 | 0.48 | 2.21 | 91.27 |
|  |  |  | 43 | 2.47 | 0.43 | 2.84 | 94.26 |
|  |  |  | 46 | 1.94 | 0.4 | 2.99 | 94.68 |
| Afu-GA + Afu-GA | 100 + 10 | µg/g ds + µg/g ds | 15.5 | 11.48 | 0.49 | 3.26 | 84.77 |
|  |  |  | 24 | 5.54 | 0.51 | 2.39 | 91.56 |
|  |  |  | 43 | 2.17 | 0.42 | 3.02 | 94.39 |
|  |  |  | 46 | 1.68 | 0.4 | 3.18 | 94.73 |
| Afu-GA + Tr-GA | 100 + 10 | µg/g ds + µg/g ds | 15.5 | 10.58 | 0.53 | 2.74 | 86.14 |
|  |  |  | 24 | 5.21 | 0.53 | 2.46 | 91.79 |
|  |  |  | 43 | 1.94 | 0.43 | 3.17 | 94.46 |
|  |  |  | 46 | 1.48 | 0.4 | 3.35 | 94.77 |
| Afu-GA + An-GA | 100 + 10 | µg/g ds + µg/g ds | 15.5 | 13 | 0.51 | 4.05 | 82.45 |
|  |  |  | 24 | 5.99 | 0.52 | 2.37 | 91.12 |
|  |  |  | 43 | 2.16 | 0.38 | 2.9 | 94.56 |
|  |  |  | 46 | 1.73 | 0.38 | 3.11 | 94.78 |
| Afu-GA + H-GA | 100 + 10 | µg/g ds + µg/g ds | 15.5 | 12.64 | 0.62 | 4.23 | 82.51 |
|  |  |  | 24 | 5.75 | 0.49 | 2.33 | 91.43 |
|  |  |  | 43 | 2.28 | 0.43 | 2.92 | 94.37 |
|  |  |  | 46 | 1.64 | 0.4 | 3.08 | 94.87 |
| Afu-GA + Fv-GA | 100 + 10 | µg/g ds + µg/g ds | 15.5 | 11.28 | 0.53 | 3.38 | 84.81 |
|  |  |  | 24 | 4.84 | 0.54 | 2.37 | 92.26 |
|  |  |  | 43 | 1.53 | 0.41 | 2.88 | 95.18 |
|  |  |  | 46 | 0.86 | 0.39 | 3.04 | 95.70 |

Example 4

I. Effect of Afu-GA and Fv-GA Blend on DP1 (% Glucose)

Experiments were performed with Afu-GA, Fv-GA and a blend of Afu-GA+Fv-GA to determine the effect on % glucose produced under a typical saccharification condition. The experiments were carried out using 33.5% ds starch liquefact and the pH of the liquefact was adjusted to pH 4.4. The starch liquefact was placed in a water bath maintained at 60° C. and enzyme(s) were added. All the enzyme treatments had 0.32 SSUs of AkAA acid stable alpha amylase. The starch liquefact was maintained at 60° C. for 48 hrs and samples were drawn throughout the incubation to analyze the saccharide profile (shown in FIG. 1).

FIG. 1 shows the % glucose at the end of 48 hr for Afu-GA (80 µg/g ds), Fv-GA (80 µg/g ds) and the Afu-GA+Fv-GA (40 µg/g ds+40 µg/g ds) blend. The data in the graph shows that the blend of Afu-GA+Fv-GA is successful in achieving highest % glucose at 48 hr compared to when Afu-GA and Fv-GA are used alone at equal total glucoamylase protein dosage.

Example 5

I. Effect of Different Blend Ratios of Afu-GA and Fv-GA

Experiments were performed with different blend ratios of Afu-GA and Fv-GA to determine the optimum ratio of glucoamylases (proteins) to be used for maximum glucose production under a typical saccharification condition. The experiments were carried out using 33.5% ds starch liquefact and the pH of the liquefact was adjusted to pH 4.4. The starch liquefact was placed in a water bath maintained at 60° C. and enzyme(s) were added. Only purified enzyme proteins were used in this set of experiments so all the enzyme treatments had 0.32 SSUs of AkAA acid stable alpha amylase to match the acid stable alpha present in An-GA commercial product. The starch liquefact was maintained at 60° C. for 48 hrs and samples were drawn throughout the incubation to analyze the saccharide profile (shown in Table 6).

Table 6 shows the saccharide profile for the novel blend with different protein ratios of Afu-GA and Fv-GA. When the Afu-GA is used alone at 80 µg/g ds, it does not reach 95.5% glucose at 48 hrs. But when the Afu-GA is blended with Fv-GA at various ratios (keeping the total protein constant at 80 µg/g ds), all the blends reach >95.5% glucose at 48 hrs. Hence the blend of Afu-GA+Fv-GA at equal total glucoamylase protein resulted in the highest level of glucose production compared to Afu-GA by itself.

TABLE 6

Saccharide distribution for Afu-GA and Fv-GA blends at various protein ratios.

| Sample Name | Dosage | Unit | Time, hr | Avg (% DP4+) | Avg (% DP3) | Avg (% DP2) | Avg (% DP1) |
|---|---|---|---|---|---|---|---|
| AfuGA | 80 | µg/g ds | 18 | 10.53 | 0.57 | 2.11 | 86.8 |
| | | | 24 | 7.29 | 0.54 | 2.08 | 90.09 |
| | | | 41 | 3.31 | 0.39 | 2.43 | 93.87 |
| | | | 48 | 2.58 | 0.37 | 2.6 | 94.45 |
| AfuGA + Fv-GA | 60 + 20 | µg/g ds + µg/g ds | 18 | 8.62 | 0.63 | 2.58 | 88.17 |
| | | | 24 | 5.08 | 0.59 | 2.22 | 92.11 |
| | | | 41 | 1.72 | 0.43 | 2.37 | 95.48 |
| | | | 48 | 1.29 | 0.41 | 2.5 | 95.79 |
| AfuGA + Fv-GA | 40 + 40 | µg/g ds + µg/g ds | 18 | 8.1 | 0.65 | 3.27 | 87.99 |
| | | | 24 | 4.13 | 0.57 | 2.41 | 92.88 |
| | | | 41 | 1.44 | 0.51 | 2.35 | 95.7 |
| | | | 48 | 1.07 | 0.46 | 2.4 | 96.07 |
| AfuGA + Fv-GA | 20 + 60 | µg/g ds + µg/g ds | 18 | 6.64 | 0.64 | 3.49 | 89.23 |
| | | | 24 | 3.66 | 0.66 | 2.8 | 92.88 |
| | | | 41 | 1.42 | 0.59 | 2.48 | 95.51 |
| | | | 48 | 1.18 | 0.57 | 2.5 | 95.75 |

Figure 2:
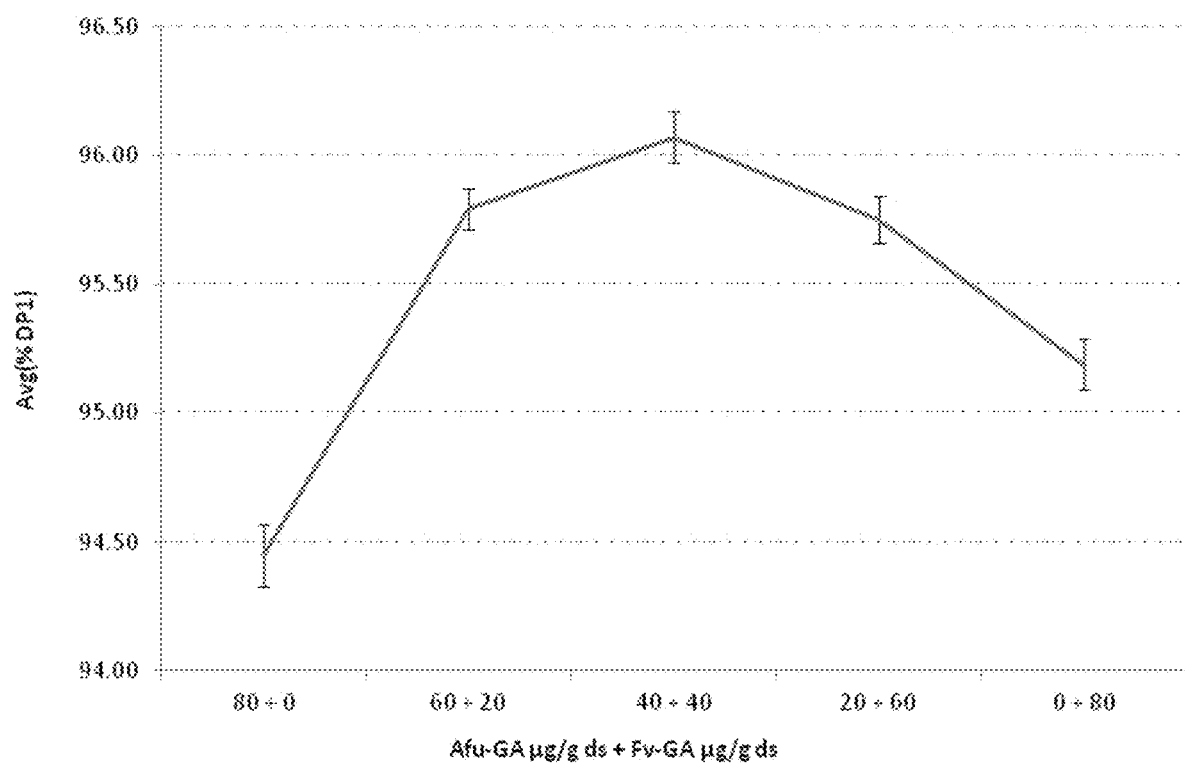
FIG. 2 is a plot based on the data of Table 6, showing the effect of the glucoamylase ratio of Afu-GA and Fv-GA on the final % glucose after 48 hr of saccharification.

FIG. 2 is a plot based on the data of Table 6, showing the effect of the glucoamylase ratio of Afu-GA and Fv-GA on the final % glucose after 48 hr of saccharification. It was found that the ideal blend, optimizing glucose yield, was the mid-level protein ratio shown as 40+40. While all the blends reach >95.5% glucose at 48 hrs, it was discovered that surprisingly, the mid-level protein ratio shown as 40+40 for Afu-GA and FV-GA reached >96% glucose at 48 hrs.

Example 6

I. Effect of Different Blend Ratios of Afu-GA and Fv-GA at Various pH Conditions A set of experiments were performed with a blend of Afu-GA+Fv-GA and compared to results for a commercial product, OPTIMAX 4060 VHP. The experiments were carried out using 33.5% ds starch liquefact and the pH of the liquefact was adjusted to pH 4.4 and/or 5.5. The starch liquefact was placed in a water bath maintained at 60° C. and enzyme(s) were added. All the enzyme treatments with non-commercial purified enzymes had 0.32 SSUs of AkAA acid stable alpha amylase to match the commercial product. The starch liquefact was maintained at 60° C. for 48 hrs and samples were drawn throughout the incubation to analyze the saccharide profile (shown in FIG. 3).

Figure 3:
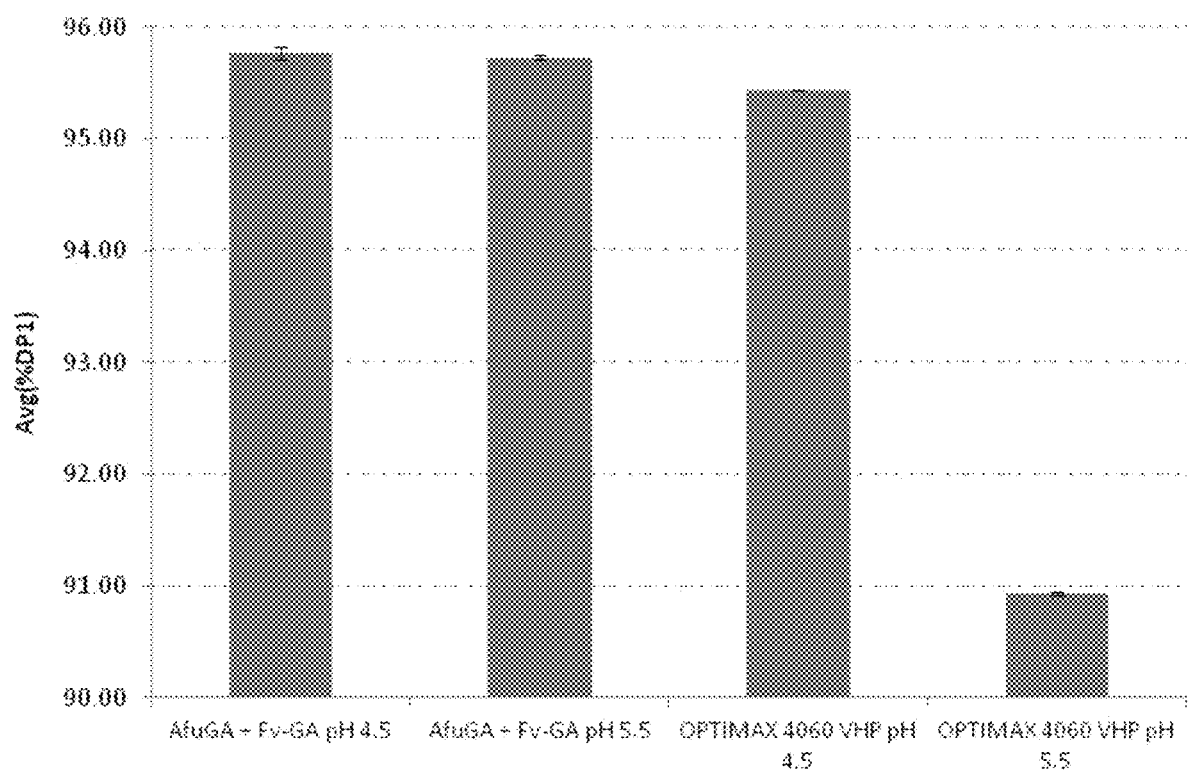
FIG. 3 shows the % glucose at 48 hr of the incubation at two different pH conditions.

FIG. 3 shows the % glucose at 48 hr of the incubation at two different pH conditions. The commercial product, OPTIMAX™ 4060 VHP, performs reasonably at pH 4.5 and produces >95.5% glucose but does not perform well at pH 5.5 and only reaches 90.93% glucose at 48 hr. The OPTIMAX™ 4060 VHP contains a *A. niger* gluco-amylase, acid stable alpha amylase and pullulanase which helps it in achieving 95.5% glucose at pH 4.5 but it suffers at elevated pH values, e.g., >5.0, as pullulanase is deactivated at higher pH values. This deactivation leads to the drop in performance of the OPTIMAX 4060 VHP product at elevated pH. The Afu-GA+Fv-GA blend maintains performance over a wide range of pH, pH 4.5 to 5.5 and consistently achieves >95.5% glucose.

Example 7

I. Effect of a De-Branching Enzyme, Pullulanase (PU), on a Range of Blend Ratios of Afu-GA and Fv-GA.

A set of experiments were performed with the commercial product OPTIMAX™ 4060 VHP as it already contains a pullulanase de-branching enzyme which helps it in achieving 95.5% glucose. Two different glucoamylases (Afu-GA and Fv-GA) were blended in addition to the standard 0.16 GAUs/g ds dosage of OPTIMAX™ 4060 VHP. The additional glucoamylases Afu-GA and Fv-GA were added at 10 µg/g ds.

Table 7 shows the saccharide profile for the OPTIMAX™ 4060 VHP and for the treatments where the additional glucoamylases Afu-GA or Fv-GA are added in addition to the standard OPTIMAX™ 4060 VHP dosage. The standard dosage of OPTIMAX™ 4060 VHP reaches the 95.52% glucose in 72 hr. The addition of glucoamylase Afu-GA does not increase the % glucose at the 72 hr saccharification time and reaches 95.6% glucose which is similar to OPTIMAX™ 4060 VHP standard dosage.

TABLE 7

Saccharide distribution for OPTIMAX ™ 4060 VHP and additional blending with the glucoamylases Afu-GA or Fv-GA.

| Sample Name | Dosage | Unit | Time, hr | Avg (% DP4+) | Avg (% DP3) | Avg (% DP2) | Avg (% DP1) |
|---|---|---|---|---|---|---|---|
| OPTIMAX ™ 4060 VHP | 0.16 | GAUs/g ds | 18 | 14.95 | 0.34 | 7.73 | 76.98 |
| | | | 24 | 10.48 | 0.38 | 5.21 | 83.93 |
| | | | 41.5 | 3.13 | 0.93 | 2.69 | 93.26 |
| | | | 49 | 2.13 | 0.87 | 2.47 | 94.53 |
| | | | 72 | 1.29 | 0.73 | 2.46 | 95.52 |
| OPTIMAX ™ 4060 VHP + | 0.16 + 10 | GAUs/g ds + µg/g ds | 18 | 12.16 | 0.72 | 4.89 | 82.23 |
| | | | 24 | 7.98 | 0.81 | 3.38 | 87.84 |

TABLE 7-continued

Saccharide distribution for OPTIMAX ™ 4060 VHP and additional blending with the glucoamylases Afu-GA or Fv-GA.

| Sample Name | Dosage | Unit | Time, hr | Avg (% DP4+) | Avg (% DP3) | Avg (% DP2) | Avg (% DP1) |
|---|---|---|---|---|---|---|---|
| AfuGA | | | 41.5 | 2.52 | 0.81 | 2.38 | 94.29 |
| | | | 49 | 1.84 | 0.74 | 2.36 | 95.05 |
| | | | 72 | 1.23 | 0.62 | 2.55 | 95.6 |
| OPTIMAX ™ 4060 VHP + Fv-GA | 0.16 + 10 | GAUs/g ds + μg/g ds | 18 | 10.01 | 0.77 | 5.12 | 84.1 |
| | | | 24 | 5.93 | 0.84 | 3.57 | 89.66 |
| | | | 41.5 | 1.26 | 0.8 | 2.3 | 95.65 |
| | | | 49 | 0.93 | 0.73 | 2.22 | 96.12 |
| | | | 72 | 0.77 | 0.61 | 2.27 | 96.35 |

Figure 4:
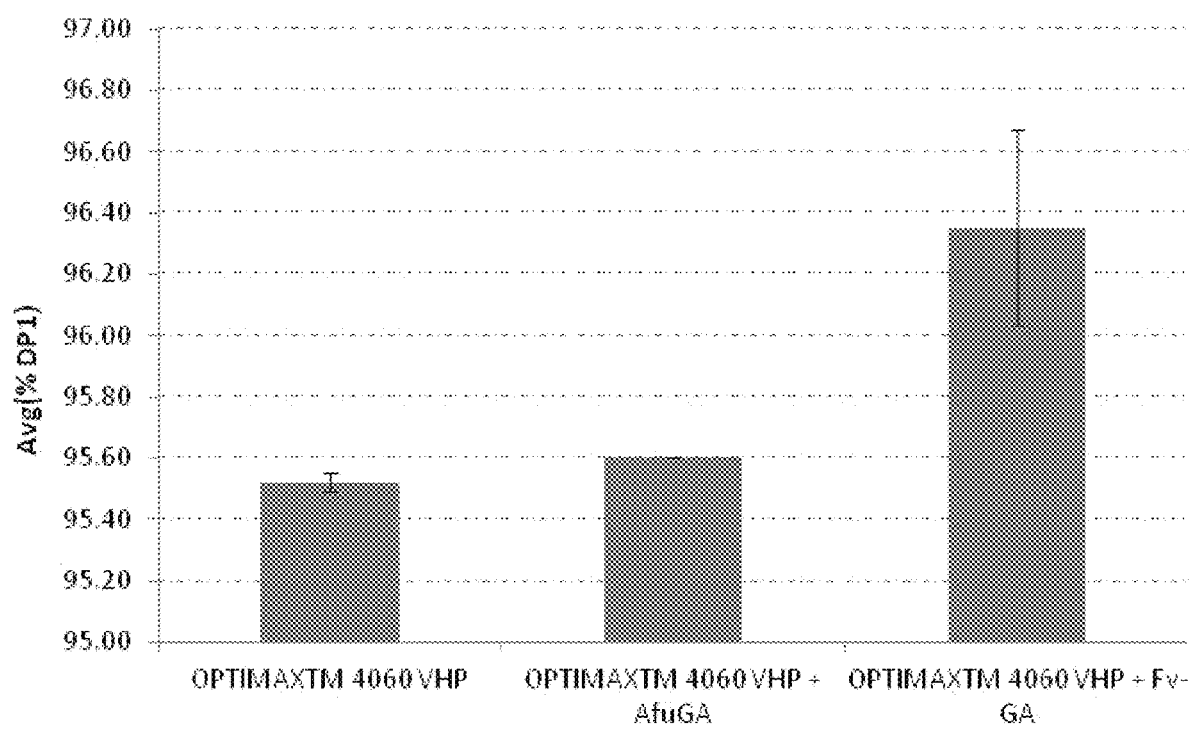
FIG. 4 which is based on the data of Table 7, shows the % glucose at 72 hr for the OPTIMAX™ 4060 VHP and additional blending with the glucoamylases Afu-GA or Fv-GA.

FIG. 4 which is based on the data of Table 7, shows the % glucose at 72 hr for the OPTIMAX™ 4060 VHP and additional blending with the glucoamylases Afu-GA or Fv-GA.

While each test condition achieved >95% glucose after 72 hrs, the combination of OPTIMAX™ 4060 VHP+Fv-GA has an unexpected improved effect of increased % glucose to 96.35%, which is significantly higher than observed for the OPTIMAX™ 4060 VHP standard dosage alone or the OPTIMAX™ 4060 VHP+Afu-GA treatment.

Example 8

I. The Effect of Fv-GA and Additional GA Blend on Simultaneous Saccharification and Fermentation (SSF) in a Corn to Ethanol Process.

A corn liquefact was obtained from a commercial fuel alcohol producer. The corn liquefact specifications were 32.84% ds and pH 3.5. The pH of the corn liquefact was adjusted to 4.5 with 4N sodium hydroxide. The experimental SSF process was carried out in replicates simultaneously in 250 ml Erlenmeyer flasks using 100 g of the liquefact per flask. The appropriate amounts of enzymes were added to the liquefact along with dry yeast and 600 ppm urea. The dry yeast is allowed to hydrate by about 10 minutes prior to addition to the flasks. The tested enzyme doses were 1) Tr-GA variant CS4 ("CS4") at 25 μg g ds and Fv-GA at 25 μg g ds; 2) CS4 GA at 50 μg g ds and 3) Fv-GA at 50 μg g ds. The flasks were covered with rubber stoppers and placed in a forced air incubator at 32° C. with shaking at 200 rpm for 54 hrs. The samples were drawn at regular intervals for ethanol measurements.

The ethanol data provided in Table 8 shows that for the blend of Fv-GA plus CS4 GA the ethanol rates were higher and the final ethanol concentrations were also highest among the compared treatments. The blend of GAs at equal total protein addition was better as compared to individual GA addition at equal total protein loading. This shows a synergistic effect of the Fv-GA with the other GA.

A similar effect was observed for the DP4+ reduction as the blend of Fv-GA plus CS4 achieved the lowest DP4+ compared to the individual GA additions at equal total protein addition.

Lower DP4+ and higher ethanol is significant for the commercial ethanol producer as this advantage translates to higher conversion of the substrate to the desired end product, e.g., ethanol.

TABLE 8

The % w/v ethanol and % w/v DP4+ distribution for the CS4 + Fv-GA blend, CS4 GA and Fv-GA showing lower % w/v DP4+ and higher % w/v ethanol for the GA blend.

| Sample Name | Dosage | Unit | Time, hr | Avg (% w/v DP4+) | StdDev (% w/v DP4+) | Avg (% w/v Ethanol) | StdDev (% w/v Ethanol) |
|---|---|---|---|---|---|---|---|
| CS4 GA + Fv-GA | 25 + 25 | μg g ds | 12 | 9.15 | 0.14 | 5.48 | 0.08 |
| | | | 28 | 4.34 | 0.05 | 10.11 | 0.02 |
| | | | 54 | 0.74 | 0.06 | 11.68 | 0.06 |
| CS4 GA | 50 | μg g ds | 12 | 8.84 | 0.06 | 5.36 | 0.19 |
| | | | 28 | 4.79 | 0.04 | 9.98 | 0.08 |
| | | | 54 | 1.03 | 0.07 | 11.46 | 0.03 |
| Fv-GA | 50 | μg g ds | 12 | 10.78 | 0.12 | 4.74 | 0.08 |
| | | | 28 | 6.21 | 0.06 | 8.72 | 0.02 |
| | | | 54 | 1.09 | 0.11 | 11.32 | 0.03 |

Figure 5:
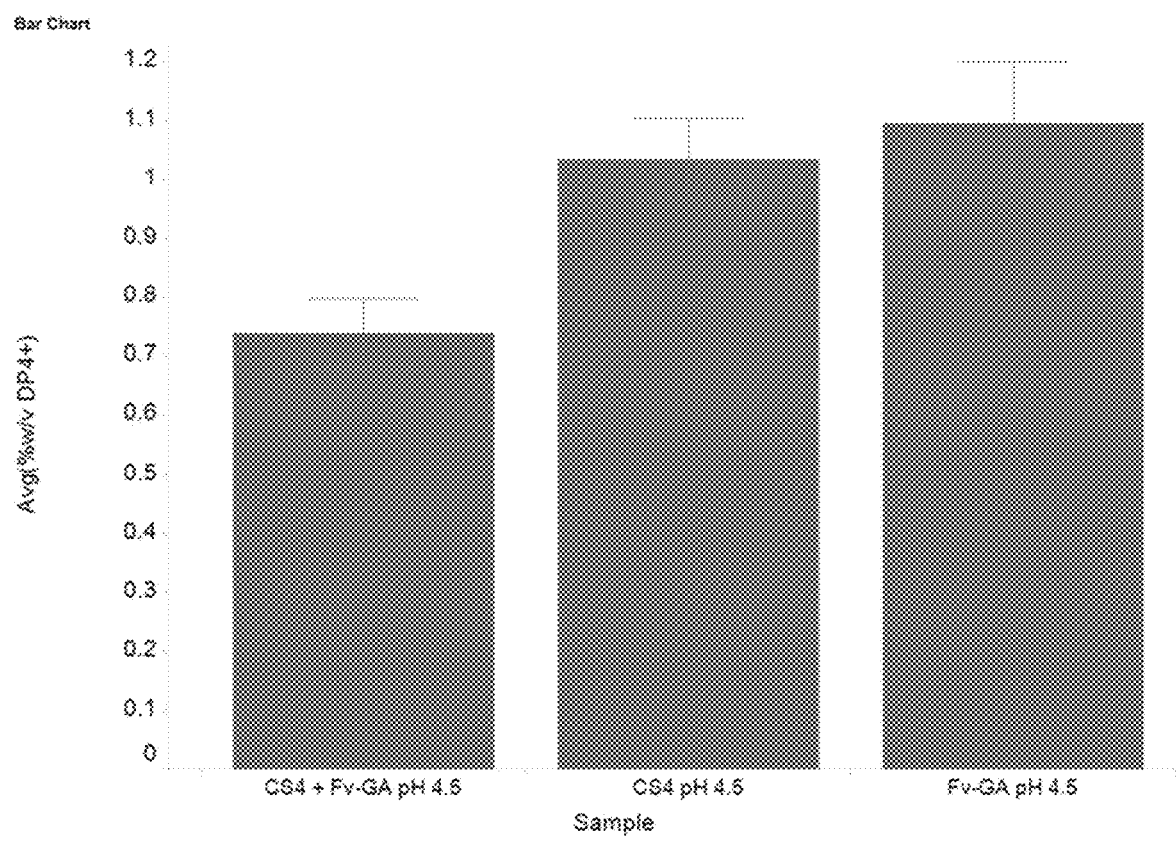
FIG. 5 shows the % w/v DP4+ at 54 hr for the CS4+Fv-GA blend, CS4 GA alone and Fv-GA alone.

FIG. 5 shows the % w/v DP4+ at 54 hr for the CS4+Fv-GA blend, CS4 GA alone and Fv-GA alone. It is clear that lower % w/v DP4+ advantageously resulted for the GA blend. As indicated in FIG. 5, about 0.3% w/v lower DP4+ resulted for the GA blend compared to either the CS4 GA or the Fv-GA alone. The CS4 GA alone reduced the DP4+ to 1.03% w/v whereas the novel GA blend reduced the DP4+ to 0.74% w/v which is a 25.2% decrease in DP4+ under similar condition. Using the blend can lead to 1.03× reduction in DP4+ under similar condition.

Figure 6:
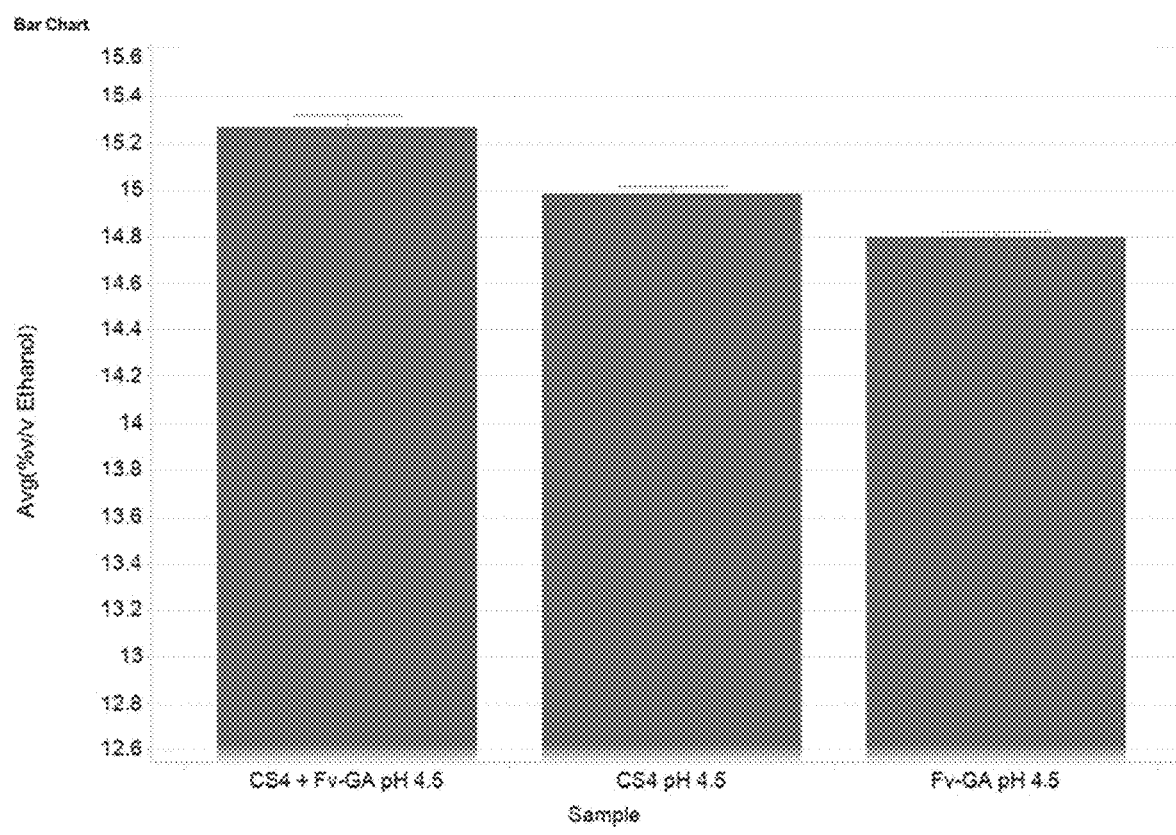
FIG. 6 shows the % w/v ethanol at 54 hr for the CS4+Fv-GA blend, CS4 GA and Fv-GA.

FIG. 6 shows the % w/v ethanol at 54 hr for the CS4+Fv-GA blend, CS4 GA and Fv-GA, wherein higher % w/v ethanol resulted for the GA blend. As indicated, the % w/v ethanol was about 0.2% higher for the GA blend compared to either the CS4 GA or the Fv-GA alone. The CS4 GA alone reached the ethanol content of 14.98% v/v whereas the novel GA blend reached the ethanol content of 15.26% v/v which is an overall 1.86% increase in ethanol production over the CS4 GA alone under similar condition. Using the blend can lead to 1.018× increase in ethanol production under similar condition.

Example 9

I. The Effect of Fv-GA and an Additional GA Blend on Saccharification Under Biochemical Fermentation Conditions of pH 7.0 and at 37° C.

Experiments were performed with Afu-GA, HGA, TrGA, Fv-GA and a blend of HGA+Fv-GA to determine the effect of individual GA enzymes and GA blends on final % glucose. The experiments were carried out using 33.5% ds starch liquefact and the pH of the liquefact was adjusted to pH 7.0. The starch liquefact was placed in a water bath maintained at 37° C. and enzyme(s) were added. The starch liquefact was maintained at 37° C. for 72 hrs and samples were drawn throughout the incubation to analyze the saccharide profile.

The data in Table 9 shows that the Fv-GA at 80 μg/g ds was much faster and achieved highest final % glucose compared to other GAs (also added at 80 μg/g ds). Also, Fv-GA added at 80 μg/g ds was slightly better compared to HGA at 160 μg/g ds.

The data also shows that the blend of Fv-GA at 40 μg/g ds and HGA 160 μg/g ds is better when compared to HGA at 320 μg/g ds (Table 10). This shows a significant and unexpected synergy between Fv-GA and HGA. The blend of Fv-GA and HGA (total protein addition of 200 μg/g ds, with Fv-GA at 40 μg/g ds and HGA 160 μg/g ds) reaches lower amount of DP4+ and highest amount of % DP1 compared to HGA even at 320 μg/g ds.

TABLE 9

Saccharide distribution for Afu-GA, Fv-GA, HGA, and TrGA at 80 μg/g ds protein dosage during saccharification under biochemical fermentation conditions of 37° C. and pH 7.0

| Sample Name | Dosage | Unit | Time, hr | Avg (% DP4+) | Avg (% DP3) | Avg (% DP2) | Avg (% DP1) |
|---|---|---|---|---|---|---|---|
| AfuGA | 80 | μg/g ds | 20 | 48.85 | 4.42 | 8.46 | 38.27 |
|  |  |  | 50 | 23.49 | 0.56 | 2.03 | 73.92 |
|  |  |  | 72 | 18.04 | 0.62 | 1.4 | 79.94 |
| Fv-GA | 80 | μg/g ds | 20 | 33.53 | 2.27 | 8.11 | 56.08 |
|  |  |  | 50 | 13.38 | 0.61 | 2.27 | 83.73 |
|  |  |  | 72 | 6.69 | 0.63 | 1.96 | 90.72 |
| HGA | 80 | μg/g ds | 17 | 50.61 | 6.25 | 8.86 | 34.28 |
|  |  |  | 48 | 23.18 | 0.66 | 4.06 | 72.09 |
|  |  |  | 72 | 16.62 | 0.69 | 1.83 | 80.86 |
| HGA | 160 | μg/g ds | 20 | 43.44 | 3.02 | 8.14 | 45.4 |
|  |  |  | 42 | 17.24 | 0.73 | 2.12 | 79.9 |
|  |  |  | 72 | 8.62 | 0.53 | 2.14 | 88.71 |
| TrGA | 80 | μg/g ds | 20 | 35.17 | 1.26 | 7.36 | 56.2 |
|  |  |  | 50 | 20.99 | 0.65 | 1.79 | 76.57 |
|  |  |  | 72 | 16.7 | 0.52 | 2.06 | 80.73 |

TABLE 10

Saccharide distribution for Fv-GA + HGA blend and HGA at higher dosages showing the blend of Fv-GA plus HGA performs better compared to HGA at higher dosage during saccharification under biochemical fermentation conditions of 37° C. and pH 7.0

| Sample Name | Dosage | Unit | Time, hr | Avg (% DP4+) | Avg (% DP3) | Avg (% DP2) | Avg (% DP1) |
|---|---|---|---|---|---|---|---|
| Fv-GA + HGA | 40 + 160 | μg/g ds | 20 | 19.4 | 0.56 | 3.97 | 76.07 |
|  |  |  | 50 | 3.57 | 0.64 | 2.09 | 93.7 |
|  |  |  | 72 | 2.43 | 0.59 | 2.76 | 94.22 |
| HGA | 160 | μg/g ds | 20 | 43.44 | 3.02 | 8.14 | 45.4 |
|  |  |  | 50 | 14.18 | 0.67 | 1.76 | 83.39 |
|  |  |  | 72 | 8.62 | 0.53 | 2.14 | 88.71 |
| HGA | 320 | μg/g ds | 20 | 27.18 | 1.43 | 5.96 | 65.42 |
|  |  |  | 50 | 5.88 | 0.44 | 2.2 | 91.48 |
|  |  |  | 72 | 3.61 | 0.45 | 3.21 | 92.73 |

Example 10

I. The Effect of Fv-GA and an Additional GA Blend on the Direct Starch to Glucose (DSTG) Process.

Experiments were performed with Afu-GA, Fv-GA and a blend of Afu-GA+Fv-GA to determine the effect of the enzyme and enzyme blends on final % solubility and % glucose. The experiments were carried out using 32% ds raw tapioca starch and the pH of the tapioca starch slurry was left as is as at pH 5.2. The enzymes were added as such 1) Afu-GA at 80 µg/g ds 2) Afu-GA at 40 µg/g ds+Fv-GA at 40 µg/g ds and 3) Fv-GA at 80 µg/g ds. All the treatments also included 10 AAUs of the alpha-amylase product SPEZYME Xtra® (DuPont). The slurry was mixed at room temperature to blend the added enzymes. A 35 g aliquot with 2 replications for each treatment was weighed into LABOMAT steel beakers. The metal beakers were fitted back into the LABOMAT for incubation at 60 C for 72 hrs with clockwise and counter-clockwise constant mixing at 60 rpm. Samples were drawn throughout the incubation to analyze the saccharide profile.

The data in Table 11 shows that the blend of Fv-GA plus Afu-GA achieves % solubility of 96.51 in 72 hrs and the individually added Afu-G or Fv-GA achieve 93.05 and 94.89% solubility, respectively. Also, the % DP1 and % DP4+ values for the blend of Fv-GA and Afu-GA were 96.51% and 0.71%, respectively. This shows that the blend of Fv-GA plus Afu-GA unexpectedly achieved the lowest amount of DP4+ and highest amount of % DP1 compared to the individually added Afu-GA or Fv-GA.

TABLE 11

Saccharide distribution and % solubility for AfuGA, Fv-GA + Afu-GA blend and Fv-GA showing the blend of Fv-GA plus AfuGA performs better compared to individually added Afu-GA and Fv-GA during DSTG of tapioca starch at 60° C. and pH 5.2

| Sample Name | Dosage | Unit | Time, hr | Avg (% DP4+) | Avg (% DP3) | Avg (% DP2) | Avg (% DP1) | Avg (% Solubility) |
|---|---|---|---|---|---|---|---|---|
| Afu-GA | 80 | µg/g ds | 24 | 5.49 | 2.16 | 2.55 | 89.8 | 83.9 |
|  |  |  | 48 | 3.65 | 1.87 | 2.45 | 92.03 | 92.14 |
|  |  |  | 72 | 1.95 | 1.69 | 2.31 | 94.06 | 93.05 |
| Afu-GA + Fv-GA | 40 + 40 | µg/g ds | 24 | 2.4 | 1.63 | 2.49 | 93.48 | 86.31 |
|  |  |  | 48 | 1 | 1.21 | 2.21 | 95.58 | 95.12 |
|  |  |  | 72 | 0.71 | 1.07 | 2.69 | 95.53 | 96.51 |
| Fv-GA | 80 | µg/g ds | 24 | 2.93 | 1.46 | 2.66 | 92.95 | 85.65 |
|  |  |  | 48 | 1.86 | 1.14 | 3.01 | 93.99 | 93.74 |
|  |  |  | 72 | 1.36 | 1.11 | 3.67 | 93.85 | 94.89 |

```
SEQUENCE LISTING

SEQ ID NO: 1
Fv-GA Protein Sequence:
MFTQILYGLTALSALQGQVTASPGGSSLDRFISKEADISIKGVLANIGADGKRAQGAAPGAVVASPSRTD
PDYWYTWTRDSALTYKVLVERFIHGDKSLQRKIDEYVSAQAKLQGVTNPSGGPESGGLGEPKFHVNLTAF
TGSWGRPQRDGPPLRATALTLYANWLVSHGDRSKAVNKVWPVIEKDLAYTVKFWNRTGYDLWEEVNGSSF
FTLSASHRALVEGAALAKKLGKSCSDCATNAPRVLCFMQSFWTGSYIDSNINVNDGRKGLDANSILSSIH
TFDPSSKCTDSTFQPCSSRALANHKEVVDSFRSIYGVNKNRGKGKAAAVGRYSEDVYYDGNPWYLATLAA
AEQLYAAVYQWNKIGSITVDSVSLPFFSDLVPKVSKGTYRKNSKTYKAIIKAVTSYADGFVAVVQTYTPK
DGSLAEQFDKSTGTPKSAVHLTWSYASFVGAAERRTGVVPPAWGESNANKVPAVCEAAPACDTTITFNVK
NVDVTSDQKVYIVGGITQLSNWAPADGIALEESTSTKGLWTVKVKIPSDTSFEYKYIKKTSDGTVTWESD
PNNSAATGSKCGSSSTINDEWR SEQ ID NO: 2
Fv-GA DNA Nucleotide Sequence:
ATGTTTACTCAGATCTTGTATGGCCTCACGGCCTTATCTGCCCTCCAAGGTCAGGTCACTGCATCACCAG
GCGGTTCCAGCCTTGATCGCTTCATTTCCAAAGAGGCCGACATCTCCATCAAGGGCGTGCTTGCCAATAT
TGGCGCCGATGGCAAGCGAGCCCAAGGCGCTGCACCTGGCGCCGTTGTAGCAAGTCCATCGAGAACAGAT
CCAGACTGTAAGTCAATATTCTTGATAGTATCGCAAATGGATGACTGAGACGTTTTCTAGACTGGTACAC
ATGGACCCGAGACTCCGCCTTGACATACAAAGTCCTTGTTGAGCGCTTCATTCACGGAGACAAGTCTCTC
CAGCGCAAGATCGACGAATATGTCTCTGCCCAAGCCAAGCTCCAGGGCGTCACCAACCCATCTGGCGGCC
CCGAGTCAGGCGGCCTTGGGGAACCCAAGTTTCACGTCAACCTCACAGCTTTCACAGGATCCTGGGTCG
TCCTCAACGAGATGGCCCTCCTCTGAGAGCTACTGCATTGACGCTGTACGCCAACTGGCTTGTTTCTCAC
GGCGACCGCTCCAAGGCCGTCAACAAGGTTTGGCCTGTCATTGAGAAGGATCTTGCATACACCGTCAAGT
TCTGGAACAGAACCGGTTACGATCTTTGGGAGGAGGTTAACGGATCTTCGTTCTTCACCCTCTCTGCTTC
ACATCGTGCTCTGGTTGAGGGAGCTGCTCTTGCTAAGAAGCTTGGCAAGTCTTGCTCCGACTGCGCAACC
AACGCCCCCCGTGTTCTCTGCTTCATGCAAAGCTTCTGGACCGGCAGCTACATCGACTCGAACATCAATG
TCAACGATGGCCGCAAGGGTCTTGATGCCAACTCCATTCTGTCTTCTATTCACACCTTTGATCCTTCTTC
GAAGTGCACAGACTCTACCTTCCAGCCTTGTTCTTCAAGGGCTCTTGCGAACCACAAGGAAGTAGTGGAC
TCTTTCCGCTCCATCTATGGTGTCAACAAAAACAGAGGTAAAGGTAAAGCTGCTGCTGTCGTCGATACA
GTGAGGATGTGTACTACGACGGTAACCCTTGGTACTTGGCTACTCTTGCTGCTGCCGAGCAACTGTACGC
TGCTGTCTATCAATGGAACAAGATCGGTTCCATCACAGTTGATAGTGTGTCGCTCCCCTTTTTCAGTGAC
CTTGTACCAAAGGTTTCCAAGGGAACCTATCGCAAGAACAGCAAGACATACAAGGCTATTATCAAGGCTG
TCACTTCATACGCTGATGGCTTTGTCGCCGTTGTGCAGACCTATACTCCCAAAGATGGCTCCCTCGCAGA
GCAGTTCGATAAGTCTACTGGAACTCCCAAGTCAGCTGTTCACCTAACCTGGTCCTACGCCTCCTTTGTC
GGTGCTGCCGAGCGTCGTACTGGCGTCGTTCCTCCAGCTTGGGGCGAGAGCAACGCCAACAAGGTGCCTG
CTGTTTGCGAAGCAGCTCCAGCCTGCGACACCACCATCACGTTCAATGTGAAGAACGTTGATGTCACGTC
GGACCAGAAGGTTTACATTGTTGGCGGGATCACTCAACTTTCCAACTGGGCCCCTGCTGACGGCATTGCG
CTTGAGGAATCCACGAGCACCAAGGGCTTGTGGACTGTGAAGGTCAAGATTCCATCTGATACCAGCTTTG
```

SEQUENCE LISTING

```
AGTATAAGTATATAAAGAAGACGAGTGATGGAACTGTTACATGGGAGAGTGACCCCAATAACAGTGCGGC
GACGGGCAGCAAGTGCGGAAGCAGCAGTACCATCAACGATGAGTGGAGGTAA
```

SEQ ID NO: 3
Afu-GA Protein Sequence:
```
MPRLSYALCALSLGHAAIAAPQLSARATGSLDSWLGTETTVALNGILANIGADGAYAKSAKPGIIIASPS
TSEPDYYYTWTRDAALVTKVLVDLFRNGNLGLQKVITEYVNSQAYLQTVSNPSGGLASGGLAEPKYNVDM
TAFTGAWGRPQRDGPALRATALIDFGNWLIDNGYSSYAVNNIWPIVRNDLSYVSQYWSQSGFDLWEEVNS
MSFFTVAVQHRALVEGSTFAKRVGASCSWCDSQAPQILCYMQSFWTGSYINANTGGGRSGKDANTVLASI
HTFDPEAGCDDTTFQPCSPRALANHKVYTDSFRSVYAINSGIPQGAAVSAGRYPEDVYYNGNPWFLTTLA
AAEQLYDAIYQWKKIGSISITSTSLAFFKDIYSSAAVGTYASSTSTFTDIINAVKTYADGYVSIVQAHAM
NNGSLSEQFDKSSGLSLSARDLTWSYAAFLTANMRRNGVVPAPWGAASANSVPSSCSMGSATGTYSTATA
TSWPSTLTSGSPGSTTTVGTTTSTTSGTAAETACATPTAVAVTFNEIATTTYGENVYIVGSISELGNWDT
SKAVALSASKYTSSNNLWYVSVTLPAGTTFEYKYIRKESDGSIVWESDPNRSYTVPAACGVSTATENDTW
Q
```

SEQ ID NO: 4
Afu-GA Nucleotide Sequence:
```
atgcctcgcctttcctacgcgctctgtgcgctgtctctcgggcatgctgctattgcagctcctcagttat
ccgctcgtgctaccggcagcttggactcctggttgggtactgagcaaccccgttcgcgctcaatggtattct
ggccaacatcggtgccgacggtgcttatgcgaagagcgctaagcctggcataatcattgccagtccgagc
accagcgaaccagactgtgagaaccttcctgaactggccctgtccggcagtcattgacctcggtagacta
ctataccttggacgagagatgctgctctcgtcacgaaagtcctggtcgacctcttccgcaacggcaacctg
ggtctgcagaaagtcattaccgaatacgtcaactctcaggcgtacttgcagaccgtgtctaatccgtcgg
gtggtcttgcgagcggaggtctcgcggagcctaagtacaacgtcgacatgacggcctttaccggagcctg
gggtcgtcctcagcgtgatggtccggctctgcgggcaccgccctcatcgactttggcaactggctgatt
gtatgttctccatacgagcccaggaagcgttgctgacgtctacaggacaacggctactccagctatgct
gtcaacaacatctggcccattgtgcgcaacgacttgtcctacgtttctcagtactggagccagagtggct
ttggtgagtcccgactctctggaagtttacaacgtcgatcgattactgacaattgagattctacgtgaca
gatctctgggaagaagtcaactccatgtccttcttcaccgtcgctgtccagcaccgtgccctcgtggagg
gaagcacgttcgctaaacgggtgggagcgtcgtgctcgtggtgtgactcgcaggcccccagatcctctg
ctacatgcagagtttctggactggctcgtatatcaacgccaacaccggtggtggccggtccggcaaggat
gccaacaccgtcctcgccagcatccataccttcgaccccgaagccggctgcgacgatactacttccagc
cctgctctcctcgggccttgccaaccacaaggtgtacaccgattcgttccgctcggtctacgcgatcaa
ctccggcatcccacagggcgctgccgtttccgctggccgctaccccgaggacgtctactacaacggcaac
ccttggttcctcaccaccctcgccgctgccgagcagctctacgacgctatctaccagtggaagaagatcg
gttccatcagcatcaccagcaccctccctcgccttcttcaaggacatctacagctccgccggtcggcac
ctacgcctagcacctccaccttcacggacatcatcaacgcggtcaagacctacgcagacggctacgtg
agcatcgtccaggcacacgccatgaacaacggctccctttcggagcaattcgacaagtcctctgggctgt
ccctctccgcccgcgatctgacctggtcctacgccgctttcctcaccgccaacatgcgtcgtaacggcgt
ggtgcctgcccctgggcgccgcctccgccaactccgtccccctcgtcttgctccatgggctcggccacg
ggcacctacgcaccgcgacagccaccctcctggcccagcacgctgaccagcggctcgcaggcagcacca
ccaccgtgggcaccacgaccagtaccacctctggcaccgccgccgagaccgcctgtgcgaccctaccgc
cgtggccgtcacctttaacgagatcgccaccaccacctacggcgagaatgtttacattgttgggtccatc
tccgagctcgggaactgggataccagcaaagcagtggccctgagtgcgtccaagtataacctccagcaata
acctctggtacgtgtccgtcaccctgccggctggcacgacattcgagtacaagtatatccgcaaggaaag
cgatggctcgatcgtgtgggagagtgaccccaaccgctcgtatacggtgccggcagcttgtggagtgtct
actgcgaccgagaatgatacttggcagtga
```

SEQ ID NO: 5
Hg-GA Protein Sequence:
```
MHTFSKLLVLGSAVQSALGRPHGSSRLQERAAVDTFINTEKPIAWNKLLANIGPNGKAAPGAAAGVVIAS
PSRTDPPYFFTWTPDAALVLTGIIESLGHNYNTTLQTVIQNYVASQAKLQQVSNPSGTFADGSGLGEAKF
NVDLTAFTGEWGRPQRDGPPLRAIALIQYAKWLIANGYKSTAKSVVWPVVKNDLAYTAQYWNETGFDLWE
EVPGSSFETIASSHRALTEGAYLAAQLDTECPPCTIVAPQVLCFQQAFWNSKGNYVVSTSTAGEYRSGKD
ANSILASIHNFDPEAGCDNLIFQPCSERALANHKAYVDSFRNLYAINKGIAQGKAVAVGRYSEDVYYNGN
PWYLANFAAAEQLYDAIYVWNKQGSITVTSVSLPFFRDLVSSVSTGTYSKSSSTFTNIVNAVKAYADGFI
EVAAKYTPSNGALAEQYDRNIGKPDSAADLTWSYSAFLSAIDRRAGLVPPSWRASVAKSQLPSTCSRIEV
AGTYVAATSTSFPSKQTPNPSAAPSPSPYPTACADASEVYVTFNERVSTAWGETIKVVGNVPALGNWDTS
KAVTLSASGYKSNDPLWSITVPIKATGSAVQYKYIKVGTNGKITWESDPNRSITLQTASSAGKCAAQTVN
DSWR
```

SEQ ID NO: 6
Hg-GA Nucleotide Sequence:
```
atgcatacctctctccaagctcctcgtcctgggctctgccgtccagtctgccctcgggcggcctcacggct
cttcgcgtctccaggaacgcgctgccgttgataccttcatcaacaccgagaagcccatcgcatggaacaa
gctgctcgccaacatcggccctaacggcaaagccgctcccggtgccgccgccggcgttgtgattgccagc
ccttccaggacggaccctcttgtacgtggtggcatggaatggacccaagagactgttttagatgaaaga
gagtttctgctaaccgccacacccagacttcttcacctggacccggatgccgccctggtcctcaccggc
atcatcgagtcccttggccacaactacaacaccacccctgcagaccgtcatccagaactacgtcgcgtcgc
aggcaagctgcagcaggtctcgaaccctcgggaaccttcgccgacggctcgggtctcggtgaggccaa
gttcaatgtcgacctcactgccttcactggcgaatggggtcgcccagaggacggcccgcccctcgcgc
gccatcgctctcatccagtacgccaagtggctgatcgccaacggctacaagagcacgccaagagcgtcg
tctggccgtcgtcaagaacgatctcgcctacacggcccagtactggaacgagaccggcttcgatctctg
ggaggagtcccggcagctcgttcttttaccatcgccagctctcacagggtgagtcatttattgttcag
tgttttctcattgaataattaccggaatgccactgacgccaaacagctctgactgagggtgcttacctcg
ccgctcagctcgacaccgagtgccgccctgcacgaccgtcgcccctcaggttctgtgcttccagcaggc
```

-continued

```
SEQUENCE LISTING cttctggaactccaagggcaactatgtcgtctcaacagtaagatccctacaccaacaaaaaaatcgaaa
aggaacgttagctgaccttctagtcaacggcggcgagtatcgctccggcaaggacgccaactcgatcc
tggcgtccatccacaacttcgaccctgaggccgctgcgacaacctgaccttccagccctgcagcgacg
cgccctggccaaccacaaggcctatgtcgactcgttccgcaacctctacgccatcaacaagggcatcgcc
cagggcaaggccgttgccgtcggccgctactcggaggatgtctactacaacggcaacccgtggtacctgg
ccaactttgccgccgccgagcagctctacgacgccatctacgtgtggaacaagcagggctccatcaccgt
gacctcggtctccctgcccttcttccgcgacctttgtctcgtcggtcagcaccggcacctactccaagagc
agctcgaccttcaccaacatcgtcaacgccgtcaaggcctacgccgacggcttcatcgaggtggccgcca
agtacaccccgtccaacggcgcgctcgccgagcagtacgaccgcaacacgggcaagcccgactcggccgc
cgacctgacgtggtcgtactcggccttcctctcggccatcgaccgccgcgggtctcgtcccccgagc
tggcgggccagcgtggccaagagccagctgccgtccacctgctcgcgcatcgaggtcgccggcacctacg
tcgccgccacgagcacctcgttcccgtccaagcagaccccgaacccctccgcggcgccctccccgtcccc
ctacccgaccgcctgcgcggacgctagcgaggtgtacgtcaccttcaacgagcgcgtgtcgaccgcgtgg
ggcgagaccatcaaggtggtgggcaacgtgccggcgctggggaactgggacacgtccaaggcggtgaccc
tgtcggccagcgggtacaagtcgaatgatcccctctggagcatcacggtgcccatcaaggcgacgggctc
ggccgtgcagtacaagtatatcaaggtcggcaccaacgggaagattacttgggagtcggaccccaacagg
agcattaccctgcagacggcgtcgtctgcgggcaagtgcgccgcgcagacggtgaatgattcgtggcgtt
aa SEQ ID NO: 7
An-GA Protein Sequence:
MSFRSLLALSGLVCTGLANVISKRATWDSWLSNEATVARTAILNNIGADGAWVSGADSGIVVASPSTDNP
DYFYTWTRDSGLVLKTLVDLFRNGDTSLLSTIENYISAQAIVQGISNPSGDLSSGAGLGEPKFNVDETAY
TGSWGRPQRDGPALRATAMIGFGQWLLDNGYTSTATDIVWPLVRNDLSYVAQYWNQTGYDLWEVNGSSFF
TIAVQHRALVEGSAFATAVGSSCSMCDSQAPEILCYLQSFWIGSFILANFDSSRSAKDANTLLLGSIHTF
DPEAACDDSTFQPCSPRALANHKEVVDSFRSIYILNDGLSDSEAVAVGRYPEDTYYNGNPWFLCTLAAAE
QLYDALYQWDKQGSLEVTDVSLDFFKALYSDATGTYSSSSSTYSSIVDAVKTFADGFVSIVETHAASNGS
MSEQYDKSDGEQLSARDLTWSYAALLTANNRRNVVPSASWGETSASSVPGTCAATSAIGTYSSVTVTSWP
SIVATGGTTTTATPTGSGSVTSTSKTTATASKTSTSTSSTSCTTPTAVAVTFDLTATTTYGENTYLVGSI
SQLGDWETSDGIALSADKYTSSDPLWYVTVTLPAGESFEYKFIRIESDDSVEWESDPNREYTVPQACGTS
TATVTDTWR SEQ ID NO: 8
An-GA Nucleotide Sequence:
atgtcgttccgatctctactcgccctgagcggcctcgtctgcacagggttggcaaatgtgatttccaagc
gcgcgacctgggattcatggttgagcaacgaagcgaccgtggctcgtactgccatcctgaataacatcgg
ggcggacggtgcttgggtgtcgggcgcggactctggcattgtcgttgctagtcccagcacggataacccg
gactacttctacacctggactcgcgactctggtctcgtcctcaagaccctcgtgatctcttccgaaatg
gagataccagtctcctctccaccattgagaactacatctccgcccaggcaattgtccagggtatcagtaa
cccctctggtgatcgtccagcggcgctggtctcggtgaacccaagttcaatgtcgatgagactgcctac
actggttcttggggacggccgcagcgagatggtccggctctgagagcaactgctatgatcggcttcgggc
aatggctgcttgacaatggctacaccagcaccgcaacggacattgtttggccccctcgttaggaacgacct
gtcgtatgtggctcaatactggaaccagacaggatatgatctctgtggaagtcaatggctcgtcttttctt
acgattgctgtgcaacaccgcgcccttgtcgaaggtagtgccttcgcgacggccgtcggctcgtcctgct
cctggtgtgattctcaggcacccgaaattctctgctacctgcagtccttctggaccggcagcttcattct
ggccaacttcgatagcagccgttccgccaaggacgcaaacacccctcctgctgggaagcatccacacccttt
gatcctgaggccgcatgcgacgactccaccttccagccctgctccccgcgcgcgctcgccaaccacaagg
aggttgtagactcttttccgctcaatctataccctcaacgatggtctcagtgacagcgaggctgttgcggt
gggtcggtaccctgaggacacgtactacaacggcaacccgtggttcctgtgcaccttggctgccgcagag
cagttgtacgatgctctataccagtgggacaagcaggggtcgttggaggtcacagatgtgtcgctggact
tcttcaaggcactgtacagcgatgctactggcacctactcttcgtccagttcgacttatagtagcattgt
agatgccgtgaagactttcgccgatggcttcgtctctattgtggaaactcacgccgcaagcaacggctcc
atgtccgagcaatacgacaagtctgatggcgagcagctttccgctcgacttgacctggtcttatgctg
ctctgctgaccgccaacaaccgtcgtaacgtcgtgccttccgcttcttggggcgagacctctgccagcag
cgtgccggcacctgtgcggcacatctgccattggtacctacagcagtgtgactgtcacctcgtgccg
agtatcgtggctactggcggcaccactacgacggctaccccactggatccggcagcgtgacctcgacca
gcaagaccaccgcgactgctagcaagaccagcaccagtacgtcatcaacctcctgtaccactcccaccgc
cgtggctgtgacttttcgatctgacagctaccaccaccctacggcgagaacatctacctggtcggatcgatc
tctcagctgggtgactgggaaaccagcgacggcatagctctgagtgctgacaagtacacttccagcgacc
cgctctggtatgtcactgtgactctgccggctggtgagtcgtttgagtacaagtttatccgcattgagag
cgatgactccgtggagtgggagagtgatcccaaccgagaatacaccgttcctcaggcgtgcggaacgtcg
accgcgacggtgactgacacctggcggtag SEQ ID NO: 9
Tr-GA variant C54 Mature Protein Sequence:
SVDDFISTETPIALNNLLCNVGPDGCRAFGTSAGAVIASPSTIDPDYYYMWTRDSALVFKNLIDRFTETY
DAGLQRRIEQYITAQVTLQGLSNPSGSLADGSGLGEPKFELTLKPFTGNWGRPQRDGPALRAIALIGYSK
WLINNNYQSTVSNVIWPIVRNDLNYVAQYWNQTGFDLWEEVNGSSFFTVANQHRALVEGATLAATLGQSG
SAYSSVAPQVLCFLQRFWVSSGGYVDSNINTNEGRIGKDVNSVLISIHTFDPNLGCDAGTFQPCSDKALS
NLKVVVDSFRSIYGVNKGIPAGAAVAIGRYAEDVYYNGNPWYLATFAAAEQLYDAIYVWKKTGSITVTAT
SLAFFQELVPGVTAGTYSSSSSTFTNIINAVSTYADGFLSEAAKYVPADGSLAEQFDRNSGTPLSAVHLT
WSYASFLTAAARRAGIVPPSWANSSASTIPSTCSGASVVGSYSRPTATSFPPSQTPKPGVPSGTPYTPLP
CATPTSVAVTFHELVSTQFGHTVKVAGNAAALGNWSTSAAVALDAVNYRDNHPLWIGTVNLEAGDVVEYK
YIIVGQDGSVTWESDPNHTYTVPAVACVTQVVKEDTWQS
```

```
SEQ ID NO: 10
Tr-GA Mature Protein Sequence:
SVDDFISTETPIALNNLLCNVGPDGCRAFGTSAGAVIASPSTIDPDYYYMWTRDSALVFKNLIDRFTETY
DAGLQRRIEQYITAQVTLQGLSNPSGSLADGSGLGEPKFELTLKPFTGNWGRPQRDGPALRAIALIGYSK
WLINNNYQSTVSNVIWPIVRNDLNYVAQYWNQTGFDLWEEVNGSSFFTVANQHRALVEGATLAATLGQSG
SAYSSVAPQVLCFLQRFWVSSGGYVDSNINTNEGRIGKDVNSVLISIHTFDPNLGCDAGTFQPCSDKALS
NLKVVVDSFRSIYGVNKGIPAGAAVAIGRYAEDVYYNGNPWYLATFAAAEQLYDAIYVWKKTGSITVTAT
SLAFFQELVPGVTAGTYSSSSSTFTNIINAVSTYADGFLSEAAKYVPADGSLAEQFDRNSGTPLSALHLT
WSYASFLTATARRAGIVPPSWANSSASTIPSTCSGASVVGSYSRPTATSFPPSQTPKPGVPSGTPYTPLP
CATPTSVAVTFHELVSTQFGQTVKVAGNAAALGNWSTSAAVALDAVNYADNHPLWIGTVNLEAGDVVEYK
YINVGQDGSVTWESDPNHTYTVPAVACVTQVVKEDTWQS SEQ ID NO: 11
Tr-GA Parent Protein Sequence(632 amino acids):
  1         MHVLSTAVLL GSVAVQKVLG RPGSSGLSDV TKRSVDDFIS TETPIALNNL

51         LCNVGPDGCR AFGTSAGAVI ASPSTIDPDY YYMWTRDSAL VFKNLIDRFT

101         ETYDAGLQRR IEQYITAQVT LQGLSNPSGS LADGSGLGEP KFELTLKPFT

151         GNWGRPQRDG PALRAIALIG YSKWLINNNY QSTVSNVIWP IVRNDLNYVA

201         QYWNQTGFDL WEEVNGSSFF TVANQHRALV EGATLAATLG QSGSAYSSVA

251         PQVLCFLQRF WVSSGGYVDS NINTNEGRTG KDVNSVLTSI HTFDPNLGCD

301         AGTFQPCSDK ALSNLKVVVD SFRSIYGVNK GIPAGAAVAI GRYAEDVYYN

351         GNPWYLATFA AAEQLYDAIY VWKKTGSITV TATSLAFFQE LVPGVTAGTY

401         SSSSSTFTNI INAVSTYADG FLSEAAKYVP ADGSLAEQFD RNSGTPLSAL

451         HLTWSYASFL TATARRAGIV PPSWANSSAS TIPSTCSGAS VVGSYSRPTA

501         TSFPPSQTPK PGVPSGTPYT PLPCATPTSV AVTFHELVST QFGQTVKVAG

551         NAAALGNWST SAAVALDAVN YADNHPLWIG TVNLEAGDVV EYKYINVGQD

601         GSVTWESDPN HTYTVPAVAC VTQVVKEDTW QS

SEQ ID NO: 12
Tr-GA Nucleotide Sequence (1899 bp):
  1         ATGCACGTCC TGTCGACTGC GGTGCTGCTC GGCTCCGTTG CCGTTCAAAA

51         GGTCCTGGGA AGACCAGGAT CAAGCGGTCT GTCCGACGTC ACCAAGAGGT

101         CTGTTGACGA CTTCATCAGC ACCGAGACGC CTATTGCACT GAACAATCTT

151         CTTTGCAATG TTGGTCCTGA TGGATGCCGT GCATTCGGCA CATCAGCTGG

201         TGCGGTGATT GCATCTCCCA GCACAATTGA CCCGGACTAC TATTACATGT

251         GGACGCGAGA TAGCGCTCTT GTCTTCAAGA ACCTCATCGA CCGCTTCACC

301         GAAACGTACG ATGCGGGCCT GCAGCGCCGC ATCGAGCAGT ACATTACTGC

351         CCAGGTCACT CTCCAGGGCC TCTCTAACCC CTCGGGCTCC CTCGCGGACG

401         GCTCTGGTCT CGGCGAGCCC AAGTTTGAGT TGACCCTGAA GCCTTTCACC

451         GGCAACTGGG GTCGACCGCA GCGGGATGGC CCAGCTCTGC GAGCCATTGC

501         CTTGATTGGA TACTCAAAGT GGCTCATCAA CAACAACTAT CAGTCGACTG

551         TGTCCAACGT CATCTGGCCT ATTGTGCGCA ACGACCTCAA CTATGTTGCC

601         CAGTACTGGA ACCAAACCGG CTTTGACCTC TGGGAAGAAG TCAATGGGAG

651         CTCATTCTTT ACTGTTGCCA ACCAGCACCG AGCACTTGTC GAGGGCGCCA

701         CTCTTGCTGC CACTCTTGGC CAGTCGGGAA GCGCTTATTC ATCTGTTGCT

751         CCCCAGGTTT TGTGCTTTCT CCAACGATTC TGGGTGTCGT CTGGTGGATA

801         CGTCGACTCC AACATCAACA CCAACGAGGG CAGGACTGGC AAGGATGTCA
```

-continued

| SEQUENCE LISTING | |
|---|---|
| 851 | ACTCCGTCCT GACTTCCATC CACACCTTCG ATCCCAACCT TGGCTGTGAC |
| 901 | GCAGGCACCT TCCAGCCATG CAGTGACAAA GCGCTCTCCA ACCTCAAGGT |
| 951 | TGTTGTCGAC TCCTTCCGCT CCATCTACGG CGTGAACAAG GGCATTCCTG |
| 1001 | CCGGTGCTGC CGTCGCCATT GGCCGGTATG CAGAGGATGT GTACTACAAC |
| 1051 | GGCAACCCTT GGTATCTTGC TACATTTGCT GCTGCCGAGC AGCTGTACGA |
| 1101 | TGCCATCTAC GTCTGGAAGA AGACGGGCTC CATCACGGTG ACCGCCACCT |
| 1151 | CCCTGGCCTT CTTCCAGGAG CTTGTTCCTG GCGTGACGGC CGGGACCTAC |
| 1201 | TCCAGCAGCT CTTCGACCTT TACCAACATC ATCAACGCCG TCTCGACATA |
| 1251 | CGCCGATGGC TTCCTCAGCG AGGCTGCCAA GTACGTCCCC GCCGACGGTT |
| 1301 | CGCTGGCCGA GCAGTTTGAC CGCAACAGCG GCACTCCGCT GTCTGCGCTT |
| 1351 | CACCTGACGT GGTCGTACGC CTCGTTCTTG ACAGCCACGG CCCGTCGGGC |
| 1401 | TGGCATCGTG CCCCCCTCGT GGGCCAACAG CAGCGCTAGC ACGATCCCCT |
| 1451 | CGACGTGCTC CGGCGCGTCC GTGGTCGGAT CCTACTCGCG TCCCACCGCC |
| 1501 | ACGTCATTCC CTCCGTCGCA GACGCCCAAG CCTGGCGTGC CTTCCGGTAC |
| 1551 | TCCCTACACG CCCCTGCCCT GCGCGACCCC AACCTCCGTG GCCGTCACCT |
| 1601 | TCCACGAGCT CGTGTCGACA CAGTTTGGCC AGACGGTCAA GGTGGCGGGC |
| 1651 | AACGCCGCGG CCCTGGGCAA CTGGAGCACG AGCGCCGCCG TGGCTCTGGA |
| 1701 | CGCCGTCAAC TATGCCGATA ACCACCCCCT GTGGATTGGG ACGGTCAACC |
| 1751 | TCGAGGCTGG AGACGTCGTG GAGTACAAGT ACATCAATGT GGGCCAAGAT |
| 1801 | GGCTCCGTGA CCTGGGAGAG TGATCCCAAC CACACTTACA CGGTTCCTGC |
| 1851 | GGTGGCTTGT GTGACGCAGG TTGTCAAGGA GGACACCTGG CAGTCGTAA |

What is claimed is:

1. A method for saccharifying a starch substrate comprising at least 33.5% dry solids (ds) to produce glucose, comprising contacting the starch substrate with an Fv-GA glucoamylase encoded by SEQ ID NO: 1 and a Tr-GA variant CS4 glucoamylase encoded by SEQ ID NO: 9.

2. The method of claim 1, further comprising fermenting the glucose to produce alcohol.

3. The method of claim 1, further comprising fermenting the glucose to produce ethanol.

4. The method of claim 1, wherein the saccharified starch substrate results in a reduced level of DP4+.

5. The method of claim 4, wherein the reduced level of DP4+ is lower than would be achieved under the same saccharification conditions, using the same total glucoamylase dose of Fv-GA or Tr-GA variant CS4 individually.

6. The method of claim 3, wherein saccharifying and fermenting are carried out as a simultaneous saccharification and fermentation (SSF) process.

7. The method of claim 2, wherein the fermented glucose results in an increased ethanol final concentration.

8. The method of claim 7, wherein the increased ethanol final concentration is higher than would be achieved under the same saccharification and fermentation conditions, using the same total glucoamylase dose of Fv-GA or Tr-GA variant CS4 individually.

* * * * *

SEQUENCE LISTING

<160> NUMBER OF SEQ ID NOS: 12

<210> SEQ ID NO 1
<211> LENGTH: 582
<212> TYPE: PRT
<213> ORGANISM: Fusarium verticillioides

<400> SEQUENCE: 1

```
Met Phe Thr Gln Ile Leu Tyr Gly Leu Thr Ala Leu Ser Ala Leu Gln
1               5                   10                  15

Gly Gln Val Thr Ala Ser Pro Gly Gly Ser Ser Leu Asp Arg Phe Ile
            20                  25                  30

Ser Lys Glu Ala Asp Ile Ser Ile Lys Gly Val Leu Ala Asn Ile Gly
        35                  40                  45

Ala Asp Gly Lys Arg Ala Gln Gly Ala Ala Pro Gly Ala Val Val Ala
    50                  55                  60

Ser Pro Ser Arg Thr Asp Pro Asp Tyr Trp Tyr Thr Trp Thr Arg Asp
65                  70                  75                  80

Ser Ala Leu Thr Tyr Lys Val Leu Val Glu Arg Phe Ile His Gly Asp
                85                  90                  95

Lys Ser Leu Gln Arg Lys Ile Asp Glu Tyr Val Ser Ala Gln Ala Lys
            100                 105                 110
```

```
Leu Gln Gly Val Thr Asn Pro Ser Gly Gly Pro Glu Ser Gly Gly Leu
            115                 120                 125

Gly Glu Pro Lys Phe His Val Asn Leu Thr Ala Phe Thr Gly Ser Trp
130                 135                 140

Gly Arg Pro Gln Arg Asp Gly Pro Pro Leu Arg Ala Thr Ala Leu Thr
145                 150                 155                 160

Leu Tyr Ala Asn Trp Leu Val Ser His Gly Asp Arg Ser Lys Ala Val
            165                 170                 175

Asn Lys Val Trp Pro Val Ile Glu Lys Asp Leu Ala Tyr Thr Val Lys
            180                 185                 190

Phe Trp Asn Arg Thr Gly Tyr Asp Leu Trp Glu Glu Val Asn Gly Ser
            195                 200                 205

Ser Phe Phe Thr Leu Ser Ala Ser His Arg Ala Leu Val Glu Gly Ala
    210                 215                 220

Ala Leu Ala Lys Lys Leu Gly Lys Ser Cys Ser Asp Cys Ala Thr Asn
225                 230                 235                 240

Ala Pro Arg Val Leu Cys Phe Met Gln Ser Phe Trp Thr Gly Ser Tyr
                245                 250                 255

Ile Asp Ser Asn Ile Asn Val Asn Asp Gly Arg Lys Gly Leu Asp Ala
            260                 265                 270

Asn Ser Ile Leu Ser Ser Ile His Thr Phe Asp Pro Ser Ser Lys Cys
            275                 280                 285

Thr Asp Ser Thr Phe Gln Pro Cys Ser Ser Arg Ala Leu Ala Asn His
    290                 295                 300

Lys Glu Val Val Asp Ser Phe Arg Ser Ile Tyr Gly Val Asn Lys Asn
305                 310                 315                 320

Arg Gly Lys Gly Lys Ala Ala Val Gly Arg Tyr Ser Glu Asp Val
                325                 330                 335

Tyr Tyr Asp Gly Asn Pro Trp Tyr Leu Ala Thr Leu Ala Ala Ala Glu
            340                 345                 350

Gln Leu Tyr Ala Ala Val Tyr Gln Trp Asn Lys Ile Gly Ser Ile Thr
    355                 360                 365

Val Asp Ser Val Ser Leu Pro Phe Phe Ser Asp Leu Val Pro Lys Val
    370                 375                 380

Ser Lys Gly Thr Tyr Arg Lys Asn Ser Lys Thr Tyr Lys Ala Ile Ile
385                 390                 395                 400

Lys Ala Val Thr Ser Tyr Ala Asp Gly Phe Val Ala Val Gln Thr
                405                 410                 415

Tyr Thr Pro Lys Asp Gly Ser Leu Ala Glu Gln Phe Asp Lys Ser Thr
                420                 425                 430

Gly Thr Pro Lys Ser Ala Val His Leu Thr Trp Ser Tyr Ala Ser Phe
            435                 440                 445

Val Gly Ala Ala Glu Arg Arg Thr Gly Val Val Pro Pro Ala Trp Gly
    450                 455                 460

Glu Ser Asn Ala Asn Lys Val Pro Ala Val Cys Glu Ala Ala Pro Ala
465                 470                 475                 480

Cys Asp Thr Thr Ile Thr Phe Asn Val Lys Asn Val Asp Val Thr Ser
                485                 490                 495

Asp Gln Lys Val Tyr Ile Val Gly Gly Ile Thr Gln Leu Ser Asn Trp
            500                 505                 510

Ala Pro Ala Asp Gly Ile Ala Leu Glu Glu Ser Thr Ser Thr Lys Gly
    515                 520                 525
```

```
Leu Trp Thr Val Lys Val Lys Ile Pro Ser Asp Thr Ser Phe Glu Tyr
    530             535             540

Lys Tyr Ile Lys Lys Thr Ser Asp Gly Thr Val Thr Trp Glu Ser Asp
545             550             555             560

Pro Asn Asn Ser Ala Ala Thr Gly Ser Lys Cys Gly Ser Ser Ser Thr
                565             570             575

Ile Asn Asp Glu Trp Arg
            580

<210> SEQ ID NO 2
<211> LENGTH: 1802
<212> TYPE: DNA
<213> ORGANISM: Fusarium verticillioides

<400> SEQUENCE: 2
atgtttactc agatcttgta tggcctcacg gccttatctg ccctccaagg tcaggtcact     60
gcatcaccag gcggttccag ccttgatcgc ttcatttcca agaggccga catctccatc    120 aagggcgtgc ttgccaatat tggcgccgat ggcaagcgag cccaaggcgc tgcacctggc    180
gccgttgtag caagtccatc gagaacagat ccagactgta agtcaatatt cttgatagta    240
tcgcaaatgg atgactgaga cgttttctag actggtacac atggacccga ctccgcct     300 tgacatacaa agtccttgtt gagcgcttca ttcacggaga caagtctctc cagcgcaaga    360
tcgacgaata tgtctctgcc caagccaagc tccaggcgt caccaaccca tctggcggcc    420
ccgagtcagg cggccttggg aacccaagt ttcacgtcaa cctcacagct ttcacaggat    480
cctggggtcg tcctcaacga gatggccctc ctctgagagc tactgcattg acgctgtacg    540
ccaactggct tgtttctcac ggcgaccgct ccaaggccgt caacaaggtt tggcctgtca    600
ttgagaagga tcttgcatac accgtcaagt tctggaacag aaccggttac gatctttggg    660
aggaggttaa cggatcttcg ttcttcaccc tctctgcttc acatcgtgct ctggttgagg    720
gagctgctct tgctaagaag cttggcaagt cttgctccga ctgcgcaacc aacgcccccc    780
gtgttctctg cttcatgcaa agcttctgga ccggcagcta catcgactcg aacatcaatg    840
tcaacgatgg ccgcaagggt cttgatgcca actccattct gtcttctatt cacacctttg    900
atccttcttc gaagtgcaca gactctacct tccagccttg ttcttcaagg gctcttgcga    960
accacaagga agtagtggac tctttccgct ccatctatgg tgtcaacaaa acagaggta   1020 aaggtaaagc tgctgctgtc ggtcgataca gtgaggatgt gtactacgac ggtaacccctt   1080 ggtacttggc tactcttgct gctgccgagc aactgtacgc tgctgtctat caatggaaca   1140
agatcggttc catcacagtt gatagtgtgt cgctccccctt tttcagtgac cttgtaccaa   1200
aggtttccaa gggaacctat cgcaagaaca gcaagacata caaggctatt atcaaggctg   1260
tcacttcata cgctgatggc tttgtcgccg ttgtgcagac ctatactccc aaagatggct   1320
ccctcgcaga gcagttcgat aagtctactg aactcccaa gtcagctgtt cacctaacct   1380
ggtcctacgc ctcctttgtc ggtgctgccg agcgtcgtac tggcgtcgtt cctccagctt   1440
ggggcgagag caacgccaac aaggtgcctg ctgtttgcga agcagctcca gcctgcgaca   1500
ccaccatcac gttcaatgtg aagaacgttg atgtcacgtc ggaccagaag gtttacattg   1560
ttggcgggat cactcaactt tccaactggg ccctgctga cggcattgcg cttgaggaat   1620
ccacgagcac caagggcttg tggactgtga aggtcaagat tccatctgat accagctttg   1680
agtataagta tataaagaag acgagtgatg gaactgttac atgggagagt gaccccaata   1740
acagtgcggc gacgggcagc aagtgcggaa gcagcagtac catcaacgat gagtggaggt   1800
``` aa                                                                    1802

<210> SEQ ID NO 3
<211> LENGTH: 631
<212> TYPE: PRT
<213> ORGANISM: Aspergillus fumigatus

<400> SEQUENCE: 3

Met Pro Arg Leu Ser Tyr Ala Leu Cys Ala Leu Ser Leu Gly His Ala
1               5                   10                  15

Ala Ile Ala Ala Pro Gln Leu Ser Ala Arg Ala Thr Gly Ser Leu Asp
            20                  25                  30

Ser Trp Leu Gly Thr Glu Thr Thr Val Ala Leu Asn Gly Ile Leu Ala
        35                  40                  45

Asn Ile Gly Ala Asp Gly Ala Tyr Ala Lys Ser Ala Lys Pro Gly Ile
    50                  55                  60

Ile Ile Ala Ser Pro Ser Thr Ser Glu Pro Asp Tyr Tyr Tyr Thr Trp
65                  70                  75                  80

Thr Arg Asp Ala Ala Leu Val Thr Lys Val Leu Val Asp Leu Phe Arg
                85                  90                  95

Asn Gly Asn Leu Gly Leu Gln Lys Val Ile Thr Glu Tyr Val Asn Ser
            100                 105                 110

Gln Ala Tyr Leu Gln Thr Val Ser Asn Pro Ser Gly Gly Leu Ala Ser
        115                 120                 125

Gly Gly Leu Ala Glu Pro Lys Tyr Asn Val Asp Met Thr Ala Phe Thr
130                 135                 140

Gly Ala Trp Gly Arg Pro Gln Arg Asp Gly Pro Ala Leu Arg Ala Thr
145                 150                 155                 160

Ala Leu Ile Asp Phe Gly Asn Trp Leu Ile Asp Asn Gly Tyr Ser Ser
                165                 170                 175

Tyr Ala Val Asn Asn Ile Trp Pro Ile Val Arg Asn Asp Leu Ser Tyr
            180                 185                 190

Val Ser Gln Tyr Trp Ser Gln Ser Gly Phe Asp Leu Trp Glu Glu Val
        195                 200                 205

Asn Ser Met Ser Phe Phe Thr Val Ala Val Gln His Arg Ala Leu Val
210                 215                 220

Glu Gly Ser Thr Phe Ala Lys Arg Val Gly Ala Ser Cys Ser Trp Cys
225                 230                 235                 240

Asp Ser Gln Ala Pro Gln Ile Leu Cys Tyr Met Gln Ser Phe Trp Thr
                245                 250                 255

Gly Ser Tyr Ile Asn Ala Asn Thr Gly Gly Gly Arg Ser Gly Lys Asp
            260                 265                 270

Ala Asn Thr Val Leu Ala Ser Ile His Thr Phe Asp Pro Glu Ala Gly
        275                 280                 285

Cys Asp Asp Thr Thr Phe Gln Pro Cys Ser Pro Arg Ala Leu Ala Asn
290                 295                 300

His Lys Val Tyr Thr Asp Ser Phe Arg Ser Val Tyr Ala Ile Asn Ser
305                 310                 315                 320

Gly Ile Pro Gln Gly Ala Ala Val Ser Ala Gly Arg Tyr Pro Glu Asp
                325                 330                 335

Val Tyr Tyr Asn Gly Asn Pro Trp Phe Leu Thr Thr Leu Ala Ala Ala
            340                 345                 350

Glu Gln Leu Tyr Asp Ala Ile Tyr Gln Trp Lys Lys Ile Gly Ser Ile
        355                 360                 365

```
Ser Ile Thr Ser Thr Ser Leu Ala Phe Phe Lys Asp Ile Tyr Ser Ser
    370                 375                 380

Ala Ala Val Gly Thr Tyr Ala Ser Ser Thr Ser Thr Phe Thr Asp Ile
385                 390                 395                 400

Ile Asn Ala Val Lys Thr Tyr Ala Asp Gly Tyr Val Ser Ile Val Gln
                405                 410                 415

Ala His Ala Met Asn Asn Gly Ser Leu Ser Glu Gln Phe Asp Lys Ser
            420                 425                 430

Ser Gly Leu Ser Leu Ser Ala Arg Asp Leu Thr Trp Ser Tyr Ala Ala
        435                 440                 445

Phe Leu Thr Ala Asn Met Arg Arg Asn Gly Val Val Pro Ala Pro Trp
    450                 455                 460

Gly Ala Ala Ser Ala Asn Ser Val Pro Ser Ser Cys Ser Met Gly Ser
465                 470                 475                 480

Ala Thr Gly Thr Tyr Ser Thr Ala Thr Ala Thr Ser Trp Pro Ser Thr
                485                 490                 495

Leu Thr Ser Gly Ser Pro Gly Ser Thr Thr Val Gly Thr Thr Thr
                500                 505                 510

Ser Thr Thr Ser Gly Thr Ala Ala Glu Thr Ala Cys Ala Thr Pro Thr
        515                 520                 525

Ala Val Ala Val Thr Phe Asn Glu Ile Ala Thr Thr Tyr Gly Glu
    530                 535                 540

Asn Val Tyr Ile Val Gly Ser Ile Ser Glu Leu Gly Asn Trp Asp Thr
545                 550                 555                 560

Ser Lys Ala Val Ala Leu Ser Ala Ser Lys Tyr Thr Ser Ser Asn Asn
                565                 570                 575

Leu Trp Tyr Val Ser Val Thr Leu Pro Ala Gly Thr Thr Phe Glu Tyr
            580                 585                 590

Lys Tyr Ile Arg Lys Glu Ser Asp Gly Ser Ile Val Trp Glu Ser Asp
        595                 600                 605

Pro Asn Arg Ser Tyr Thr Val Pro Ala Ala Cys Gly Val Ser Thr Ala
    610                 615                 620

Thr Glu Asn Asp Thr Trp Gln
625                 630

<210> SEQ ID NO 4
<211> LENGTH: 2060
<212> TYPE: DNA
<213> ORGANISM: Aspergillus fumigatus

<400> SEQUENCE: 4
atgcctcgcc tttcctacgc gctctgtgcg ctgtctctcg ggcatgctgc tattgcagct      60
cctcagttat ccgctcgtgc taccggcagc ttggactcct ggttgggtac tgagaccacc     120
gttgcgctca atggtattct ggccaacatc ggtgccgacg tgcttatgc gaagagcgct      180 aagcctggca taatcattgc cagtccgagc accagcgaac cagactgtga gaaccttcct     240
gaactggccc tgtccggcag tcattgacct cggtagacta ctatacctgg acgagagatg     300
ctgctctcgt cacgaaagtc ctggtcgacc tcttccgcaa cggcaacctg ggtctgcaga     360
aagtcattac cgaatacgtc aactctcagg cgtacttgca gaccgtgtct aatccgtcgg     420
gtggtcttgc gagcggaggt ctcgcggagc taagtacaa cgtcgacatg acggccttta     480
ccggagcctg gggtcgtcct cagcgtgatg gtccggctct gcgggccacc gccctcatcg     540
actttggcaa ctggctgatt gtatgttctc catacgagcc ccaggaagcg ttgctgacgt     600
```

```
ctacaggaca acggctactc cagctatgct gtcaacaaca tctggcccat tgtgcgcaac    660
gacttgtcct acgtttctca gtactggagc cagagtggct tggtgagtc ccgactctct    720 ggaagtttac aacgtgcatc gattactgac aattgagatt ctacgtgaca gatctctggg    780
aagaagtcaa ctccatgtcc ttcttcaccg tcgctgtcca gcaccgtgcc ctcgtggagg    840
gaagcacgtt cgctaaacgg gtgggagcgt cgtgctcgtg gtgtgactcg caggcccccc    900
agatcctctg ctacatgcag agtttctgga ctggctcgta tatcaacgcc aacaccggtg    960
gtggccggtc cggcaaggat gccaacaccg tcctcgccag catccatacc ttcgaccccg   1020
aagccggctg cgacgatact actttccagc cctgctctcc tcgggccctt gccaaccaca   1080
aggtgtacac cgattcgttc cgctcggtct acgcgatcaa ctccggcatc ccacagggcg   1140
ctgccgtttc cgctggccgc taccccgagg acgtctacta caacggcaac ccttggttcc   1200
tcaccaccct cgccgctgcc gagcagctct acgacgctat ctaccagtgg aagaagatcg   1260
gttccatcag catcaccagc acctcccctcg ccttcttcaa ggacatctac agctccgccg   1320
cggtcggcac ctacgcctct agcacctcca ccttcacgga catcatcaac gcggtcaaga   1380
cctacgcaga cggctacgtg agcatcgtcc aggcacacgc catgaacaac ggctcccttt   1440
cggagcaatt cgacaagtcc tctgggctgt ccctctccgc ccgcgatctg acctggtcct   1500
acgccgcttt cctcaccgcc aacatgcgtc gtaacggcgt ggtgcctgcc ccctggggcg   1560
ccgcctccgc caactccgtc ccctcgtctt gctccatggg ctcggccacg gcacctaca   1620 gcaccgcgac agccacctcc tggcccagca cgctgaccag cggctcgcca ggcagcacca   1680
ccaccgtggg caccacgacc agtaccacct ctggcaccgc cgccgagacc gcctgtgcga   1740
cccctaccgc cgtggccgtc acctttaacg agatcgccac caccacctac ggcgagaatg   1800
tttacattgt tgggtccatc tccgagctcg ggaactggga taccagcaaa gcagtggccc   1860
tgagtgcgtc caagtatacc tccagcaata acctctggta cgtgtccgtc accctgccgg   1920
ctggcacgac attcgagtac aagtatatcc gcaaggaaag cgatggctcg atcgtgtggg   1980
agagtgaccc caaccgctcg tatacggtgc cggcagcttg tggagtgtct actgcgaccg   2040
agaatgatac ttggcagtga                                               2060
```

<210> SEQ ID NO 5
<211> LENGTH: 634
<212> TYPE: PRT
<213> ORGANISM: Humicola grisea

<400> SEQUENCE: 5

Met His Thr Phe Ser Lys Leu Leu Val Leu Gly Ser Ala Val Gln Ser
1               5                   10                  15

Ala Leu Gly Arg Pro His Gly Ser Ser Arg Leu Gln Glu Arg Ala Ala
                20                  25                  30

Val Asp Thr Phe Ile Asn Thr Glu Lys Pro Ile Ala Trp Asn Lys Leu
            35                  40                  45

Leu Ala Asn Ile Gly Pro Asn Gly Lys Ala Ala Pro Gly Ala Ala Ala
        50                  55                  60

Gly Val Val Ile Ala Ser Pro Ser Arg Thr Asp Pro Pro Tyr Phe Phe
65                  70                  75                  80

Thr Trp Thr Pro Asp Ala Ala Leu Val Leu Thr Gly Ile Ile Glu Ser
                85                  90                  95

Leu Gly His Asn Tyr Asn Thr Thr Leu Gln Thr Val Ile Gln Asn Tyr
                100                 105                 110

```
Val Ala Ser Gln Ala Lys Leu Gln Gln Val Ser Asn Pro Ser Gly Thr
            115                 120                 125
Phe Ala Asp Gly Ser Gly Leu Gly Glu Ala Lys Phe Asn Val Asp Leu
        130                 135                 140
Thr Ala Phe Thr Gly Glu Trp Gly Arg Pro Gln Arg Asp Gly Pro Pro
145                 150                 155                 160
Leu Arg Ala Ile Ala Leu Ile Gln Tyr Ala Lys Trp Leu Ile Ala Asn
                165                 170                 175
Gly Tyr Lys Ser Thr Ala Lys Ser Val Val Trp Pro Val Val Lys Asn
            180                 185                 190
Asp Leu Ala Tyr Thr Ala Gln Tyr Trp Asn Glu Thr Gly Phe Asp Leu
        195                 200                 205
Trp Glu Val Pro Gly Ser Ser Phe Phe Thr Ile Ala Ser Ser His
    210                 215                 220
Arg Ala Leu Thr Glu Gly Ala Tyr Leu Ala Ala Gln Leu Asp Thr Glu
225                 230                 235                 240
Cys Pro Pro Cys Thr Thr Val Ala Pro Gln Val Leu Cys Phe Gln Gln
                245                 250                 255
Ala Phe Trp Asn Ser Lys Gly Asn Tyr Val Val Ser Thr Ser Thr Ala
            260                 265                 270
Gly Glu Tyr Arg Ser Gly Lys Asp Ala Asn Ser Ile Leu Ala Ser Ile
        275                 280                 285
His Asn Phe Asp Pro Glu Ala Gly Cys Asp Asn Leu Thr Phe Gln Pro
    290                 295                 300
Cys Ser Glu Arg Ala Leu Ala Asn His Lys Ala Tyr Val Asp Ser Phe
305                 310                 315                 320
Arg Asn Leu Tyr Ala Ile Asn Lys Gly Ile Ala Gln Gly Lys Ala Val
                325                 330                 335
Ala Val Gly Arg Tyr Ser Glu Asp Val Tyr Tyr Asn Gly Asn Pro Trp
            340                 345                 350
Tyr Leu Ala Asn Phe Ala Ala Ala Glu Gln Leu Tyr Asp Ala Ile Tyr
        355                 360                 365
Val Trp Asn Lys Gln Gly Ser Ile Thr Val Thr Ser Val Ser Leu Pro
    370                 375                 380
Phe Phe Arg Asp Leu Val Ser Ser Val Ser Thr Gly Thr Tyr Ser Lys
385                 390                 395                 400
Ser Ser Ser Thr Phe Thr Asn Ile Val Asn Ala Val Lys Ala Tyr Ala
                405                 410                 415
Asp Gly Phe Ile Glu Val Ala Ala Lys Tyr Thr Pro Ser Asn Gly Ala
            420                 425                 430
Leu Ala Glu Gln Tyr Asp Arg Asn Thr Gly Lys Pro Asp Ser Ala Ala
        435                 440                 445
Asp Leu Thr Trp Ser Tyr Ser Ala Phe Leu Ser Ala Ile Asp Arg Arg
    450                 455                 460
Ala Gly Leu Val Pro Pro Ser Trp Arg Ala Ser Val Ala Lys Ser Gln
465                 470                 475                 480
Leu Pro Ser Thr Cys Ser Arg Ile Glu Val Ala Gly Thr Tyr Val Ala
                485                 490                 495
Ala Thr Ser Thr Ser Phe Pro Ser Lys Gln Thr Pro Asn Pro Ser Ala
            500                 505                 510
Ala Pro Ser Pro Ser Pro Tyr Pro Thr Ala Cys Ala Asp Ala Ser Glu
        515                 520                 525
```

```
Val Tyr Val Thr Phe Asn Glu Arg Val Ser Thr Ala Trp Gly Glu Thr
            530                 535                 540

Ile Lys Val Val Gly Asn Val Pro Ala Leu Gly Asn Trp Asp Thr Ser
545                 550                 555                 560

Lys Ala Val Thr Leu Ser Ala Ser Gly Tyr Lys Ser Asn Asp Pro Leu
                565                 570                 575

Trp Ser Ile Thr Val Pro Ile Lys Ala Thr Gly Ser Ala Val Gln Tyr
            580                 585                 590

Lys Tyr Ile Lys Val Gly Thr Asn Gly Lys Ile Thr Trp Glu Ser Asp
                595                 600                 605

Pro Asn Arg Ser Ile Thr Leu Gln Thr Ala Ser Ser Ala Gly Lys Cys
            610                 615                 620

Ala Ala Gln Thr Val Asn Asp Ser Trp Arg
625                 630

<210> SEQ ID NO 6
<211> LENGTH: 2102
<212> TYPE: DNA
<213> ORGANISM: Humicola grisea

<400> SEQUENCE: 6
atgcatacct tctccaagct cctcgtcctg ggctctgccg tccagtctgc cctcgggcgg      60
cctcacggct cttcgcgtct ccaggaacgc gctgccgttg ataccttcat caacaccgag     120
aagcccatcg catggaacaa gctgctcgcc aacatcggcc taacggcaa agccgctccc      180 ggtgccgccg ccggcgttgt gattgccagc ccttccagga cggaccctcc ttgtacgtgg     240
tggcatggaa tggacccaag agactgtttt agatgaaaga gagtttctgc taaccgccac     300
acccagactt cttcacctgg accccggatg ccgccctggt cctcaccggc atcatcgagt     360
cccttggcca caactacaac accaccctgc agaccgtcat ccagaactac gtcgcgtcgc     420
aggccaagct gcagcaggtc tcgaacccct cgggaacctt cgccgacggc tcgggtctcg     480
gtgaggccaa gttcaatgtc gacctcactg ccttcactgg cgaatggggt cgccctcaga     540
gggacggccc gccctgcgc gccatcgctc tcatccagta cgccaagtgg ctgatcgcca      600
acggctacaa gagcacggcc aagagcgtcg tctggcccgt cgtcaagaac gatctcgcct     660
acacggccca gtactggaac gagaccggct cgatctctg gaggaggtc cccggcagct       720 cgttctttac catcgccagc tctcacaggg gtgagtcatt tattgttcag tgttttctca     780
ttgaataatt accggaatgc cactgacgcc aaacagctct gactgagggt gcttacctcg     840
ccgctcagct cgacaccgag tgcccgccct gcacgaccgt cgcccctcag gttctgtgct     900
tccagcaggc cttctggaac tccaagggca actatgtcgt ctcaacagta agatccctac     960
accaacaaaa aaaatcgaaa aggaacgtta gctgacccct tagtcaacg gcgggcgagt    1020 atcgctccgg caaggacgcc aactcgatcc tggcgtccat ccacaacttc gaccctgagg    1080
ccggctgcga caacctgacc ttccagcct gcagcgagcg cgccctggcc aaccacaagg     1140
cctatgtcga ctcgttccgc aacctctacg ccatcaacaa gggcatcgcc cagggcaagg    1200
ccgttgccgt cggccgctac tcggaggatg tctactacaa cggcaacccg tggtacctgg    1260
ccaactttgc cgccgccgag cagctctacg acgccatcta cgtgtggaac aagcagggct    1320
ccatcaccgt gacctcggtc tccctgccct tcttccgcga ccttgtctcg tcggtcagca    1380
ccggcaccta ctccaagagc agctcgacct tcaccaacat cgtcaacgcc gtcaaggcct    1440
acgccgacgg cttcatcgag gtggcggcca agtacacccc gtccaacggc gcgctcgccg    1500
```

-continued

```
agcagtacga ccgcaacacg ggcaagcccg actcggccgc cgacctgacg tggtcgtact    1560
cggccttcct ctcggccatc gaccgccgcg cgggtctcgt cccccgagc tggcgggcca     1620 gcgtggccaa gagccagctg ccgtccacct gctcgcgcat cgaggtcgcc ggcacctacg    1680
tcgccgccac gagcacctcg ttcccgtcca agcagacccc gaaccctcc gcggcgccct     1740 ccccgtcccc ctacccgacc gcctgcgcgg acgctagcga ggtgtacgtc accttcaacg    1800
agcgcgtgtc gaccgcgtgg ggcgagacca tcaaggtggt gggcaacgtg ccggcgctgg    1860
ggaactggga cacgtccaag gcggtgaccc tgtcggccag cgggtacaag tcgaatgatc    1920
ccctctggag catcacggtg cccatcaagg cgacgggctc ggccgtgcag tacaagtata    1980
tcaaggtcgg caccaacggg aagattactt gggagtcgga ccccaacagg agcattaccc    2040
tgcagacggc gtcgtctgcg ggcaagtgcg ccgcgcagac ggtgaatgat tcgtggcgtt    2100
aa                                                                   2102
```

<210> SEQ ID NO 7
<211> LENGTH: 639
<212> TYPE: PRT
<213> ORGANISM: Aspergillus niger

<400> SEQUENCE: 7

```
Met Ser Phe Arg Ser Leu Leu Ala Leu Ser Gly Leu Val Cys Thr Gly
1               5                   10                  15

Leu Ala Asn Val Ile Ser Lys Arg Ala Thr Trp Asp Ser Trp Leu Ser
            20                  25                  30

Asn Glu Ala Thr Val Ala Arg Thr Ala Ile Leu Asn Asn Ile Gly Ala
        35                  40                  45

Asp Gly Ala Trp Val Ser Gly Ala Asp Ser Gly Ile Val Val Ala Ser
    50                  55                  60

Pro Ser Thr Asp Asn Pro Asp Tyr Phe Tyr Thr Trp Thr Arg Asp Ser
65                  70                  75                  80

Gly Leu Val Leu Lys Thr Leu Val Asp Leu Phe Arg Asn Gly Asp Thr
                85                  90                  95

Ser Leu Leu Ser Thr Ile Glu Asn Tyr Ile Ser Ala Gln Ala Ile Val
            100                 105                 110

Gln Gly Ile Ser Asn Pro Ser Gly Asp Leu Ser Ser Gly Ala Gly Leu
        115                 120                 125

Gly Glu Pro Lys Phe Asn Val Asp Glu Thr Ala Tyr Thr Gly Ser Trp
    130                 135                 140

Gly Arg Pro Gln Arg Asp Gly Pro Ala Leu Arg Ala Thr Ala Met Ile
145                 150                 155                 160

Gly Phe Gly Gln Trp Leu Leu Asp Asn Gly Tyr Thr Ser Thr Ala Thr
                165                 170                 175

Asp Ile Val Trp Pro Leu Val Arg Asn Asp Leu Ser Tyr Val Ala Gln
            180                 185                 190

Tyr Trp Asn Gln Thr Gly Tyr Asp Leu Trp Glu Val Asn Gly Ser Ser
        195                 200                 205

Phe Phe Thr Ile Ala Val Gln His Arg Ala Leu Val Glu Gly Ser Ala
    210                 215                 220

Phe Ala Thr Ala Val Gly Ser Ser Cys Ser Trp Cys Asp Ser Gln Ala
225                 230                 235                 240

Pro Glu Ile Leu Cys Tyr Leu Gln Ser Phe Trp Thr Gly Ser Phe Ile
                245                 250                 255

Leu Ala Asn Phe Asp Ser Ser Arg Ser Ala Lys Asp Ala Asn Thr Leu
```

```
                    260                 265                 270
Leu Leu Gly Ser Ile His Thr Phe Asp Pro Glu Ala Ala Cys Asp Asp
                275                 280                 285

Ser Thr Phe Gln Pro Cys Ser Pro Arg Ala Leu Ala Asn His Lys Glu
                290                 295                 300

Val Val Asp Ser Phe Arg Ser Ile Tyr Thr Leu Asn Asp Gly Leu Ser
305                 310                 315                 320

Asp Ser Glu Ala Val Ala Val Gly Arg Tyr Pro Glu Asp Thr Tyr Tyr
                325                 330                 335

Asn Gly Asn Pro Trp Phe Leu Cys Thr Leu Ala Ala Glu Gln Leu
                340                 345                 350

Tyr Asp Ala Leu Tyr Gln Trp Asp Lys Gln Gly Ser Leu Glu Val Thr
                355                 360                 365

Asp Val Ser Leu Asp Phe Phe Lys Ala Leu Tyr Ser Ala Thr Gly
                370                 375                 380

Thr Tyr Ser Ser Ser Ser Thr Tyr Ser Ser Ile Val Asp Ala Val
385                 390                 395                 400

Lys Thr Phe Ala Asp Gly Phe Val Ser Ile Val Glu Thr His Ala Ala
                405                 410                 415

Ser Asn Gly Ser Met Ser Glu Gln Tyr Asp Lys Ser Asp Gly Glu Gln
                420                 425                 430

Leu Ser Ala Arg Asp Leu Thr Trp Ser Tyr Ala Ala Leu Leu Thr Ala
                435                 440                 445

Asn Asn Arg Arg Asn Val Val Pro Ser Ala Ser Trp Gly Glu Thr Ser
                450                 455                 460

Ala Ser Ser Val Pro Gly Thr Cys Ala Ala Thr Ser Ala Ile Gly Thr
465                 470                 475                 480

Tyr Ser Ser Val Thr Val Thr Ser Trp Pro Ser Ile Val Ala Thr Gly
                485                 490                 495

Gly Thr Thr Thr Thr Ala Thr Pro Thr Gly Ser Gly Ser Val Thr Ser
                500                 505                 510

Thr Ser Lys Thr Thr Ala Thr Ala Ser Lys Thr Ser Thr Ser Thr Ser
                515                 520                 525

Ser Thr Ser Cys Thr Thr Pro Thr Ala Val Ala Val Thr Phe Asp Leu
                530                 535                 540

Thr Ala Thr Thr Thr Tyr Gly Glu Asn Ile Tyr Leu Val Gly Ser Ile
545                 550                 555                 560

Ser Gln Leu Gly Asp Trp Glu Thr Ser Asp Gly Ile Ala Leu Ser Ala
                565                 570                 575

Asp Lys Tyr Thr Ser Ser Asp Pro Leu Trp Tyr Val Thr Val Thr Leu
                580                 585                 590

Pro Ala Gly Glu Ser Phe Glu Tyr Lys Phe Ile Arg Ile Glu Ser Asp
                595                 600                 605

Asp Ser Val Glu Trp Glu Ser Asp Pro Asn Arg Glu Tyr Thr Val Pro
                610                 615                 620

Gln Ala Cys Gly Thr Ser Thr Ala Thr Val Thr Asp Thr Trp Arg
625                 630                 635
```

<210> SEQ ID NO 8
<211> LENGTH: 1920
<212> TYPE: DNA
<213> ORGANISM: Aspergillus niger

<400> SEQUENCE: 8

```
atgtcgttcc gatctctact cgccctgagc ggcctcgtct gcacagggtt ggcaaatgtg    60
atttccaagc gcgcgacctg ggattcatgg ttgagcaacg aagcgaccgt ggctcgtact   120
gccatcctga ataacatcgg ggcggacggt gcttgggtgt cgggcgcgga ctctggcatt   180
gtcgttgcta gtcccagcac ggataacccg gactacttct acacctggac tcgcgactct   240
ggtctcgtcc tcaagaccct cgtcgatctc ttccgaaatg gagataccag tctcctctcc   300
accattgaga actacatctc cgcccaggca attgtccagg gtatcagtaa ccctctggt    360
gatctgtcca gcggcgctgg tctcggtgaa cccaagttca atgtcgatga gactgcctac   420
actggttctt ggggacggcc gcagcgagat ggtccggctc tgagcagcaac tgctatgatc   480
ggcttcgggc aatggctgct tgacaatggc tacaccagca ccgcaacgga cattgtttgg   540
cccctcgtta ggaacgacct gtcgtatgtg gctcaatact ggaaccagac aggatatgat   600
ctctgggaag tcaatggctc gtcttccttt acgattgctg tgcaacaccg cgcccttgtc   660
gaaggtagtg ccttcgcgac ggccgtcggc tcgtcctgct cctggtgtga ttctcaggca   720
cccgaaattc tctgctacct gcagtccttc tggaccggca gcttcattct ggccaacttc   780
gatagcagcc gttccgccaa ggacgcaaac accctcctgc tgggaagcat ccacaccttt   840
gatcctgagg ccgcatgcga cgactccacc ttccagcct  gctccccgcg cgcgctcgcc   900
aaccacaagg aggttgtaga ctctttccgc tcaatctata ccctcaacga tggtctcagt   960
gacagcgagg ctgttgcggt gggtcggtac cctgaggaca cgtactacaa cggcaacccg  1020
tggttcctgt gcaccttggc tgccgcagag cagttgtacg atgctctata ccagtgggac  1080
aagcagggc cgttggaggt cacagatgtg tcgctggact tcttcaaggc actgtacagc  1140
gatgctactg gcacctactc ttcgtccagt tcgacttata gtagcattgt agatgccgtg  1200
aagactttcg ccgatggctt cgtctctatt gtggaaactc acgccgcaag caacggctcc  1260
atgtccgagc aatacgacaa gtctgatggc gagcagcttt ccgctcgcga cctgacctgg  1320
tcttatgctc tctgctgac  cgccaacaac cgtcgtaacg tcgtgccttc cgcttcttgg  1380
ggcgagacct ctgccagcag cgtgcccggc acctgtgcgg ccacatctgc cattggtacc  1440
tacagcagtg tgactgtcac ctcgtggccg agtatcgtgg ctactggcgg caccactacg  1500
acggctaccc ccactggatc cggcagcgtg acctcgacca gcaagaccac cgcgactgct  1560
agcaagacca gcaccagtac gtcatcaacc tcctgtacca ctcccaccgc cgtggctgtg  1620
actttcgatc tgacagctac caccacctac ggcgagaaca tctacctggt cggatcgatc  1680
tctcagctgg gtgactggga accagcgac ggcatagctc tgagtgctga caagtacact  1740
tccagcgacc cgctctggta tgtcactgtg actctgccgg ctggtgagtc gtttgagtac  1800
aagtttatcc gcattgagag cgatgactcc gtggagtggg agagtgatcc caaccgagaa  1860
tacaccgttc ctcaggcgtg cggaacgtcg accgcgacgg tgactgacac ctggcggtag  1920
```

<210> SEQ ID NO 9
<211> LENGTH: 599
<212> TYPE: PRT
<213> ORGANISM: Trichoderma reesei

<400> SEQUENCE: 9

```
Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
```

```
            35                  40                  45
Tyr Met Trp Thr Arg Asp Ser Ala Leu Val Phe Lys Asn Leu Ile Asp
 50                  55                  60

Arg Phe Thr Glu Thr Tyr Asp Ala Gly Leu Gln Arg Arg Ile Glu Gln
 65                  70                  75                  80

Tyr Ile Thr Ala Gln Val Thr Leu Gln Gly Leu Ser Asn Pro Ser Gly
                 85                  90                  95

Ser Leu Ala Asp Gly Ser Gly Leu Gly Glu Pro Lys Phe Glu Leu Thr
                100                 105                 110

Leu Lys Pro Phe Thr Gly Asn Trp Gly Arg Pro Gln Arg Asp Gly Pro
            115                 120                 125

Ala Leu Arg Ala Ile Ala Leu Ile Gly Tyr Ser Lys Trp Leu Ile Asn
            130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
            195                 200                 205

Ser Gly Ser Ala Tyr Ser Ser Val Ala Pro Gln Val Leu Cys Phe Leu
210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Asp Ser
            275                 280                 285

Phe Arg Ser Ile Tyr Gly Val Asn Lys Gly Ile Pro Ala Gly Ala Ala
290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335

Tyr Val Trp Lys Lys Thr Gly Ser Ile Thr Val Thr Ala Thr Ser Leu
            340                 345                 350

Ala Phe Phe Gln Glu Leu Val Pro Gly Val Thr Ala Gly Thr Tyr Ser
            355                 360                 365

Ser Ser Ser Thr Phe Thr Asn Ile Ile Asn Ala Val Ser Thr Tyr
            370                 375                 380

Ala Asp Gly Phe Leu Ser Glu Ala Ala Lys Tyr Val Pro Ala Asp Gly
385                 390                 395                 400

Ser Leu Ala Glu Gln Phe Asp Arg Asn Ser Gly Thr Pro Leu Ser Ala
                405                 410                 415

Val His Leu Thr Trp Ser Tyr Ala Ser Phe Leu Thr Ala Ala Ala Arg
            420                 425                 430

Arg Ala Gly Ile Val Pro Pro Ser Trp Ala Asn Ser Ser Ala Ser Thr
            435                 440                 445

Ile Pro Ser Thr Cys Ser Gly Ala Ser Val Val Gly Ser Tyr Ser Arg
450                 455                 460
```

```
Pro Thr Ala Thr Ser Phe Pro Pro Ser Gln Thr Pro Lys Pro Gly Val
465                 470                 475                 480

Pro Ser Gly Thr Pro Tyr Thr Pro Leu Pro Cys Ala Thr Pro Thr Ser
            485                 490                 495

Val Ala Val Thr Phe His Glu Leu Val Ser Thr Gln Phe Gly His Thr
                500                 505                 510

Val Lys Val Ala Gly Asn Ala Ala Leu Gly Asn Trp Ser Thr Ser
            515                 520                 525

Ala Ala Val Ala Leu Asp Ala Val Asn Tyr Arg Asp Asn His Pro Leu
530                 535                 540

Trp Ile Gly Thr Val Asn Leu Glu Ala Gly Asp Val Val Glu Tyr Lys
545                 550                 555                 560

Tyr Ile Ile Val Gly Gln Asp Gly Ser Val Thr Trp Glu Ser Asp Pro
                565                 570                 575

Asn His Thr Tyr Thr Val Pro Ala Val Ala Cys Val Thr Gln Val Val
                580                 585                 590

Lys Glu Asp Thr Trp Gln Ser
        595

<210> SEQ ID NO 10
<211> LENGTH: 599
<212> TYPE: PRT
<213> ORGANISM: Trichoderma reesei

<400> SEQUENCE: 10

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
            20                  25                  30

Ala Gly Ala Val Ile Ala Ser Pro Ser Thr Ile Asp Pro Asp Tyr Tyr
        35                  40                  45

Tyr Met Trp Thr Arg Asp Ser Ala Leu Val Phe Lys Asn Leu Ile Asp
50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Val Ala Pro Gln Val Leu Cys Phe Leu
210                 215                 220

Gln Arg Phe Trp Val Ser Ser Gly Gly Tyr Val Asp Ser Asn Ile Asn
```

```
         225                 230                 235                 240
     Thr Asn Glu Gly Arg Thr Gly Lys Asp Val Asn Ser Val Leu Thr Ser
                     245                 250                 255

Ile His Thr Phe Asp Pro Asn Leu Gly Cys Asp Ala Gly Thr Phe Gln
                     260                 265                 270

Pro Cys Ser Asp Lys Ala Leu Ser Asn Leu Lys Val Val Asp Ser
                 275                 280                 285

Phe Arg Ser Ile Tyr Gly Val Asn Lys Gly Ile Pro Ala Gly Ala Ala
                 290                 295                 300

Val Ala Ile Gly Arg Tyr Ala Glu Asp Val Tyr Tyr Asn Gly Asn Pro
     305                 310                 315                 320

Trp Tyr Leu Ala Thr Phe Ala Ala Glu Gln Leu Tyr Asp Ala Ile
                     325                 330                 335

Tyr Val Trp Lys Lys Thr Gly Ser Ile Thr Val Thr Ala Thr Ser Leu
                     340                 345                 350

Ala Phe Phe Gln Glu Leu Val Pro Gly Val Thr Ala Gly Thr Tyr Ser
                 355                 360                 365

Ser Ser Ser Ser Thr Phe Thr Asn Ile Ile Asn Ala Val Ser Thr Tyr
             370                 375                 380

Ala Asp Gly Phe Leu Ser Glu Ala Ala Lys Tyr Val Pro Ala Asp Gly
     385                 390                 395                 400

Ser Leu Ala Glu Gln Phe Asp Arg Asn Ser Gly Thr Pro Leu Ser Ala
                     405                 410                 415

Leu His Leu Thr Trp Ser Tyr Ala Ser Phe Leu Thr Ala Thr Ala Arg
                     420                 425                 430

Arg Ala Gly Ile Val Pro Pro Ser Trp Ala Asn Ser Ser Ala Ser Thr
                 435                 440                 445

Ile Pro Ser Thr Cys Ser Gly Ala Ser Val Val Gly Ser Tyr Ser Arg
                 450                 455                 460

Pro Thr Ala Thr Ser Phe Pro Ser Gln Thr Pro Lys Pro Gly Val
     465                 470                 475                 480

Pro Ser Gly Thr Pro Tyr Thr Pro Leu Pro Cys Ala Thr Pro Thr Ser
                     485                 490                 495

Val Ala Val Thr Phe His Glu Leu Val Ser Thr Gln Phe Gly Gln Thr
                 500                 505                 510

Val Lys Val Ala Gly Asn Ala Ala Leu Gly Asn Trp Ser Thr Ser
                 515                 520                 525

Ala Ala Val Ala Leu Asp Ala Val Asn Tyr Ala Asp Asn His Pro Leu
     530                 535                 540

Trp Ile Gly Thr Val Asn Leu Glu Ala Gly Asp Val Val Glu Tyr Lys
     545                 550                 555                 560

Tyr Ile Asn Val Gly Gln Asp Gly Ser Val Thr Trp Glu Ser Asp Pro
                     565                 570                 575

Asn His Thr Tyr Thr Val Pro Ala Val Ala Cys Val Thr Gln Val Val
                     580                 585                 590

Lys Glu Asp Thr Trp Gln Ser
                 595

<210> SEQ ID NO 11
<211> LENGTH: 632
<212> TYPE: PRT
<213> ORGANISM: Trichoderma reesei

<400> SEQUENCE: 11
```

```
Met His Val Leu Ser Thr Ala Val Leu Leu Gly Ser Val Ala Val Gln
1               5                   10                  15

Lys Val Leu Gly Arg Pro Gly Ser Ser Gly Leu Ser Asp Val Thr Lys
            20                  25                  30

Arg Ser Val Asp Asp Phe Ile Ser Thr Glu Thr Pro Ile Ala Leu Asn
        35                  40                  45

Asn Leu Leu Cys Asn Val Gly Pro Asp Gly Cys Arg Ala Phe Gly Thr
    50                  55                  60

Ser Ala Gly Ala Val Ile Ala Ser Pro Ser Thr Ile Asp Pro Asp Tyr
65                  70                  75                  80

Tyr Tyr Met Trp Thr Arg Asp Ser Ala Leu Val Phe Lys Asn Leu Ile
                85                  90                  95

Asp Arg Phe Thr Glu Thr Tyr Asp Ala Gly Leu Gln Arg Arg Ile Glu
            100                 105                 110

Gln Tyr Ile Thr Ala Gln Val Thr Leu Gln Gly Leu Ser Asn Pro Ser
        115                 120                 125

Gly Ser Leu Ala Asp Gly Ser Gly Leu Gly Glu Pro Lys Phe Glu Leu
    130                 135                 140

Thr Leu Lys Pro Phe Thr Gly Asn Trp Gly Arg Pro Gln Arg Asp Gly
145                 150                 155                 160

Pro Ala Leu Arg Ala Ile Ala Leu Ile Gly Tyr Ser Lys Trp Leu Ile
                165                 170                 175

Asn Asn Asn Tyr Gln Ser Thr Val Ser Asn Val Ile Trp Pro Ile Val
            180                 185                 190

Arg Asn Asp Leu Asn Tyr Val Ala Gln Tyr Trp Asn Gln Thr Gly Phe
        195                 200                 205

Asp Leu Trp Glu Glu Val Asn Gly Ser Ser Phe Phe Thr Val Ala Asn
    210                 215                 220

Gln His Arg Ala Leu Val Glu Gly Ala Thr Leu Ala Ala Thr Leu Gly
225                 230                 235                 240

Gln Ser Gly Ser Ala Tyr Ser Ser Val Ala Pro Gln Val Leu Cys Phe
                245                 250                 255

Leu Gln Arg Phe Trp Val Ser Ser Gly Gly Tyr Val Asp Ser Asn Ile
            260                 265                 270

Asn Thr Asn Glu Gly Arg Thr Gly Lys Asp Val Asn Ser Val Leu Thr
        275                 280                 285

Ser Ile His Thr Phe Asp Pro Asn Leu Gly Cys Asp Ala Gly Thr Phe
    290                 295                 300

Gln Pro Cys Ser Asp Lys Ala Leu Ser Asn Leu Lys Val Val Val Asp
305                 310                 315                 320

Ser Phe Arg Ser Ile Tyr Gly Val Asn Lys Gly Ile Pro Ala Gly Ala
                325                 330                 335

Ala Val Ala Ile Gly Arg Tyr Ala Glu Asp Val Tyr Tyr Asn Gly Asn
            340                 345                 350

Pro Trp Tyr Leu Ala Thr Phe Ala Ala Ala Glu Gln Leu Tyr Asp Ala
        355                 360                 365

Ile Tyr Val Trp Lys Lys Thr Gly Ser Ile Thr Val Thr Ala Thr Ser
    370                 375                 380

Leu Ala Phe Phe Gln Glu Leu Val Pro Gly Val Thr Ala Gly Thr Tyr
385                 390                 395                 400

Ser Ser Ser Ser Ser Thr Phe Thr Asn Ile Ile Asn Ala Val Ser Thr
                405                 410                 415

Tyr Ala Asp Gly Phe Leu Ser Glu Ala Ala Lys Tyr Val Pro Ala Asp
```

```
              420           425           430
Gly Ser Leu Ala Glu Gln Phe Asp Arg Asn Ser Gly Thr Pro Leu Ser
            435                 440                 445
Ala Leu His Leu Thr Trp Ser Tyr Ala Ser Phe Leu Thr Ala Thr Ala
        450                 455                 460
Arg Arg Ala Gly Ile Val Pro Pro Ser Trp Ala Asn Ser Ser Ala Ser
465                 470                 475                 480
Thr Ile Pro Ser Thr Cys Ser Gly Ala Ser Val Val Gly Ser Tyr Ser
                485                 490                 495
Arg Pro Thr Ala Thr Ser Phe Pro Pro Ser Gln Thr Pro Lys Pro Gly
            500                 505                 510
Val Pro Ser Gly Thr Pro Tyr Thr Pro Leu Pro Cys Ala Thr Pro Thr
        515                 520                 525
Ser Val Ala Val Thr Phe His Glu Leu Val Ser Thr Gln Phe Gly Gln
    530                 535                 540
Thr Val Lys Val Ala Gly Asn Ala Ala Ala Leu Gly Asn Trp Ser Thr
545                 550                 555                 560
Ser Ala Ala Val Ala Leu Asp Ala Val Asn Tyr Ala Asp Asn His Pro
                565                 570                 575
Leu Trp Ile Gly Thr Val Asn Leu Glu Ala Gly Asp Val Val Glu Tyr
            580                 585                 590
Lys Tyr Ile Asn Val Gly Gln Asp Gly Ser Val Thr Trp Glu Ser Asp
        595                 600                 605
Pro Asn His Thr Tyr Thr Val Pro Ala Val Ala Cys Val Thr Gln Val
    610                 615                 620
Val Lys Glu Asp Thr Trp Gln Ser
625                 630

<210> SEQ ID NO 12
<211> LENGTH: 1899
<212> TYPE: DNA
<213> ORGANISM: Trichoderma reesei

<400> SEQUENCE: 12
atgcacgtcc tgtcgactgc ggtgctgctc ggctccgttg ccgttcaaaa ggtcctggga      60
agaccaggat caagcggtct gtccgacgtc accaagaggt ctgttgacga cttcatcagc     120
accgagacgc ctattgcact gaacaatctt ctttgcaatg ttggtcctga tggatgccgt     180
gcattcggca catcagctgg tgcggtgatt gcatctccca gcacaattga cccggactac     240
tattacatgt ggacgcgaga tagcgctctt gtcttcaaga acctcatcga ccgcttcacc     300
gaaacgtacg atgcgggcct gcagcgccgc atcgagcagt acattactgc ccaggtcact     360
ctccagggcc tctctaaccc ctcgggctcc ctcgcggacg gctctggtct cggcgagccc     420
aagtttgagt tgaccctgaa gcctttcacc ggcaactggg gtcgaccgca gcgggatggc     480
ccagctctgc gagccattgc cttgattgga tactcaaagt ggctcatcaa caacaactat     540
cagtcgactg tgtccaacgt catctggcct attgtgcgca cgacctcaa ctatgttgcc     600 cagtactgga ccaaaccggc ttttgacctc tgggaagaag tcaatgggag ctcattcttt     660
actgttgcca accagcaccg agcacttgtc gagggcgcca ctcttgctgc cactcttggc     720
cagtcgggaa gcgcttattc atctgttgct ccccaggttt tgtgctttct ccaacgattc     780
tgggtgtcgt ctggtggata cgtcgactcc aacatcaaca ccaacgaggg caggactggc     840
aaggatgtca actccgtcct gacttccatc acacccttcg atcccaacct tggctgtgac     900
```

```
                                                -continued gcaggcacct tccagccatg cagtgacaaa gcgctctcca acctcaaggt tgttgtcgac      960
tccttccgct ccatctacgg cgtgaacaag ggcattcctg ccggtgctgc cgtcgccatt     1020
ggccggtatg cagaggatgt gtactacaac ggcaaccctt ggtatcttgc tacatttgct    1080
gctgccgagc agctgtacga tgccatctac gtctggaaga agacgggctc catcacggtg    1140
accgccacct ccctggcctt cttccaggag cttgttcctg gcgtgacggc cgggacctac    1200
tccagcagct cttcgacctt taccaacatc atcaacgccg tctcgacata cgccgatggc    1260
ttcctcagcg aggctgccaa gtacgtcccc gccgacggtt cgctggccga gcagtttgac    1320
cgcaacagcg gcactccgct gtctgcgctt cacctgacgt ggtcgtacgc ctcgttcttg    1380
acagccacgg cccgtcgggc tggcatcgtg ccccctcgt gggccaacag cagcgctagc    1440
acgatcccct cgacgtgctc cggcgcgtcc gtggtcggat cctactcgcg tcccaccgcc    1500
acgtcattcc ctccgtcgca gacgccaag cctggcgtgc cttccggtac tccctacacg    1560
cccctgccct gcgcgacccc aacctccgtg gccgtcacct tccacgagct cgtgtcgaca    1620
cagtttggcc agacggtcaa ggtggcgggc aacgccgcgg ccctgggcaa ctggagcacg    1680
agcgccgccg tggctctgga cgccgtcaac tatgccgata accaccccct gtggattggg    1740
acggtcaacc tcgaggctgg agacgtcgtg gagtacaagt acatcaatgt gggccaagat    1800
ggctccgtga cctgggagag tgatcccaac cacacttaca cggttcctgc ggtggcttgt    1860
gtgacgcagg ttgtcaagga ggacacctgg cagtcgtaa                            1899
```